United States Patent
Rothe et al.

(10) Patent No.: US 12,193,638 B2
(45) Date of Patent: Jan. 14, 2025

(54) COMPLEX SHAPE STEERABLE TISSUE VISUALIZATION AND MANIPULATION CATHETER

(71) Applicant: Intuitive Surgical Operations, Inc., Sunnyvale, CA (US)

(72) Inventors: Chris A. Rothe, San Mateo, CA (US); David Miller, Cupertino, CA (US); Vahid Saadat, Saratoga, CA (US); Ruey-Feng Peh, Mountain View, CA (US); Edmund Tam, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 525 days.

(21) Appl. No.: 14/843,475

(22) Filed: Sep. 2, 2015

(65) Prior Publication Data
US 2015/0366440 A1    Dec. 24, 2015

Related U.S. Application Data

(63) Continuation of application No. 12/108,812, filed on Apr. 24, 2008, now Pat. No. 9,155,452.
(Continued)

(51) Int. Cl.
*A61B 1/00* (2006.01)
*A61B 1/005* (2006.01)
(Continued)

(52) U.S. Cl.
CPC ........ *A61B 1/0008* (2013.01); *A61B 1/00082* (2013.01); *A61B 1/00085* (2013.01);
(Continued)

(58) Field of Classification Search
CPC ..... A61B 1/005; A61B 1/0051; A61B 1/0052; A61B 1/0053; A61B 1/0055;
(Continued)

(56) References Cited

U.S. PATENT DOCUMENTS

| | | | |
|---|---|---|---|
| 623,022 | A | 4/1899 | Johnson |
| 2,305,462 | A | 12/1942 | Wolf |

(Continued)

FOREIGN PATENT DOCUMENTS

| | | | |
|---|---|---|---|
| DE | 10028155 | A | 12/2000 |
| EP | 0283661 | A2 | 9/1988 |

(Continued)

OTHER PUBLICATIONS

Amendment and Response mailed Dec. 14, 2009 for U.S. Appl. No. 11/347,361 filed Feb. 3, 2006.
(Continued)

*Primary Examiner* — Ryan N Henderson
(74) *Attorney, Agent, or Firm* — Haynes & Boone, LLP.

(57) ABSTRACT

A medical manipulation assembly comprises a sheath steerable in response to rotational movement of a sheath steering mechanism. The assembly also comprises a catheter extendable through the sheath. The catheter is steerable in response to rotational movement of a catheter steering mechanism. The sheath and catheter are independently steerable. The assembly also comprises a set of control wires. At least one of the sheath or the catheter includes a plurality of lumens with at least two of the plurality of lumens each sized for passage of one of the control wires of the set of control wires. The steerable catheter includes a working channel sized to receive a visualization instrument therethrough.

16 Claims, 50 Drawing Sheets

Related U.S. Application Data

(60) Provisional application No. 60/914,648, filed on Apr. 27, 2007.

(51) Int. Cl.
| | |
|---|---|
| *A61B 1/008* | (2006.01) |
| *A61B 1/01* | (2006.01) |
| *A61B 1/015* | (2006.01) |
| *A61B 1/018* | (2006.01) |
| *A61B 1/04* | (2006.01) |
| *A61B 1/05* | (2006.01) |
| *A61B 5/02* | (2006.01) |
| *A61M 25/01* | (2006.01) |

(52) U.S. Cl.
CPC ...... *A61B 1/00089* (2013.01); *A61B 1/00096* (2013.01); *A61B 1/00154* (2013.01); *A61B 1/0051* (2013.01); *A61B 1/0052* (2013.01); *A61B 1/0057* (2013.01); *A61B 1/008* (2013.01); *A61B 1/01* (2013.01); *A61B 1/015* (2013.01); *A61B 1/018* (2013.01); *A61B 1/042* (2013.01); *A61B 1/05* (2013.01); *A61B 5/02007* (2013.01); *A61M 25/0138* (2013.01); *A61M 25/0147* (2013.01); *A61M 2025/0161* (2013.01)

(58) Field of Classification Search
CPC .............. A61B 1/0056; A61B 1/0057; A61B 1/0058; A61B 1/008; A61B 1/01; A61B 2017/003; A61B 2017/00305; A61B 2017/00309; A61B 2017/00314; A61B 2017/00318; A61B 2017/00323; A61B 2017/00327; A61B 2017/00331; A61M 25/0133; A61M 25/0136; A61M 25/0138; A61M 25/0141; A61M 25/0144; A61M 25/0147; A61M 25/0152; A61M 2025/015; A61M 2025/0161
USPC ................ 600/104, 106, 114–116, 139–142, 600/146–152, 374, 375, 381, 407, 424, 600/433–435, 466, 467, 471, 478, 508, 600/509, 585; 604/104, 264, 507–510, 604/528

See application file for complete search history.

(56) References Cited

U.S. PATENT DOCUMENTS

| | | | |
|---|---|---|---|
| 2,453,862 A | 11/1948 | Salisbury | |
| 3,559,651 A | 2/1971 | Moss | |
| 3,874,388 A | 4/1975 | King et al. | |
| 4,175,545 A | 11/1979 | Termanini | |
| 4,326,529 A | 4/1982 | Doss et al. | |
| 4,445,892 A | 5/1984 | Hussein et al. | |
| 4,470,407 A | 9/1984 | Hussein | |
| 4,517,976 A | 5/1985 | Murakoshi | |
| 4,569,335 A | 2/1986 | Tsuno | |
| 4,576,146 A | 3/1986 | Kawazoe et al. | |
| 4,615,333 A | 10/1986 | Taguchi | |
| 4,619,247 A | 10/1986 | Inoue et al. | |
| 4,676,258 A | 6/1987 | Inokuchi et al. | |
| 4,681,093 A | 7/1987 | Ono et al. | |
| 4,709,698 A | 12/1987 | Johnston et al. | |
| 4,710,192 A | 12/1987 | Liotta et al. | |
| 4,727,418 A | 2/1988 | Kato et al. | |
| 4,784,133 A | 11/1988 | Mackin | |
| 4,848,323 A | 7/1989 | Marijnissen et al. | |
| 4,873,965 A * | 10/1989 | Danieli | ........ A61B 1/0055 600/152 |
| 4,911,148 A | 3/1990 | Sosnowski et al. | |
| 4,914,521 A | 4/1990 | Adair | |
| 4,943,290 A | 7/1990 | Rexroth et al. | |
| 4,950,285 A | 8/1990 | Wilk | |
| 4,957,484 A | 9/1990 | Murtfeldt | |
| 4,961,738 A | 10/1990 | Mackin | |
| 4,976,710 A | 12/1990 | Mackin | |
| 4,991,578 A | 2/1991 | Cohen | |
| 4,994,069 A | 2/1991 | Ritchart et al. | |
| 4,998,916 A | 3/1991 | Hammerslag et al. | |
| 4,998,972 A | 3/1991 | Chin et al. | |
| 5,047,028 A | 9/1991 | Qian | |
| 5,057,106 A | 10/1991 | Kasevich et al. | |
| 5,090,959 A | 2/1992 | Samson et al. | |
| 5,123,428 A | 6/1992 | Schwarz | |
| RE34,002 E | 7/1992 | Adair | |
| 5,156,141 A | 10/1992 | Krebs et al. | |
| 5,171,259 A | 12/1992 | Inoue | |
| 5,259,364 A * | 11/1993 | Bob | ........................ A61B 1/31 600/129 |
| 5,281,238 A | 1/1994 | Chin et al. | |
| 5,282,827 A | 2/1994 | Kensey et al. | |
| 5,308,234 A | 4/1994 | Johnson | |
| 5,313,943 A | 5/1994 | Houser et al. | |
| 5,330,496 A | 7/1994 | Alferness | |
| 5,334,159 A | 8/1994 | Turkel | |
| 5,334,193 A | 8/1994 | Nardella | |
| 5,336,252 A | 8/1994 | Cohen | |
| 5,339,800 A | 8/1994 | Wiita et al. | |
| 5,348,554 A | 9/1994 | Imran et al. | |
| 5,353,792 A | 10/1994 | Lubbers et al. | |
| 5,370,647 A | 12/1994 | Graber et al. | |
| 5,373,840 A | 12/1994 | Knighton | |
| 5,375,612 A | 12/1994 | Cottenceau et al. | |
| 5,385,148 A | 1/1995 | Lesh et al. | |
| 5,391,182 A | 2/1995 | Chin | |
| 5,403,328 A | 4/1995 | Shallman | |
| 5,405,376 A | 4/1995 | Mulier et al. | |
| 5,421,338 A | 6/1995 | Crowley et al. | |
| 5,431,649 A | 7/1995 | Mulier et al. | |
| 5,438,975 A * | 8/1995 | Miyagi | ................ A61B 1/0055 600/141 |
| 5,453,785 A | 9/1995 | Lenhardt et al. | |
| 5,462,521 A | 10/1995 | Brucker et al. | |
| 5,471,515 A | 11/1995 | Fossum et al. | |
| 5,498,230 A | 3/1996 | Adair | |
| 5,505,730 A | 4/1996 | Edwards | |
| 5,515,853 A | 5/1996 | Smith et al. | |
| 5,527,338 A | 6/1996 | Purdy | |
| 5,549,603 A | 8/1996 | Feiring | |
| 5,558,619 A | 9/1996 | Kami et al. | |
| 5,571,088 A | 11/1996 | Lennox et al. | |
| 5,575,756 A | 11/1996 | Karasawa et al. | |
| 5,575,810 A | 11/1996 | Swanson et al. | |
| 5,584,872 A | 12/1996 | LaFontaine et al. | |
| 5,591,119 A | 1/1997 | Adair | |
| 5,593,405 A | 1/1997 | Osypka | |
| 5,593,422 A | 1/1997 | Muijs et al. | |
| 5,593,424 A | 1/1997 | Northrup III | |
| 5,672,153 A | 9/1997 | Lax et al. | |
| 5,676,693 A | 10/1997 | Lafontaine | |
| 5,681,308 A | 10/1997 | Edwards et al. | |
| 5,695,448 A | 12/1997 | Kimura et al. | |
| 5,697,281 A | 12/1997 | Eggers et al. | |
| 5,697,882 A | 12/1997 | Eggers et al. | |
| 5,704,898 A * | 1/1998 | Kokish | ................ A61B 1/0052 600/139 |
| 5,709,224 A | 1/1998 | Behl et al. | |
| 5,713,907 A | 2/1998 | Hogendijk et al. | |
| 5,713,946 A | 2/1998 | Ben-Haim | |
| 5,716,321 A | 2/1998 | Kerin et al. | |
| 5,722,403 A | 3/1998 | Mcgee et al. | |
| 5,726,523 A | 3/1998 | Mueller | |
| 5,746,747 A | 5/1998 | Mckeating | |
| 5,749,846 A | 5/1998 | Edwards et al. | |
| 5,749,890 A | 5/1998 | Shaknovich | |
| 5,754,313 A | 5/1998 | Pelchy et al. | |
| 5,766,137 A | 6/1998 | Omata | |
| 5,769,846 A | 6/1998 | Edwards et al. | |
| 5,792,045 A | 8/1998 | Adair | |
| 5,797,903 A | 8/1998 | Swanson et al. | |

(56) References Cited

U.S. PATENT DOCUMENTS

| | | |
|---|---|---|
| 5,823,947 A | 10/1998 | Yoon et al. |
| 5,827,268 A | 10/1998 | Laufer |
| 5,829,447 A | 11/1998 | Stevens et al. |
| 5,842,973 A | 12/1998 | Bullard |
| 5,843,118 A | 12/1998 | Sepetka et al. |
| 5,848,969 A | 12/1998 | Panescu et al. |
| 5,860,974 A | 1/1999 | Abele |
| 5,860,991 A | 1/1999 | Klein et al. |
| 5,865,791 A | 2/1999 | Whayne et al. |
| 5,873,815 A | 2/1999 | Kerin et al. |
| 5,879,366 A | 3/1999 | Shaw et al. |
| 5,895,417 A | 4/1999 | Pomeranz et al. |
| 5,897,487 A | 4/1999 | Ouchi |
| 5,897,553 A | 4/1999 | Mulier et al. |
| 5,902,328 A | 5/1999 | Lafontaine et al. |
| 5,904,651 A | 5/1999 | Swanson et al. |
| 5,908,445 A | 6/1999 | Whayne et al. |
| 5,925,038 A | 7/1999 | Panescu et al. |
| 5,928,250 A | 7/1999 | Koike et al. |
| 5,929,901 A | 7/1999 | Adair et al. |
| 5,941,845 A | 8/1999 | Tu et al. |
| 5,944,690 A | 8/1999 | Falwell et al. |
| 5,964,755 A | 10/1999 | Edwards |
| 5,968,053 A | 10/1999 | Revelas |
| 5,971,983 A | 10/1999 | Lesh |
| 5,986,693 A | 11/1999 | Adair et al. |
| 5,997,571 A | 12/1999 | Farr et al. |
| 6,004,269 A | 12/1999 | Crowley et al. |
| 6,012,457 A | 1/2000 | Lesh |
| 6,024,740 A | 2/2000 | Lesh et al. |
| 6,027,501 A | 2/2000 | Goble et al. |
| 6,036,685 A | 3/2000 | Mueller |
| 6,043,839 A | 3/2000 | Adair et al. |
| 6,047,218 A | 4/2000 | Whayne et al. |
| 6,063,077 A | 5/2000 | Schaer |
| 6,063,081 A | 5/2000 | Mulier et al. |
| 6,068,653 A | 5/2000 | Lafontaine |
| 6,071,279 A | 6/2000 | Whayne et al. |
| 6,071,302 A | 6/2000 | Sinofsky et al. |
| 6,081,740 A | 6/2000 | Gombrich et al. |
| 6,083,152 A * | 7/2000 | Strong ................. A61B 1/0055 600/140 |
| 6,086,528 A | 7/2000 | Adair |
| 6,086,534 A | 7/2000 | Kesten |
| 6,099,498 A | 8/2000 | Addis |
| 6,099,514 A | 8/2000 | Sharkey et al. |
| 6,102,905 A | 8/2000 | Baxter et al. |
| 6,112,123 A | 8/2000 | Kelleher et al. |
| 6,115,626 A | 9/2000 | Whayne et al. |
| 6,123,703 A | 9/2000 | Tu et al. |
| 6,123,718 A | 9/2000 | Tu et al. |
| 6,129,724 A | 10/2000 | Fleischman et al. |
| 6,139,508 A | 10/2000 | Simpson et al. |
| 6,142,993 A | 11/2000 | Whayne et al. |
| 6,152,144 A | 11/2000 | Lesh et al. |
| 6,156,350 A | 12/2000 | Constantz |
| 6,159,203 A | 12/2000 | Sinofsky |
| 6,161,543 A | 12/2000 | Cox et al. |
| 6,164,283 A | 12/2000 | Lesh |
| 6,167,297 A | 12/2000 | Benaron |
| 6,168,591 B1 | 1/2001 | Sinofsky |
| 6,168,594 B1 | 1/2001 | Lafontaine et al. |
| 6,174,307 B1 | 1/2001 | Daniel et al. |
| 6,178,346 B1 | 1/2001 | Amundson et al. |
| 6,190,381 B1 | 2/2001 | Olsen et al. |
| 6,211,904 B1 | 4/2001 | Adair et al. |
| 6,224,553 B1 | 5/2001 | Nevo |
| 6,231,561 B1 | 5/2001 | Frazier et al. |
| 6,235,044 B1 | 5/2001 | Root et al. |
| 6,237,605 B1 | 5/2001 | Vaska et al. |
| 6,238,393 B1 | 5/2001 | Mulier et al. |
| 6,240,312 B1 | 5/2001 | Alfano et al. |
| 6,254,598 B1 | 7/2001 | Edwards et al. |
| 6,258,083 B1 | 7/2001 | Daniel et al. |
| 6,263,224 B1 | 7/2001 | West |
| 6,270,492 B1 | 8/2001 | Sinofsky |
| 6,275,255 B1 | 8/2001 | Adair et al. |
| 6,290,689 B1 | 8/2001 | Delaney et al. |
| 6,306,081 B1 | 10/2001 | Ishikawa et al. |
| 6,310,642 B1 | 10/2001 | Adair et al. |
| 6,311,692 B1 | 11/2001 | Vaska et al. |
| 6,314,962 B1 | 11/2001 | Vaska et al. |
| 6,314,963 B1 | 11/2001 | Vaska et al. |
| 6,315,777 B1 | 11/2001 | Comben |
| 6,315,778 B1 | 11/2001 | Gambale et al. |
| 6,322,536 B1 | 11/2001 | Rosengart et al. |
| 6,325,797 B1 | 12/2001 | Stewart et al. |
| 6,328,727 B1 | 12/2001 | Frazier et al. |
| 6,358,247 B1 | 3/2002 | Altman et al. |
| 6,358,248 B1 | 3/2002 | Mulier et al. |
| 6,375,654 B1 | 4/2002 | Mcintyre |
| 6,379,346 B1 | 4/2002 | Constantz |
| 6,394,096 B1 | 5/2002 | Constantz |
| 6,396,873 B1 | 5/2002 | Goldstein et al. |
| 6,385,476 B1 | 6/2002 | Osadchy et al. |
| 6,387,043 B1 | 6/2002 | Yoon |
| 6,387,071 B1 | 6/2002 | Constantz |
| 6,398,780 B1 | 6/2002 | Farley et al. |
| 6,401,719 B1 | 6/2002 | Farley et al. |
| 6,409,722 B1 | 6/2002 | Hoey et al. |
| 6,416,511 B1 | 7/2002 | Lesh et al. |
| 6,419,669 B1 | 7/2002 | Frazier et al. |
| 6,423,051 B1 | 7/2002 | Kaplan et al. |
| 6,423,055 B1 | 7/2002 | Farr et al. |
| 6,423,058 B1 | 7/2002 | Edwards et al. |
| 6,428,536 B2 | 8/2002 | Panescu et al. |
| 6,436,117 B1 * | 8/2002 | Waller ........... A61B 17/320016 606/171 |
| 6,436,118 B1 | 8/2002 | Kayan |
| 6,440,061 B1 | 8/2002 | Wenner et al. |
| 6,440,119 B1 | 8/2002 | Nakada et al. |
| 6,458,076 B1 * | 10/2002 | Pruitt .................. A61B 1/0051 600/128 |
| 6,458,151 B1 | 10/2002 | Saltiel |
| 6,464,697 B1 | 10/2002 | Edwards et al. |
| 6,474,340 B1 | 11/2002 | Vaska et al. |
| 6,475,223 B1 | 11/2002 | Werp et al. |
| 6,478,769 B1 | 11/2002 | Parker |
| 6,482,162 B1 | 11/2002 | Moore |
| 6,484,727 B1 | 11/2002 | Vaska et al. |
| 6,485,489 B2 | 11/2002 | Teirstein et al. |
| 6,488,671 B1 | 12/2002 | Constantz et al. |
| 6,494,902 B2 | 12/2002 | Hoey et al. |
| 6,497,705 B2 | 12/2002 | Comben |
| 6,500,174 B1 | 12/2002 | Maguire et al. |
| 6,502,576 B1 | 1/2003 | Lesh |
| 6,514,249 B1 | 2/2003 | Maguire et al. |
| 6,517,533 B1 | 2/2003 | Swaminathan |
| 6,527,979 B2 | 3/2003 | Constantz et al. |
| 6,532,380 B1 | 3/2003 | Close et al. |
| 6,533,767 B2 | 3/2003 | Johansson et al. |
| 6,537,272 B2 | 3/2003 | Christopherson et al. |
| 6,540,733 B2 | 4/2003 | Constantz et al. |
| 6,540,744 B2 | 4/2003 | Hassett et al. |
| 6,544,195 B2 | 4/2003 | Wilson et al. |
| 6,547,780 B1 | 4/2003 | Sinofsky |
| 6,558,375 B1 | 5/2003 | Sinofsky et al. |
| 6,558,382 B2 | 5/2003 | Jahns et al. |
| 6,562,020 B1 | 5/2003 | Constantz et al. |
| 6,572,609 B1 | 6/2003 | Farr et al. |
| 6,579,285 B2 | 6/2003 | Sinofsky |
| 6,585,732 B2 | 7/2003 | Mulier et al. |
| 6,587,709 B2 | 7/2003 | Solf et al. |
| 6,593,884 B1 | 7/2003 | Gilboa et al. |
| 6,605,055 B1 | 8/2003 | Sinofsky et al. |
| 6,613,062 B1 | 9/2003 | Leckrone et al. |
| 6,622,732 B2 | 9/2003 | Constantz |
| 6,626,855 B1 | 9/2003 | Weng et al. |
| 6,626,900 B1 | 9/2003 | Sinofsky et al. |
| 6,635,070 B2 | 10/2003 | Leeflang et al. |
| 6,645,202 B1 | 11/2003 | Pless et al. |
| 6,650,923 B1 | 11/2003 | Lesh et al. |
| 6,658,279 B2 | 12/2003 | Swanson et al. |
| 6,659,940 B2 | 12/2003 | Adler |

(56) References Cited

U.S. PATENT DOCUMENTS

| | | |
|---|---|---|
| 6,673,090 B2 | 1/2004 | Root et al. |
| 6,676,656 B2 | 1/2004 | Sinofsky |
| 6,679,836 B2 | 1/2004 | Couvillon, Jr. et al. |
| 6,682,526 B1 | 1/2004 | Jones et al. |
| 6,689,128 B2 | 2/2004 | Sliwa et al. |
| 6,692,430 B2 | 2/2004 | Adler |
| 6,701,581 B2 | 3/2004 | Senovich et al. |
| 6,701,931 B2 | 3/2004 | Sliwa et al. |
| 6,702,780 B1 | 3/2004 | Gilboa et al. |
| 6,704,043 B2 | 3/2004 | Goldstein et al. |
| 6,706,039 B2 | 3/2004 | Mulier et al. |
| 6,712,798 B2 | 3/2004 | Constantz |
| 6,719,747 B2 | 4/2004 | Constantz et al. |
| 6,719,755 B2 | 4/2004 | Sliwa et al. |
| 6,730,063 B2 | 5/2004 | Delaney et al. |
| 6,736,810 B2 | 5/2004 | Hoey et al. |
| 6,751,492 B2 | 6/2004 | Ben-Haim |
| 6,755,790 B2 | 6/2004 | Stewart et al. |
| 6,755,811 B1 | 6/2004 | Constantz |
| 6,764,487 B2 | 7/2004 | Mulier et al. |
| 6,771,996 B2 | 8/2004 | Bowe et al. |
| 6,773,402 B2 | 8/2004 | Govari et al. |
| 6,780,151 B2 | 8/2004 | Grabover et al. |
| 6,805,128 B1 | 10/2004 | Pless et al. |
| 6,805,129 B1 | 10/2004 | Pless et al. |
| 6,808,491 B2 * | 10/2004 | Kortenbach ............ A61B 10/06 600/153 |
| 6,811,562 B1 | 11/2004 | Pless |
| 6,833,814 B2 | 12/2004 | Gilboa et al. |
| 6,840,923 B1 | 1/2005 | Lapcevic |
| 6,840,936 B2 | 1/2005 | Sliwa et al. |
| 6,849,073 B2 | 2/2005 | Hoey et al. |
| 6,858,005 B2 | 2/2005 | Ohline et al. |
| 6,858,026 B2 | 2/2005 | Sliwa et al. |
| 6,863,668 B2 | 3/2005 | Gillespie et al. |
| 6,866,651 B2 | 3/2005 | Constantz |
| 6,887,237 B2 | 5/2005 | Mcgaffigan |
| 6,892,091 B1 | 5/2005 | Ben-Haim et al. |
| 6,896,690 B1 | 5/2005 | Lambrecht et al. |
| 6,899,672 B2 | 5/2005 | Chin et al. |
| 6,915,154 B1 | 7/2005 | Docherty et al. |
| 6,916,284 B2 | 7/2005 | Moriyama |
| 6,923,805 B1 | 8/2005 | LaFontaine et al. |
| 6,929,010 B2 | 8/2005 | Vaska et al. |
| 6,932,809 B2 | 8/2005 | Sinofsky |
| 6,939,348 B2 | 9/2005 | Malecki et al. |
| 6,942,657 B2 | 9/2005 | Sinofsky et al. |
| 6,949,095 B2 | 9/2005 | Vaska et al. |
| 6,953,457 B2 | 10/2005 | Farr et al. |
| 6,955,173 B2 | 10/2005 | Lesh |
| 6,962,589 B2 | 11/2005 | Mulier et al. |
| 6,971,394 B2 | 12/2005 | Sliwa et al. |
| 6,974,464 B2 | 12/2005 | Quijano et al. |
| 6,979,290 B2 | 12/2005 | Mourlas et al. |
| 6,982,740 B2 | 1/2006 | Adair et al. |
| 6,984,232 B2 | 1/2006 | Vanney et al. |
| 6,994,094 B2 | 2/2006 | Schwartz |
| 7,019,610 B2 | 3/2006 | Creighton et al. |
| 7,025,746 B2 | 4/2006 | Tal |
| 7,030,904 B2 | 4/2006 | Adair et al. |
| 7,041,098 B2 | 5/2006 | Farley et al. |
| 7,042,487 B2 | 5/2006 | Nakashima |
| 7,044,136 B2 | 5/2006 | Lee |
| 7,052,493 B2 | 5/2006 | Vaska et al. |
| 7,090,683 B2 | 8/2006 | Brock et al. |
| 7,118,566 B2 | 10/2006 | Jahns |
| 7,156,845 B2 | 1/2007 | Mulier et al. |
| 7,163,534 B2 | 1/2007 | Brucker et al. |
| 7,166,537 B2 | 1/2007 | Jacobsen et al. |
| 7,169,144 B2 | 1/2007 | Hoey et al. |
| 7,186,214 B2 | 3/2007 | Ness |
| 7,207,984 B2 | 4/2007 | Farr et al. |
| 7,217,268 B2 | 5/2007 | Eggers et al. |
| 7,242,832 B2 | 7/2007 | Carlin et al. |
| 7,247,155 B2 | 7/2007 | Hoey et al. |
| 7,261,711 B2 | 8/2007 | Mulier et al. |
| 7,263,397 B2 | 8/2007 | Hauck et al. |
| 7,276,061 B2 | 10/2007 | Schaer et al. |
| 7,309,328 B2 | 12/2007 | Kaplan et al. |
| 7,323,001 B2 | 1/2008 | Clubb et al. |
| 7,416,552 B2 | 8/2008 | Paul et al. |
| 7,435,248 B2 | 10/2008 | Taimisto et al. |
| 7,527,625 B2 | 5/2009 | Knight et al. |
| 7,534,204 B2 | 5/2009 | Starksen et al. |
| 7,569,052 B2 | 8/2009 | Phan et al. |
| 7,736,347 B2 | 6/2010 | Kaplan et al. |
| 7,758,499 B2 | 7/2010 | Adler |
| 7,860,556 B2 | 12/2010 | Saadat |
| 7,955,253 B2 * | 6/2011 | Ewers ................ A61B 1/00082 600/114 |
| 8,002,698 B2 * | 8/2011 | Motai .................. A61B 1/2736 600/116 |
| 8,131,350 B2 | 3/2012 | Saadat et al. |
| 8,137,333 B2 | 3/2012 | Saadat et al. |
| 8,206,287 B2 * | 6/2012 | Matsuo ................ A61B 1/0055 600/141 |
| 8,235,985 B2 | 8/2012 | Saadat et al. |
| 8,439,828 B2 * | 5/2013 | Dejima .................. A61B 1/018 600/114 |
| 9,155,452 B2 | 10/2015 | Rothe et al. |
| 11,229,351 B2 * | 1/2022 | Lang ................ A61M 25/0147 |
| 2001/0020126 A1 | 9/2001 | Swanson et al. |
| 2001/0039416 A1 | 11/2001 | Moorman et al. |
| 2001/0047136 A1 | 11/2001 | Domanik et al. |
| 2001/0047184 A1 | 11/2001 | Connors |
| 2002/0004644 A1 | 1/2002 | Koblish |
| 2002/0026145 A1 | 2/2002 | Bagaoisan et al. |
| 2002/0054852 A1 | 5/2002 | Cate |
| 2002/0062063 A1 * | 5/2002 | Ogura .................. A61B 1/0051 600/148 |
| 2002/0065455 A1 | 5/2002 | Ben-Haim et al. |
| 2002/0087169 A1 | 7/2002 | Brock et al. |
| 2002/0091304 A1 | 7/2002 | Ogura et al. |
| 2002/0138088 A1 | 9/2002 | Nash et al. |
| 2002/0165598 A1 | 11/2002 | Wahr et al. |
| 2002/0169377 A1 | 11/2002 | Khairkhahan et al. |
| 2003/0009085 A1 | 1/2003 | Arai et al. |
| 2003/0035156 A1 | 2/2003 | Cooper |
| 2003/0036698 A1 | 2/2003 | Kohler et al. |
| 2003/0040657 A1 * | 2/2003 | Yamaya ............. A61B 1/00039 600/107 |
| 2003/0069593 A1 | 4/2003 | Tremulis et al. |
| 2003/0083550 A1 * | 5/2003 | Miyagi ................ A61B 1/0055 600/141 |
| 2003/0120142 A1 | 6/2003 | Dubuc et al. |
| 2003/0130572 A1 | 7/2003 | Phan et al. |
| 2003/0144657 A1 | 7/2003 | Bowe et al. |
| 2003/0171741 A1 | 9/2003 | Ziebol et al. |
| 2003/0181939 A1 | 9/2003 | Bonutti |
| 2003/0208222 A1 | 11/2003 | Zadno-Azizi |
| 2003/0212394 A1 | 11/2003 | Pearson et al. |
| 2003/0220574 A1 | 11/2003 | Markus et al. |
| 2003/0222325 A1 | 12/2003 | Jacobsen et al. |
| 2004/0049211 A1 | 3/2004 | Tremulis et al. |
| 2004/0054335 A1 | 3/2004 | Lesh et al. |
| 2004/0054389 A1 | 3/2004 | Osypka |
| 2004/0082833 A1 | 4/2004 | Adler et al. |
| 2004/0097788 A1 * | 5/2004 | Mourlas ............. A61B 1/00082 600/116 |
| 2004/0098031 A1 | 5/2004 | Van Der Burg et al. |
| 2004/0117032 A1 | 6/2004 | Roth |
| 2004/0133113 A1 | 7/2004 | Krishnan |
| 2004/0138525 A1 * | 7/2004 | Saadat ................ A61B 1/0055 600/104 |
| 2004/0138707 A1 | 7/2004 | Greenhalgh |
| 2004/0147806 A1 | 7/2004 | Adler |
| 2004/0147911 A1 | 7/2004 | Sinofsky |
| 2004/0147912 A1 | 7/2004 | Sinofsky |
| 2004/0147913 A1 | 7/2004 | Sinofsky |
| 2004/0158143 A1 | 8/2004 | Flaherty et al. |
| 2004/0158289 A1 | 8/2004 | Girouard et al. |
| 2004/0167503 A1 | 8/2004 | Sinofsky |
| 2004/0181237 A1 | 9/2004 | Forde et al. |

(56) References Cited

U.S. PATENT DOCUMENTS

| | | |
|---|---|---|
| 2004/0186349 A1* | 9/2004 | Ewers ................... A61B 1/31 600/114 |
| 2004/0199052 A1 | 10/2004 | Banik et al. |
| 2004/0210239 A1 | 10/2004 | Nash et al. |
| 2004/0215180 A1 | 10/2004 | Starkebaum |
| 2004/0220471 A1 | 11/2004 | Schwartz |
| 2004/0230131 A1 | 11/2004 | Kassab et al. |
| 2004/0248837 A1 | 12/2004 | Raz et al. |
| 2004/0249367 A1 | 12/2004 | Saadat et al. |
| 2004/0254523 A1 | 12/2004 | Fitzgerald et al. |
| 2004/0260182 A1 | 12/2004 | Zuluaga et al. |
| 2005/0014995 A1 | 1/2005 | Amundson et al. |
| 2005/0015048 A1 | 1/2005 | Chiu et al. |
| 2005/0020814 A1 | 1/2005 | Amundson et al. |
| 2005/0027163 A1 | 2/2005 | Chin et al. |
| 2005/0038419 A9 | 2/2005 | Arnold et al. |
| 2005/0059862 A1 | 3/2005 | Phan |
| 2005/0059954 A1 | 3/2005 | Constantz |
| 2005/0059965 A1 | 3/2005 | Eberl et al. |
| 2005/0065504 A1 | 3/2005 | Melsky et al. |
| 2005/0090709 A1* | 4/2005 | Okada ................... A61B 17/072 600/153 |
| 2005/0090818 A1 | 4/2005 | Pike, Jr. et al. |
| 2005/0096643 A1 | 5/2005 | Brucker et al. |
| 2005/0101984 A1 | 5/2005 | Chanduszko et al. |
| 2005/0107736 A1 | 5/2005 | Landman et al. |
| 2005/0124969 A1 | 6/2005 | Fitzgerald et al. |
| 2005/0131401 A1 | 6/2005 | Malecki et al. |
| 2005/0154252 A1 | 7/2005 | Sharkey et al. |
| 2005/0159702 A1 | 7/2005 | Sekiguchi et al. |
| 2005/0165279 A1 | 7/2005 | Adler et al. |
| 2005/0165391 A1 | 7/2005 | Maguire et al. |
| 2005/0165466 A1 | 7/2005 | Morris et al. |
| 2005/0171400 A1* | 8/2005 | Itoi ................... A61B 1/00082 600/116 |
| 2005/0197530 A1 | 9/2005 | Wallace et al. |
| 2005/0197623 A1 | 9/2005 | Leeflang et al. |
| 2005/0215895 A1 | 9/2005 | Popp et al. |
| 2005/0222557 A1 | 10/2005 | Baxter et al. |
| 2005/0222558 A1 | 10/2005 | Baxter et al. |
| 2005/0228452 A1 | 10/2005 | Mourlas et al. |
| 2005/0234294 A1* | 10/2005 | Saadat ................ A61B 1/00193 600/104 |
| 2005/0234436 A1 | 10/2005 | Baxter et al. |
| 2005/0234437 A1 | 10/2005 | Baxter et al. |
| 2005/0267328 A1 | 12/2005 | Blumzvig et al. |
| 2005/0272971 A1* | 12/2005 | Ohnishi ............. A61B 1/00009 600/101 |
| 2005/0272975 A1* | 12/2005 | McWeeney ........ A61B 1/00071 600/113 |
| 2005/0272977 A1* | 12/2005 | Saadat ............... A61B 1/00183 600/114 |
| 2005/0277945 A1* | 12/2005 | Saadat ............. A61B 17/06166 606/108 |
| 2006/0009715 A1 | 1/2006 | Khairkhahan et al. |
| 2006/0009737 A1 | 1/2006 | Whiting et al. |
| 2006/0015096 A1 | 1/2006 | Hauck et al. |
| 2006/0022234 A1 | 2/2006 | Adair et al. |
| 2006/0025651 A1 | 2/2006 | Adler et al. |
| 2006/0025787 A1 | 2/2006 | Morales et al. |
| 2006/0069303 A1 | 3/2006 | Couvillon, Jr. |
| 2006/0074398 A1 | 4/2006 | Whiting et al. |
| 2006/0084839 A1 | 4/2006 | Mourlas et al. |
| 2006/0084945 A1 | 4/2006 | Moll et al. |
| 2006/0089637 A1 | 4/2006 | Werneth et al. |
| 2006/0100480 A1* | 5/2006 | Ewers ................ A61B 1/00082 600/114 |
| 2006/0111614 A1 | 5/2006 | Saadat et al. |
| 2006/0122587 A1 | 6/2006 | Sharareh |
| 2006/0146172 A1 | 7/2006 | Jacobsen et al. |
| 2006/0149331 A1 | 7/2006 | Mann et al. |
| 2006/0155242 A1 | 7/2006 | Constantz |
| 2006/0161133 A1 | 7/2006 | Laird et al. |
| 2006/0167439 A1 | 7/2006 | Kalser et al. |
| 2006/0183992 A1 | 8/2006 | Kawashima |
| 2006/0217758 A1 | 9/2006 | Eversull |
| 2006/0224167 A1 | 10/2006 | Weisenburgh et al. |
| 2006/0025890 A1 | 11/2006 | Saadat et al. |
| 2006/0253113 A1 | 11/2006 | Arnold et al. |
| 2006/0271032 A1 | 11/2006 | Chin et al. |
| 2007/0005019 A1 | 1/2007 | Okishige |
| 2007/0015964 A1 | 1/2007 | Eversull et al. |
| 2007/0016130 A1 | 1/2007 | Leeflang et al. |
| 2007/0043338 A1* | 2/2007 | Moll ................... A61B 17/062 606/1 |
| 2007/0043413 A1 | 2/2007 | Eversull et al. |
| 2007/0049923 A1 | 3/2007 | Jahns |
| 2007/0055142 A1 | 3/2007 | Webler |
| 2007/0078451 A1 | 4/2007 | Arnold et al. |
| 2007/0083187 A1 | 4/2007 | Eversull et al. |
| 2007/0083217 A1 | 4/2007 | Eversull et al. |
| 2007/0093808 A1 | 4/2007 | Mulier et al. |
| 2007/0100324 A1 | 5/2007 | Tempel et al. |
| 2007/0106146 A1 | 5/2007 | Altmann et al. |
| 2007/0106214 A1 | 5/2007 | Gray et al. |
| 2007/0106287 A1 | 5/2007 | O'Sullivan |
| 2007/0135826 A1 | 6/2007 | Zaver et al. |
| 2007/0167680 A1* | 7/2007 | Miyamoto ........... A61B 1/0055 600/129 |
| 2007/0167801 A1 | 7/2007 | Webler et al. |
| 2007/0197864 A1* | 8/2007 | Dejima .............. A61B 17/3478 606/186 |
| 2007/0265609 A1 | 11/2007 | Thapliyal et al. |
| 2007/0265610 A1 | 11/2007 | Thapliyal et al. |
| 2007/0270686 A1 | 11/2007 | Ritter et al. |
| 2007/0287886 A1 | 12/2007 | Saadat |
| 2007/0293724 A1 | 12/2007 | Saadat et al. |
| 2008/0009747 A1 | 1/2008 | Saadat et al. |
| 2008/0009859 A1 | 1/2008 | Auth et al. |
| 2008/0015445 A1 | 1/2008 | Saadat et al. |
| 2008/0015563 A1 | 1/2008 | Hoey et al. |
| 2008/0015569 A1 | 1/2008 | Saadat et al. |
| 2008/0027464 A1* | 1/2008 | Moll ..................... A61B 34/30 606/130 |
| 2008/0033241 A1 | 2/2008 | Peh et al. |
| 2008/0051631 A1* | 2/2008 | Dejima ................ A61B 1/0052 600/114 |
| 2008/0057106 A1 | 3/2008 | Erickson et al. |
| 2008/0058590 A1 | 3/2008 | Saadat et al. |
| 2008/0058650 A1 | 3/2008 | Saadat et al. |
| 2008/0058836 A1 | 3/2008 | Moll et al. |
| 2008/0097476 A1 | 4/2008 | Peh et al. |
| 2008/0183081 A1 | 7/2008 | Lys et al. |
| 2008/0188759 A1 | 8/2008 | Saadat et al. |
| 2008/0214889 A1 | 9/2008 | Saadat et al. |
| 2008/0214890 A1* | 9/2008 | Motai .................... A61B 1/018 600/107 |
| 2008/0228032 A1 | 9/2008 | Starksen et al. |
| 2008/0249356 A1* | 10/2008 | Motai ................ A61B 1/00082 600/114 |
| 2008/0269557 A1* | 10/2008 | Marescaux .......... A61B 1/018 600/106 |
| 2008/0281293 A1 | 11/2008 | Peh et al. |
| 2008/0287790 A1 | 11/2008 | Li |
| 2008/0287805 A1 | 11/2008 | Li |
| 2008/0287961 A1* | 11/2008 | Miyamoto .......... A61B 1/00098 606/127 |
| 2008/0306339 A1* | 12/2008 | Hashimoto ........ A61B 17/2909 600/149 |
| 2009/0030276 A1 | 1/2009 | Saadat et al. |
| 2009/0030412 A1 | 1/2009 | Willis et al. |
| 2009/0054803 A1 | 2/2009 | Saadat et al. |
| 2009/0062790 A1 | 3/2009 | Malchano et al. |
| 2009/0076489 A1 | 3/2009 | Welches et al. |
| 2009/0082623 A1 | 3/2009 | Rothe et al. |
| 2009/0125022 A1 | 5/2009 | Saadat et al. |
| 2009/0143640 A1 | 6/2009 | Saadat et al. |
| 2009/0187074 A1 | 7/2009 | Saadat et al. |
| 2009/0203962 A1 | 8/2009 | Miller et al. |
| 2009/0221871 A1 | 9/2009 | Peh et al. |
| 2009/0227999 A1 | 9/2009 | Willis et al. |
| 2009/0264727 A1 | 10/2009 | Markowitz et al. |

(56) References Cited

U.S. PATENT DOCUMENTS

| | | | |
|---|---|---|---|
| 2009/0267773 A1 | 10/2009 | Markowitz et al. | |
| 2009/0275799 A1 | 11/2009 | Saadat et al. | |
| 2009/0299363 A1 | 12/2009 | Saadat et al. | |
| 2009/0326672 A1 | 12/2009 | Peh et al. | |
| 2010/0004506 A1 | 1/2010 | Saadat | |
| 2010/0004633 A1 | 1/2010 | Rothe et al. | |
| 2010/0004661 A1 | 1/2010 | Verin et al. | |
| 2010/0010311 A1 | 1/2010 | Miller et al. | |
| 2010/0094081 A1 | 4/2010 | Rothe et al. | |
| 2010/0130836 A1 | 5/2010 | Malchano et al. | |
| 2011/0006022 A1 | 3/2011 | Saadat | |
| 2011/0060298 A1 | 3/2011 | Saadat | |
| 2011/0144576 A1 | 6/2011 | Rothe et al. | |
| 2011/0301415 A1* | 12/2011 | Motai | A61B 1/00082 600/114 |
| 2012/0016221 A1 | 1/2012 | Saadat et al. | |
| 2012/0059366 A1 | 3/2012 | Drews et al. | |
| 2012/0150046 A1 | 6/2012 | Watson et al. | |
| 2012/0226166 A1 | 9/2012 | Saadat et al. | |

FOREIGN PATENT DOCUMENTS

| | | |
|---|---|---|
| EP | 0301288 A1 | 2/1989 |
| JP | S5993413 A | 5/1984 |
| JP | S59181315 A | 10/1984 |
| JP | H0122113 A | 9/1989 |
| JP | H03284265 A | 12/1991 |
| JP | H05103746 A | 4/1993 |
| JP | H0951897 A | 2/1997 |
| JP | H11299726 A | 11/1999 |
| JP | 2001258822 A | 9/2001 |
| WO | WO-9221292 A2 | 12/1992 |
| WO | WO-9407413 A1 | 4/1994 |
| WO | WO-9503843 A1 | 2/1995 |
| WO | WO-9818388 A1 | 5/1998 |
| WO | WO-03039350 A2 | 6/2003 |
| WO | WO-03053491 A2 | 7/2003 |
| WO | WO-03101287 A | 12/2003 |
| WO | WO-2004043272 A1 | 5/2004 |
| WO | WO2004080508 A2 | 9/2004 |
| WO | WO-2006081202 A1 | 9/2005 |
| WO | WO-2006017617 A2 | 2/2006 |
| WO | WO-2006024015 A1 | 3/2006 |
| WO | WO-2005070330 A | 8/2006 |
| WO | WO-2005077435 A1 | 8/2006 |
| WO | WO-2006081597 A1 | 8/2006 |
| WO | WO-2006083794 A2 | 8/2006 |
| WO | WO-2006126979 A2 | 11/2006 |
| WO | WO-2007067323 A2 | 6/2007 |
| WO | WO-2007079268 A2 | 7/2007 |
| WO | WO-2007133845 A2 | 11/2007 |
| WO | WO-2007134258 A2 | 11/2007 |
| WO | WO-2008016625 A2 | 2/2008 |
| WO | WO-2008021994 A2 | 2/2008 |
| WO | WO-2008021997 A2 | 2/2008 |
| WO | WO-2008021998 A2 | 2/2008 |
| WO | WO-2008024261 A2 | 2/2008 |
| WO | WO-2008079828 A2 | 7/2008 |
| WO | WO-2009112262 A2 | 9/2009 |

OTHER PUBLICATIONS

Avitall B., et al., "Right-Sided Driven Atrial Fibrillation in a Sterile Pericarditis Dog Model," Pacing and Clinical Electrophysiology, 1994, vol. 17, pp. 774.

Avitall, et al. "A Catheter System to Abiate Atrial Fibrillation ina Sterile Pericarditis Dog Model," Pacing and Clinical Electrophysiology, 1994, vol. 17, pp. 774.

Avitall, "Vagally Mediated Atrial Fibrillation in a Dog Model can be Ablated by Placing Linear Radiofrequency Lesions at the Junction of the Right Atrial Appendage and the Superior Vena Cava," Pacing and Clinical Electrophysiology, 1995, vol. 18, pp. 857.

Baker B.M., et al., "Nonpharmacologic Approaches to the Treatment of Atrial Fibrillation and Atrial Flutter," Journal of Cardiovascular Electrophysiology, 1995, vol. 6 (10 Pt 2), pp. 972-978.

Bhakta D., et al., "Principles of Electroanatomic Mapping," Indian Pacing and Electrophysiology Journal, 2008, vol. 8 (1), pp. 32-50.

Bidoggia H., et al., "Transseptal Left Heart Catheterization: Usefulness of the Intracavitary Electrocardiogram in the Localization of the Fossa Ovalis," Cathet Cardiovasc Diagn, 1991, vol. 24 (3), pp. 221-225, PMID: 1764747 [online], [retrieved Feb. 15, 2010], Retrieved from the internet: ⁢URL: http://www.ncbi.nlm.nih.gov/sites/entrez >.

Bredikis J.J., et al., "Surgery of Tachyarrhythia: Intracardiac Closed Heart Cryoablation," Pacing and Clinical Electrophysiology, 1990, vol. 13, (Part 2), pp. 1980-1984.

Communication from the Examining Division for Application No. EP06734083.6 mailed on Nov. 12, 2010, 3 pages.

Communication from the Examining Division for Application No. EP06734083.6 mailed on Oct. 23, 2009, 1 page.

Communication from the Examining Division for Application No. EP08746822.9 mailed on Jul. 13, 2010, 1 page.

Co-pending U.S. Appl. No. 61/286,283, filed Dec. 14, 2009.

Co-pending U.S. Appl. No. 61/297,462, filed Jan. 22, 2010.

Cox J.L., "Cardiac Surgery for Arrhythmias," Journal of Cardiovascular iElectrophsiology, 2004, vol. 15, pp. 250-262.

Cox J.L., et al., "Five-Year Experience With the Maze Procedure for Atrial Fibrillation," The Annals of Thoracic Surgery, 1993, vol. 56, pp. 814-824.

Cox J.L., et al., "Modification of the Maze Procedure for Atrial Flutter and Atrial Fibrillation," The Journal of Thoracic and Cardiovascular Surgery, 1995, vol. 110, pp. 473-484.

Cox J.L., "The Status of Surgery for Cardiac Arrhythmias," Circulation, 1985, vol. 71, pp. 413-417.

Cox J.L., "The Surgical Treatment of Atrial Fibrillation," The Journal of Thoracic and Cardiovascular Surgery, 1991, vol. 101, pp. 584-592.

Elvan A., et al., "Radiofrequency Catheter Ablation of the Atria Reduces Inducibility and Duration of Atrial Fibrillaltion in Dogs," Circulation, vol. 91, 1995, pp. 2235-2244 [online], [retrieved Feb. 4, 2013]. Retrieved from the Internet: &It;URL: http://cir.ahajournals.org/cgi/content/ful/91/8/2235>.

Elvan A., et al., "Radiofrequency Atheter Ablation (RFCA) of the Atria Effectively Abolishes Pacing Induced Chronic Atrial Fibrillation," Pacing and Clinical Electrophysiology, 1996, vol. 18, pp. 856.

Elvan, et al., "Replication of the 'Maze' Procedure by Radiofrequency Catheter Ablation Reduces the Ability to Induce Atrial Fibrillation," Pacing and Clinical Electrophysiology, 1994, vol. 17, pp. 774.

European Search Report for Application No. EP07799466.3 mailed on Nov. 18, 2010, 9 pages.

European Search Report for Application No. EP08746822.9 mailed on Mar. 29, 2010, 7 Pages.

Examination Communication for Application No. EP06734083.6 mailed on May 18, 2010, 3 Pages.

Extended European Search Report for Application No. EP067334083.6 mailed on Jul. 1, 2009, 6 pages.

Fieguth H.G., et al., "Inhibition of Atrial Fibrillation by Pulmonary Vein Isolation and Auricular Resection—Experimental Study in a Sheep Model," The European Journal of Cardio-Thoracic Surgery, 1997, vol. 11, pp. 714-721.

Final Office Action mailed Mar. 1, 2010 for U.S. Appl. No. 12/117,655, filed May 8, 2008.

Final Office Action mailed Jun. 2, 2011 for U.S. Appl. No. 12/117,655, filed May 8, 2008.

Final Office Action mailed May 12, 2011 for U.S. Appl. No. 11/775,771, filed Jul. 10, 2007.

Final Office Action mailed Sep. 16, 2010 for U.S. Appl. No. 11/828,267, filed Jul. 25, 2007.

Hoey M.F., et al., "Intramural Ablation Using Radiofrequency Energy via Screw-Tip Catheter and Saline Electrode," Pacing and Clinical Electrophysiology, 1995, vol. 18, Part II, 487.

Huang, "Increase in the Lesion Size and Decrease in the Impedance Rise with a Saline Infusion Electrode Catheter for Radiofrequency," Circulation, 1989, vol. 80 (4), II-324.

(56) References Cited

OTHER PUBLICATIONS

International Search Report and Written Opinion for Application No. PCT/US2008/061471, mailed on Sep. 11, 2008, 6 pages.
Moser K.M., et al., "Angioscopic Visualization of Pulmonary Emboli," Chest, 1980, vol. 77 (2), pp. 198-201.
Nakamura F., et al., "Percutaneous Intracardiac Surgery With Cardioscopic Guidance," SPIE, 1992, vol. 1642, pp. 214-216.
Non-Final Office Action mailed Jun. 7, 2011 for U.S. Appl. No. 12/323,281, filed Nov. 25, 2008.
Non-Final Ofice Action mailed Jun. 8, 2009 for U.S. Appl. No. 12/117,655, filed May 8, 2008.
Non-Final Office Action mailed May 9, 2011 for U.S. Appl. No. 11/961,950, filed Dec. 20, 2007.
Non-Final Office Action mailed May 9, 2011 for U.S. Appl. No. 11/961,995, filed Dec. 20, 2007.
Non-Final Office Action mailed May 9, 2011 for U.S. Appl. No. 11/962,029, filed Dec. 20, 2007.
Non-Final Office Action mailed Jun. 10, 2010 for U.S. Appl. No. 11/560,742, filed Nov. 16, 2006.
Non-Final Office Action mailed Apr. 11, 2011 for U.S. Appl. No. 11/763,399, filed Jun. 14, 2007.
Non Final Office Action mailed Mar. 11, 2011 for U.S. Appl. No. 11/848,202, filed Aug. 30, 2007.
Non-Final Office Action mailed May 11, 2011 for U.S. Appl. No. 11/828,267, filed Jul. 25, 2007.
Non-Final Office Action mailed Apr. 12, 2011 for U.S. Appl. No. 12/499,011, filed Jul. 7, 2009.
Non-Final Office Action mailed Jan. 14, 2010 for U.S. Appl. No. 11/828,267, filed Jul. 25, 2007.
Non-Final Office Action mailed Dec. 16, 2010 for U.S. Appl. No. 12/117,655, filed May 8, 2008.
Non-Final Office Action mailed Feb. 18, 2011 for U.S. Appl. No. 12/947,198, filed Nov. 16, 2010.
Non-Final Office Action mailed Feb. 18, 2011 for U.S. Appl. No. 12/947,246, filed Nov. 16, 2006.
Non-Final Office Action malled May 20, 2011 for U.S. Appl. No. 11/775,819, filed Jul. 10, 2007.
Non-Final Office Action mailed May 20, 2011 for U.S. Appl. No. 11/877,386, filed Oct. 23, 2007.
Non-Final Office Action mailed Jul. 21, 2010 for U.S. Appl. No. 11/687,597, filed Mar. 16, 2007.
Non-Final Office Action mailed Apr. 22, 2011 for U.S. Appl. No. 12/367,019, filed Feb. 6, 2009.
Non-Final Office Action mailed May 23, 2011 for U.S. Appl. No. 11/775,837, filed Jul. 10, 2007.
Non-Final Office Action mailed Nov. 24, 2010 for U.S. Appl. No. 11/848,429, filed Aug. 31, 2007.
Non-Final Office Action mailed Nov. 24, 2010 for U.S. Appl. No. 12/464,800, filed May 12, 2009.
Non-Final Office Action mailed Apr. 25, 2011 for U.S. Appl. No. 11/959,158, filed Dec. 18, 2007.
Non-Final Office Action mailed Feb. 25, 2010 for U.S. Appl. No. 11/259,498, filed Oct. 25, 2005.
Non-Final Office Action mailed Feb. 25, 2011 for U.S. Appl. No. 11/848,207, filed Aug. 30, 2007.
Non-Final Office Action mailed Apr. 26, 2011 for U.S. Appl. No. 11/848,532, filed Aug. 31, 2007.
Non-Final Office Action mailed Apr. 27, 2011 for U.S. Appl. No. 11/828,28, filed Jul. 25, 2007.
Non Final Office Action mailed Aug. 27, 2010 for U.S. Appl. No. 11/775,771, filed Jul. 10, 2007.
Non-Final Office Action mailed Dec. 27, 2010 for U.S. Appl. No. 12/026,455, filed Feb. 5, 2008.
Notice of Allowance mailed Feb. 3, 2011 for U.S. Appl. No. 11/560,732, filed Nov. 16, 2006.
Notice of Allowance mailed Jun. 13, 2011 for Japanese Application No. 2007-554156 filed Jan. 30, 2006.
Notice of Allowance mailed Nov. 15, 2010 for U.S. Appl. No. 11/259,498, filed Oct. 25, 2005.
Notice of Allowance mailed Nov. 15, 2010 for U.S. Appl. No. 11/560,742, filed Nov. 16, 2006.
Notice of Allowance mailed Feb. 24, 2011 for U.S. Appl. No. 11/560,732, filed Mar. 16, 2007.
Notice of Allowance mailed Feb. 24, 2011 for U.S. Appl. No. 11/687,597, filed Mar. 16, 2007.
Office Action mailed Feb. 15, 2011 for Japanese Application No. 2007-554156 filed Jan. 30, 2006.
Office Action mailed Apr. 27, 2011 for Japanese Application No. 2009-500630 filed Mar. 16, 2007.
Pappone E., et al., "Circumferential Radeiiofrequency Ablation of Pulmonary Vein Ostia," Circulation, 2000, vol. 102, pp. 2619-2628.
Sethi K.K., et al., "Transeptal catheterization for the electrophysiologist modification with a 'view'," Journal of Interventional Cardiac Electrophysiology, 2001, vol. 5 (1), pp. 97-99.
Supplemental European Search Report for Application No. EP07758716 mailed on Feb. 28, 2011, 8 Pages.
Supplementary European search report for Application No. EP07812146.4 mailed on Nov. 18, 2010, 8 Pages.
Supplementary European Search Report for Application No. EP07841754, mailed on Jun. 30, 2010, 6 pages.
Thiagalingam A., et al., "Cooled Needle Catheter Ablation Creates Deeper and Wider Lesions than Irrigated Tip Catheter Ablation," Journal of Cardiovascular Electrophysiology, 2005, vol. 16 (5), pp. 1-8.
Uchida Y., "Developmental History of Cardioscopes", in: Coronary Angioscopy, Chapter 19. Futura Publishing Company, Inc., 2001, pp. 187-197.
Willkampf F.H., et al., "Radiofrequency Ablation with a Cooled Porous Electrode Catheter," JACC, Abstract, 1988, vol. 11 (2), pp. 17A.

* cited by examiner

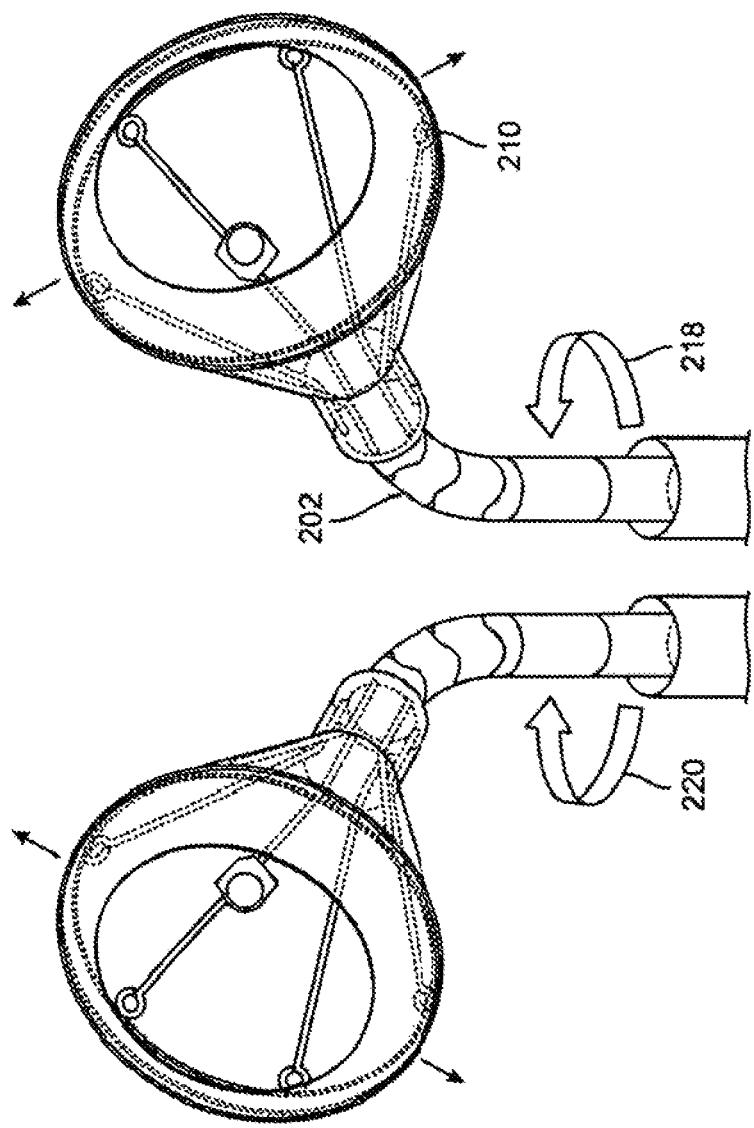

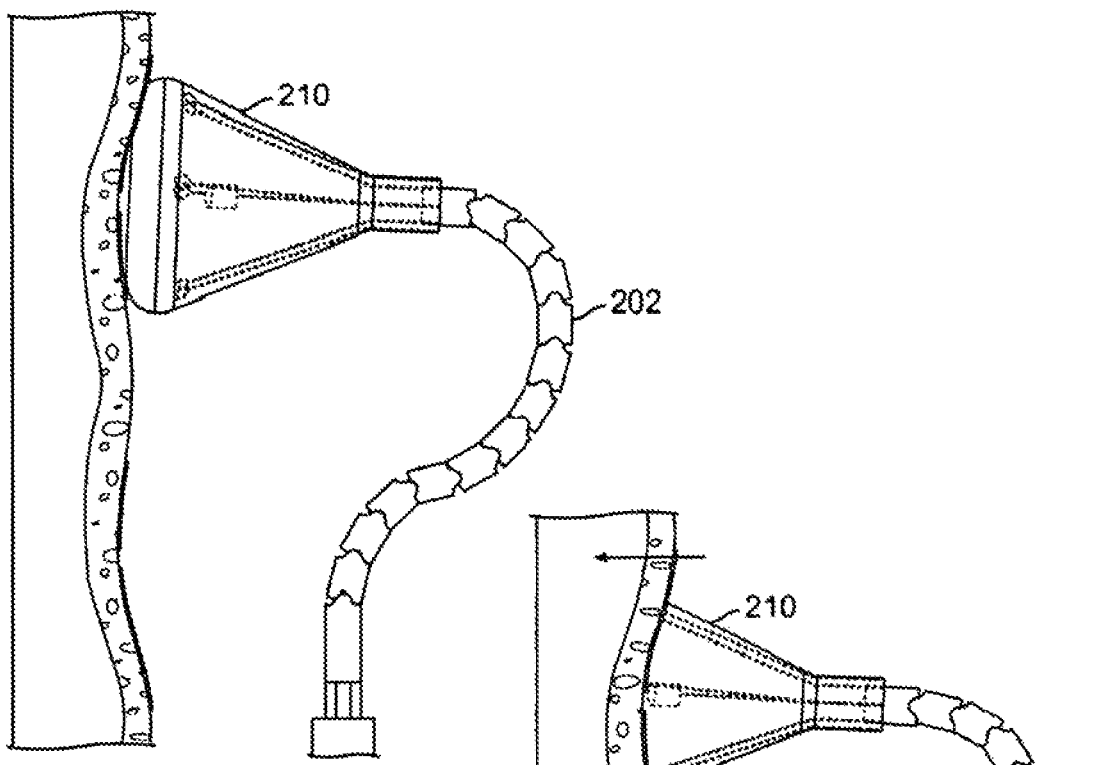
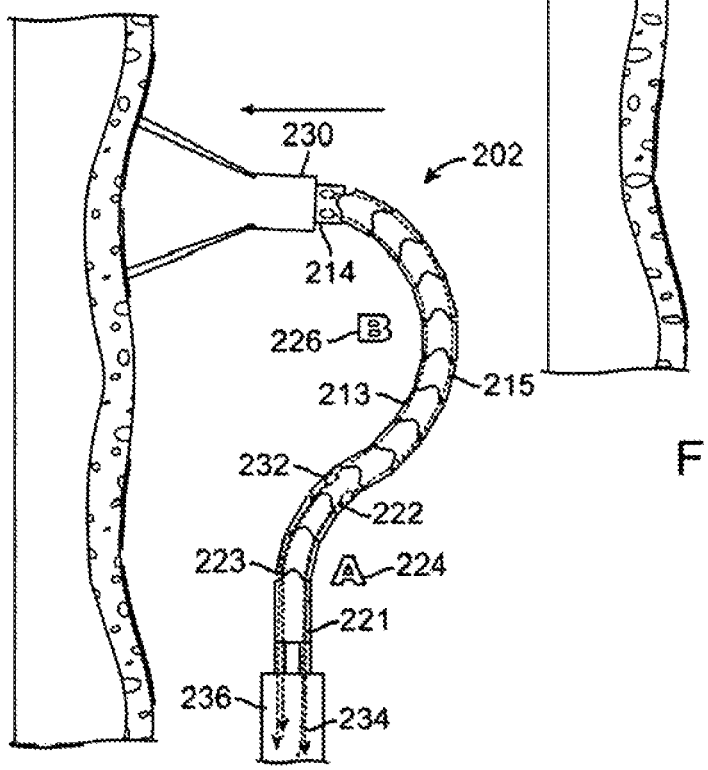
FIG. 13E
FIG. 13F
FIG. 13G

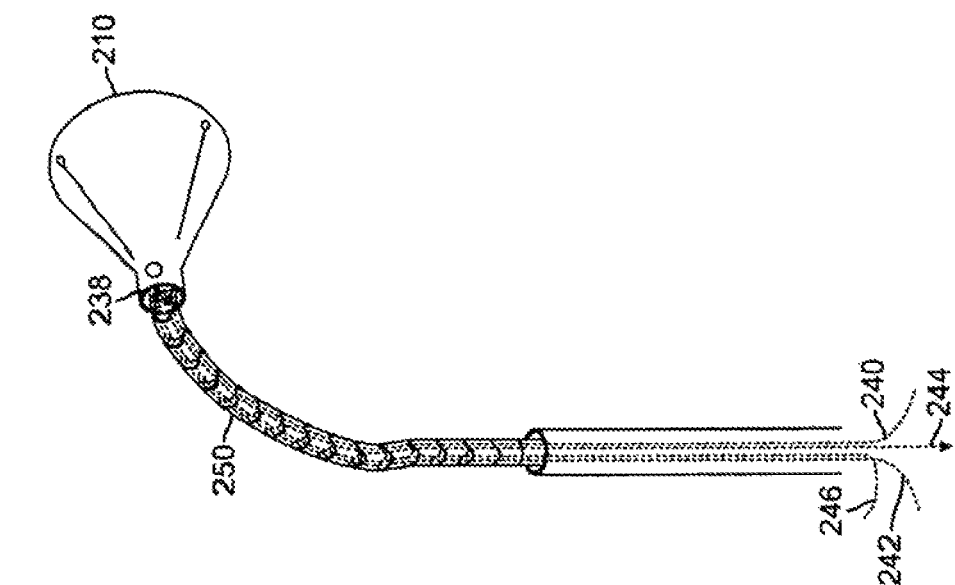
FIG. 14C
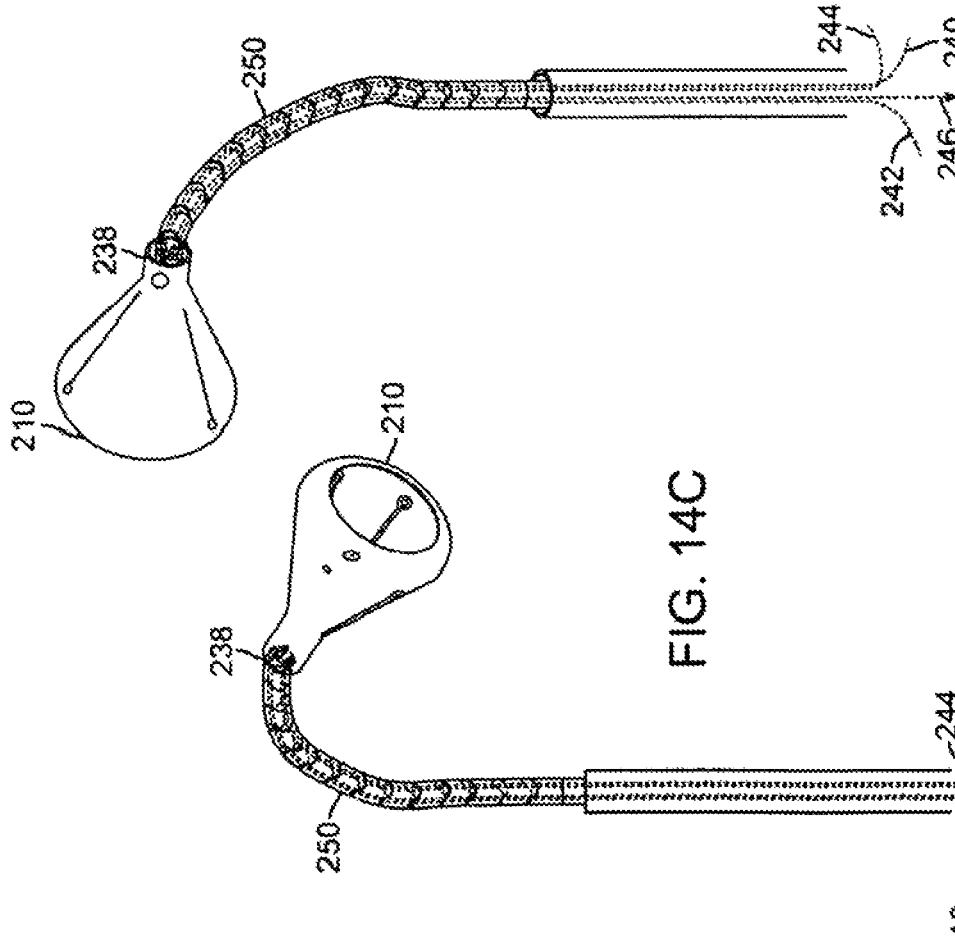
FIG. 14D
FIG. 14E

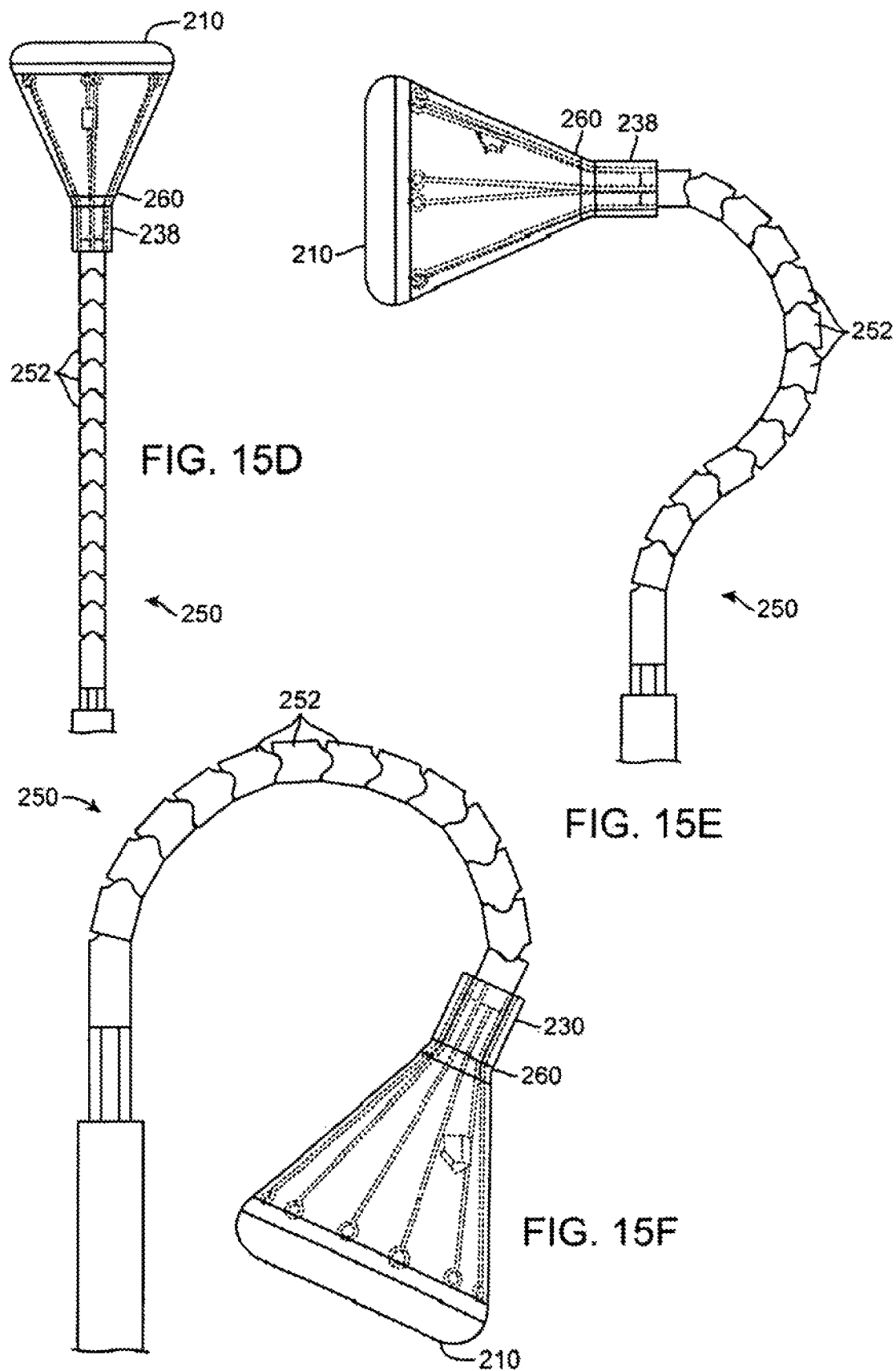

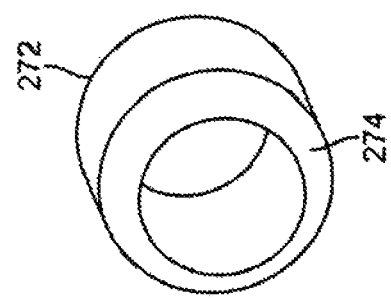
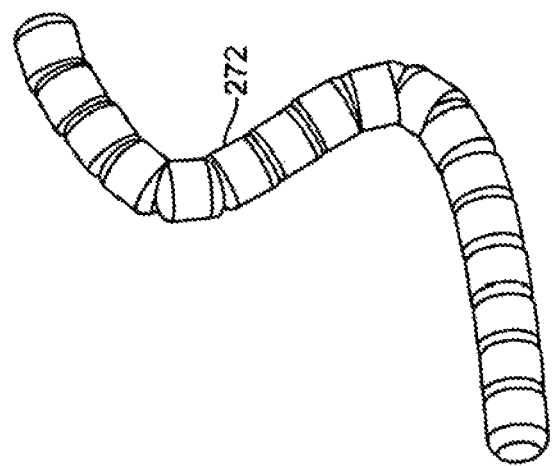
FIG. 17B
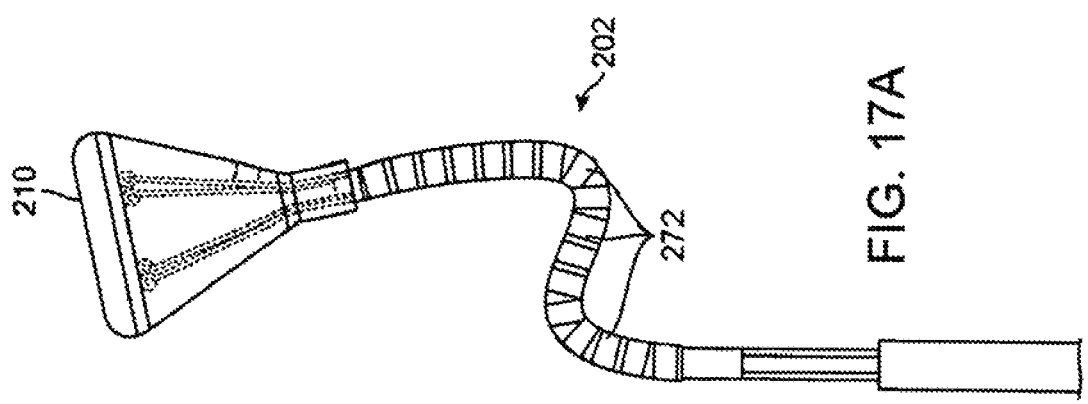
FIG. 17A

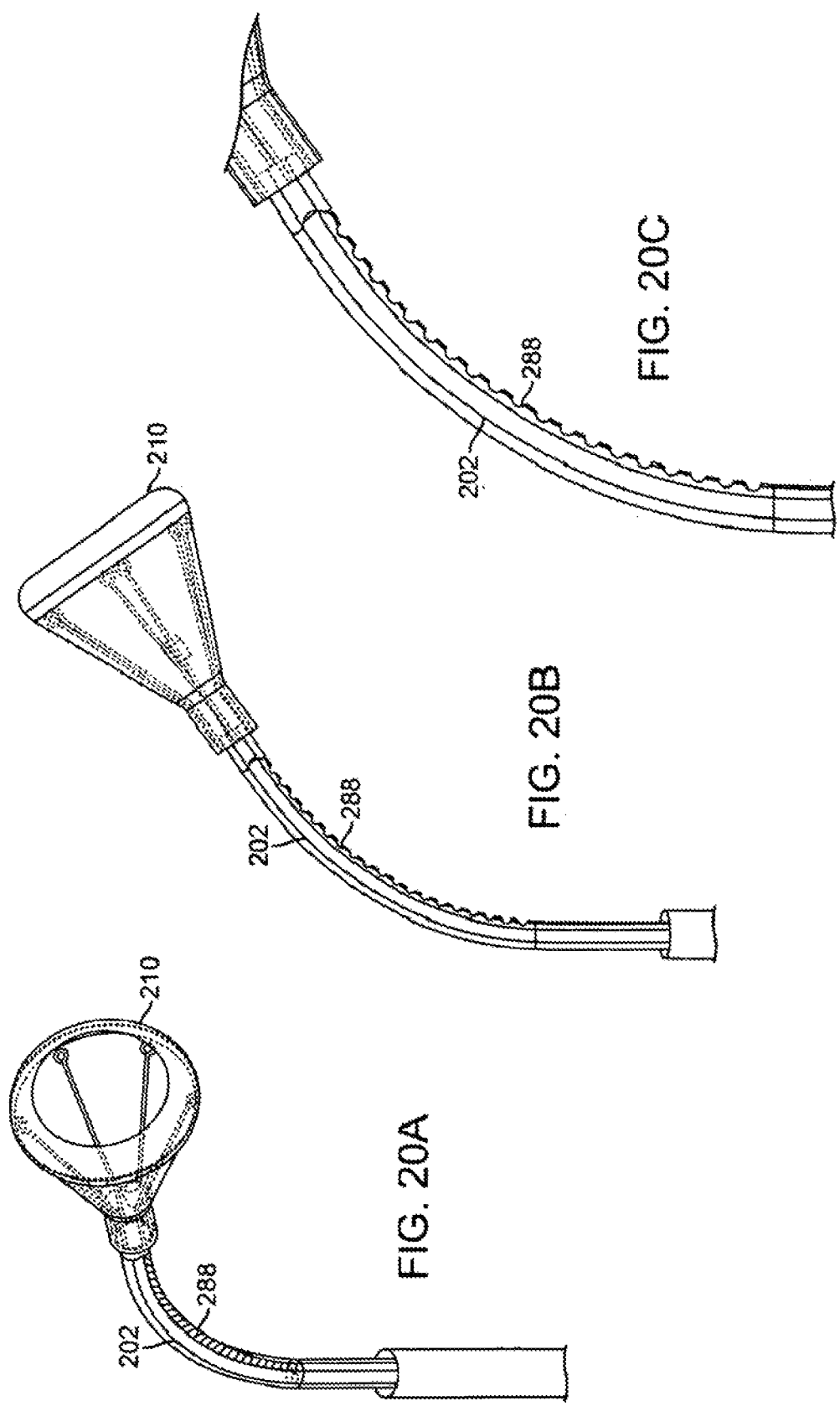

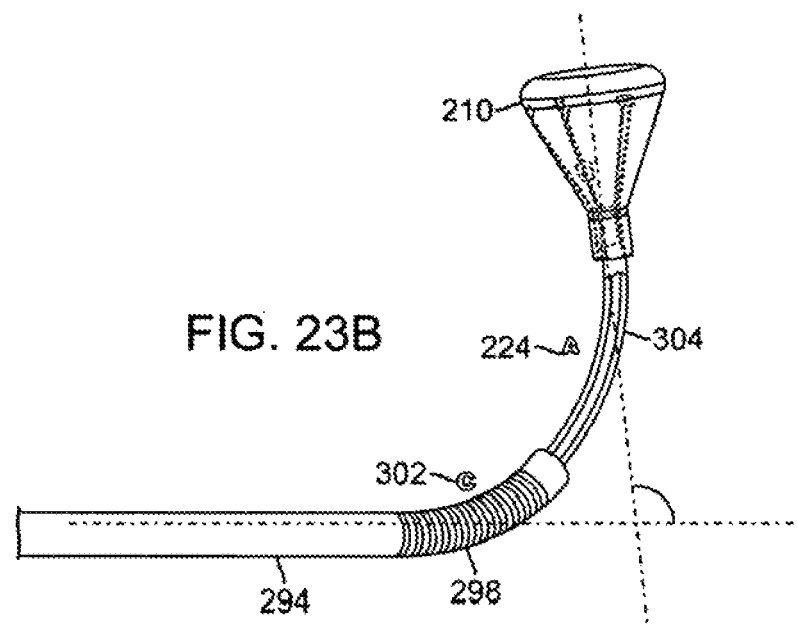
FIG. 23B
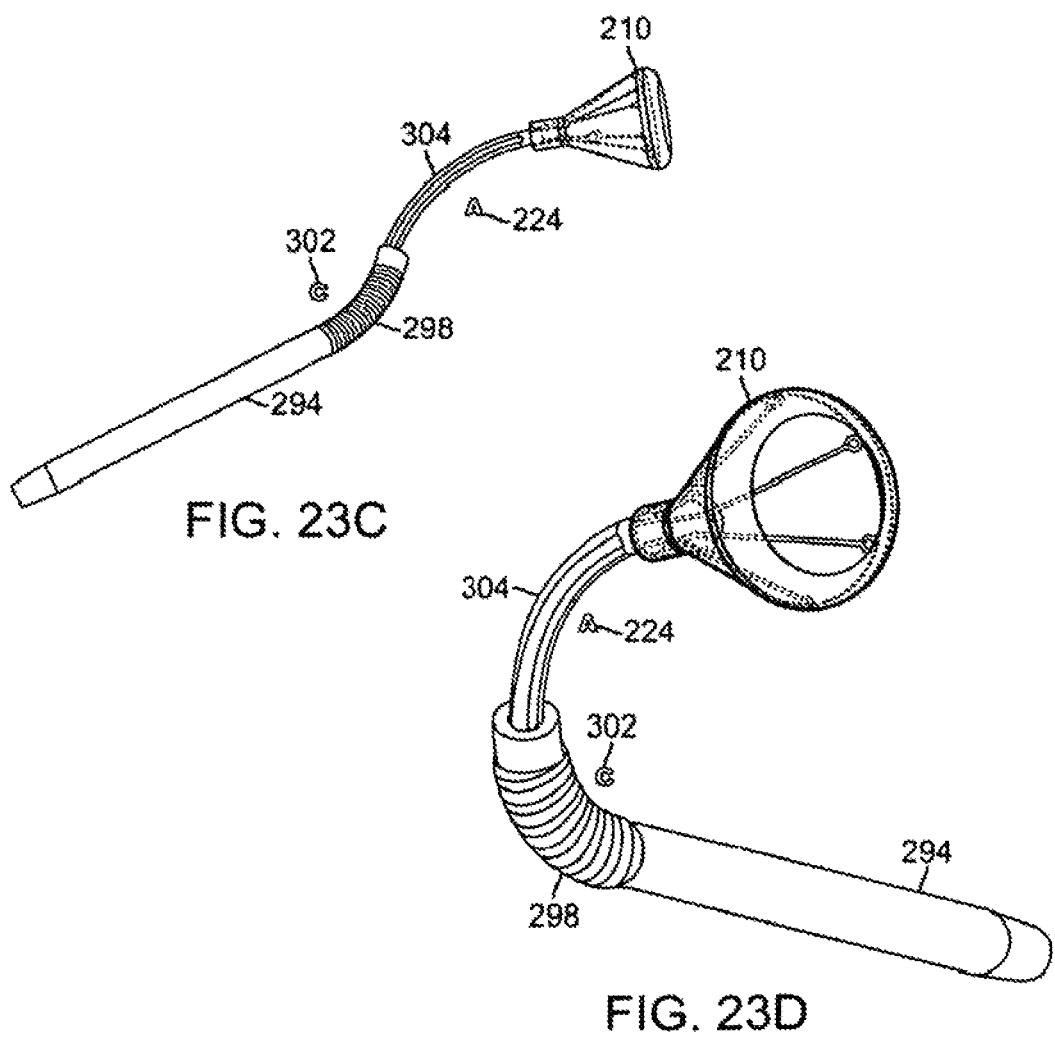
FIG. 23C
FIG. 23D

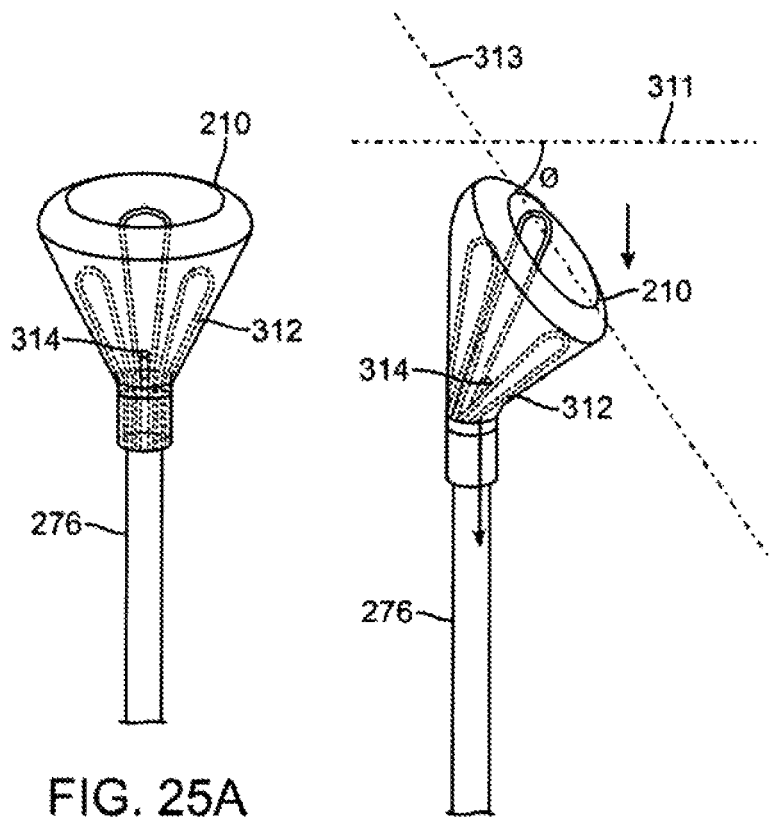
FIG. 25A
FIG. 25B
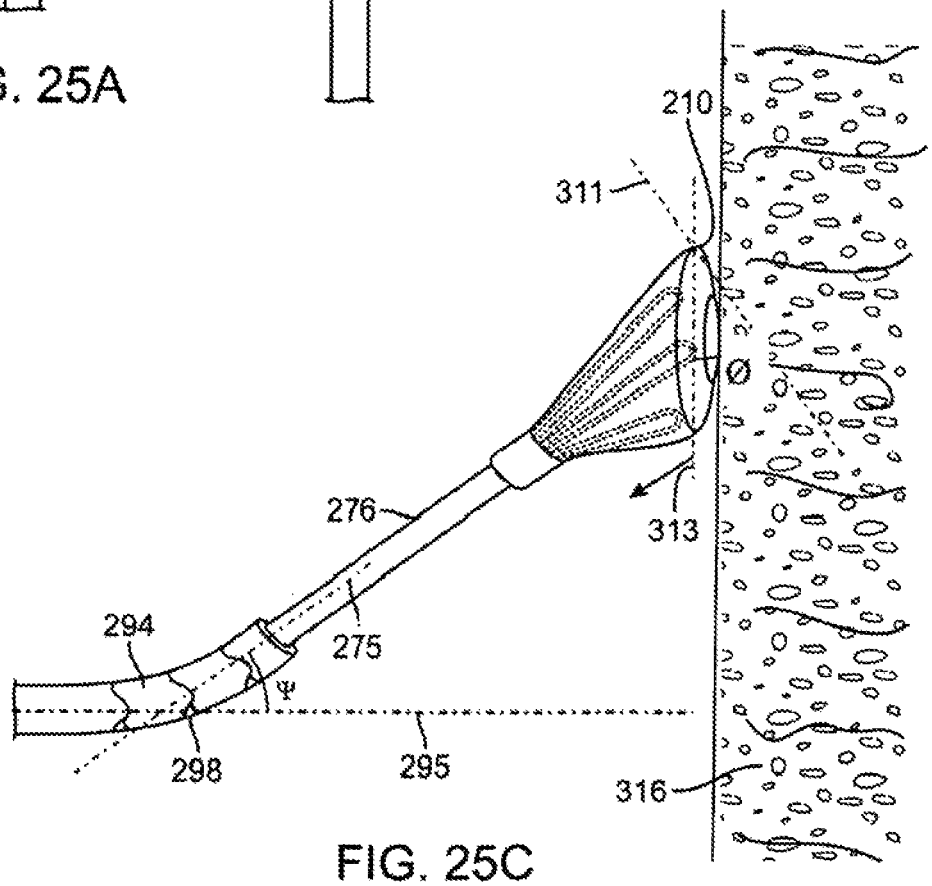
FIG. 25C

COMPLEX SHAPE STEERABLE TISSUE VISUALIZATION AND MANIPULATION CATHETER

CROSS-REFERENCE TO RELATED APPLICATIONS

This application is a continuation of U.S. patent application Ser. No. 12/108,812 filed on Apr. 24, 2008 which claims the benefit of priority to U.S. Prov. Pat. App. 61/914,648 filed Apr. 27, 2007, each of which is incorporated herein by reference in its entirety.

FIELD OF THE INVENTION

The present invention relates generally to catheters having imaging and manipulation features for intravascularly accessing regions of the body.

BACKGROUND OF THE INVENTION

Conventional devices for accessing and visualizing interior regions of a body lumen are known. For example, ultrasound devices have been used to produce images from within a body in vivo. Ultrasound has been used both with and without contrast agents, which typically enhance ultrasound-derived images.

Other conventional methods have utilized catheters or probes having position sensors deployed within the body lumen, such as the interior of a cardiac chamber. These types of positional sensors are typically used to determine the movement of a cardiac tissue surface or the electrical activity within the cardiac tissue. When a sufficient number of points have been sampled by the sensors, a "map" of the cardiac tissue may be generated.

Another conventional device utilizes an inflatable balloon which is typically introduced intravascularly in a deflated state and then inflated against the tissue region to be examined. Imaging is typically accomplished by an optical fiber or other apparatus such as electronic chips for viewing the tissue through the membrane(s) of the inflated balloon. Moreover, the balloon must generally be inflated for imaging. Other conventional balloons utilize a cavity or depression formed at a distal end of the inflated balloon. This cavity or depression is pressed against the tissue to be examined and is flushed with a clear fluid to provide a clear pathway through the blood.

However, such imaging balloons have many inherent disadvantages. For instance, such balloons generally require that the balloon be inflated to a relatively large size which may undesirably displace surrounding tissue and interfere with fine positioning of the imaging system against the tissue. Moreover, the working area created by such inflatable balloons are generally cramped and limited in size. Furthermore, inflated balloons may be susceptible to pressure changes in the surrounding fluid. For example, if the environment surrounding the inflated balloon undergoes pressure changes, e.g., during systolic and diastolic pressure cycles in a beating heart, the constant pressure change may affect the inflated balloon volume and its positioning to produce unsteady or undesirable conditions for optimal tissue imaging.

Accordingly, these types of imaging modalities are generally unable to provide desirable images useful for sufficient diagnosis and therapy of the endoluminal structure, due in part to factors such as dynamic forces generated by the natural movement of the heart. Moreover, anatomic structures within the body can occlude or obstruct the image acquisition process. Also, the presence and movement of opaque bodily fluids such as blood generally make in vivo imaging of tissue regions within the heart difficult.

Other external imaging modalities are also conventionally utilized. For example, computed tomography (CT) and magnetic resonance imaging (MRI) are typical modalities which are widely used to obtain images of body lumens such as the interior chambers of the heart. However, such imaging modalities fail to provide real-time imaging for intra-operative therapeutic procedures. Fluoroscopic imaging, for instance, is widely used to identify anatomic landmarks within the heart and other regions of the body. However, fluoroscopy fails to provide an accurate image of the tissue quality or surface and also fails to provide for instrumentation for performing tissue manipulation or other therapeutic procedures upon the visualized tissue regions. In addition, fluoroscopy provides a shadow of the intervening tissue onto a plate or sensor when it may be desirable to view the intraluminal surface of the tissue to diagnose pathologies or to perform some form of therapy on it.

Moreover, many of the conventional imaging systems lack the capability to provide therapeutic treatments or are difficult to manipulate in providing effective therapies. For instance, the treatment in a patient's heart for atrial fibrillation is generally made difficult by a number of factors, such as visualization of the target tissue, access to the target tissue, and instrument articulation and management, amongst others.

Conventional catheter techniques and devices, for example such as those described in U.S. Pat. Nos. 5,895,417; 5,941,845; and 6,129,724, used on the epicardial surface of the heart may be difficult in assuring a transmural lesion or complete blockage of electrical signals. In addition, current devices may have difficulty dealing with varying thickness of tissue through which a transmural lesion is desired.

Conventional accompanying imaging devices, such as fluoroscopy, are unable to detect perpendicular electrode orientation, catheter movement during the cardiac cycle, and image catheter position throughout lesion formation. Without real-time visualization, it is difficult to reposition devices to another area that requires transmural lesion ablation. The absence of real-time visualization also poses the risk of incorrect placement and ablation of critical structures such as sinus node tissue which can lead to fatal consequences.

BRIEF SUMMARY OF THE INVENTION

A tissue imaging system which is able to provide real-time in vivo access to and images of tissue regions within body lumens such as the heart through opaque media such as blood and which also provides instruments for therapeutic procedures is provided by the invention.

The tissue-imaging apparatus relates to embodiments of a device and method to provide real-time images in vivo of tissue regions within a body lumen such as a heart, which is filled with blood flowing dynamically through it. Such an apparatus may be utilized for many procedures, e.g., mitral valvuloplasty, left atrial appendage closure, arrhythmia ablation (such as treatment for atrial fibrillation), transseptal access and patent foramen ovale closure among other procedures. Further details of such a visualization catheter and methods of use are shown and described in U.S. Pat. Pub. 2006/0184048 A1, which is incorporated herein by reference in its entirety.

Generally, the embodiments of a tissue imaging and manipulation device depicted in the present invention meet the challenge and solve the problem of accessing regions of the body which are typically difficult to access. The design and control of the catheter shaft and the distal tip of the device as disclosed here provide a device uniquely capable of accessing a region such as the human heart, which is a region not only difficult to access, but which also has continuous blood flow. The blood flow provides a barrier to visualizing the local tissue, which in turn makes any manipulation at the local tissue nearly impossible. The unique elements that form the catheter shaft and the distal tip of the device, including the separate control of the shaft and tip and several optional modes of manipulation of either or both, provide for a device adaptable to addressing the challenges inherent in intravascular access and manipulation of heart tissue, and for accomplishing a procedure in any other difficult-to-access region in the body which is bathed in a medium that interferes with visualization.

Blood is continuously flowing through the heart at all times, and as such presents a challenge to direct visualization and subsequent manipulation of heart tissue. The tissue imaging and manipulation apparatus can comprise a delivery catheter or sheath through which a deployment catheter and imaging hood may be advanced for placement against or adjacent to the tissue to be imaged. The deployment catheter can have a fluid delivery lumen through it as well as an imaging lumen within which an optical imaging fiber or electronic imaging assembly may be disposed for imaging tissue. The distal tip of the device is an articulatable tip connected to the catheter shaft, when deployed, the imaging hood within the articulatable tip may be expanded into any number of shapes, e.g., cylindrical, conical as shown, semispherical, etc., provided that an open area or field is defined by the imaging hood. The open area of the articulatable tip is the area within which the tissue region of interest may be imaged. The imaging hood may also define an atraumatic contact lip or edge for placement or abutment against the tissue surface in the region of interest. The distal end of the deployment catheter or separate manipulatable catheters within a delivery sheath may be articulated through various controlling mechanisms such as push-pull wires manually or via computer control.

The visualization catheter may also have one or more membranes or layers of a polymeric material which covers at least a portion of the open area. The membrane or layer may be an extension of the deployed hood or it may be a separate structure. In either case, the membrane or layer may define at least one opening which allows for fluid communication between the visualization hood and the fluid environment within which the catheter is immersed.

In operation, after the imaging hood (at the articulatable tip) has been deployed, fluid may be pumped at a positive pressure through the fluid delivery lumen (within the catheter) until the fluid fills the open area completely and displaces any blood from within the open area. When the hood and membrane or layer is pressed against the tissue region to be visualized or treated, the contact between the one or more openings and the tissue surface may help to retain the clear fluid within the hood for visualization. Moreover, the membrane or layer may help to retain the fluid within the hood while also minimizing any fluid leakage therefrom. Additionally, the one or more openings may also provide for direct access to the underlying tissue region to be treated by any number of tools or instruments positioned within the hood at the articulatable tip.

The fluid may comprise any biocompatible fluid, e.g., saline, water, plasma, Fluorinert™, etc., which is sufficiently transparent to allow for relatively undistorted visualization through the fluid. The fluid may be pumped continuously or intermittently to allow for image capture by an optional processor which may be in communication with the assembly.

The imaging hood may be deployed into an expanded shape and retracted within a catheter utilizing various mechanisms. Moreover, an imaging element, such as a CCD/CMOS imaging camera, may be positioned distally or proximally of the imaging hood when collapsed into its low-profile configuration. Such a configuration may reduce or eliminate friction during deployment and retraction as well as increase the available space within the catheter not only for the imaging unit but also for the hood.

In further controlling the flow of the purging fluid within the hood, various measures may be taken in configuring the assembly to allow for the infusion and controlled retention of the clearing fluid into the hood. By controlling the infusion and retention of the clearing fluid, the introduction of the clearing fluid into the patient body may be limited and the clarity of the imaging of the underlying tissue through the fluid within the hood may be maintained for relatively longer periods of time by inhibiting, delaying, or preventing the infusion of surrounding blood into the viewing field.

Accordingly, there is provided here a device for visualization and manipulation of difficult-to-reach tissue surfaces in a region of a body having a continuous interfering blood flow comprising a steerable catheter shaft having controls for steering of the shaft in multiple planes. The steering of the catheter and/or sheath are may be separately controlled during a procedure so that a proximal steerable section of a catheter shaft can be steered to a target region without manipulation of the distal steerable section. Upon arrival at the target region, slight adjustments and steering of the hood may be articulated (and/or independently) to address the tissue surface or otherwise contact or approach a tissue surface.

The tasks performed by the articulatable hood utilize movement of the catheter shaft, but the movements of the hood and the shaft can be independent in function and control. For example, in order for the hood to contact the tissue surface to flush the region in preparation for imaging, or for making contact with and manipulating the tissue (e.g. forming a lesion around a pulmonary ostium and the like), the catheter shaft may be moved and directed or re-directed and position the hood, then once the catheter shaft has placed the hood in a desirable position, further articulation and control of the hood for cutting or lesion-formation or the like can occur. For example, the hood can be articulated to contact the tissue surface and form a suitable seal in order to flush the surface with saline to visualize the tissue at the surface. The hood may have a conforming lip that can be used to make contact with the tissue surface to facilitate any of these tasks or manipulations. At the point where the hood is negotiating its position at the tissue surface, any subsequent adjustments that may need to be made to the positioning of the shaft can be made independently of the movement of the hood, although, where catheter shaft adjustment can facilitate the hood's position relative to the tissue surface, the two control mechanisms can work in concert with each other.

The catheter shaft may have one of a region of locking units on the shaft, the locking units comprising an ability to move multiple directions, e.g., four way steering. The catheter shaft might also have a separate region of locking units on the shaft proximal to the region of locking units that move four ways, the proximal region of locking units capable of bending only in a single plane. The locking units can be selected from pin links, bump links, ring links, one-way links and four-way links The distal articulatable hood can comprise one or more articulatable units along the hood that are adapted to distal control and that allow the hood to conform to the tissue surface. The articulatable units can comprise multiple steerable leaflets inside a cone-like hood. An articulatable unit can comprise a steerable hood. It may also comprise control members within the hood that allow the practitioner to manipulate the lip that surrounds the hood and the like. The distal articulatable hood can comprise a conforming lip that can be passively steered to contact the tissue surface.

The device can further comprise two or more variations in durometer along the catheter shaft. For example, where there is at least one variation in durometer along the catheter shaft, the variation in durometer can comprise a region of increased flexibility distal to a region of relatively reduced flexibility, so that the distal most end is more flexible and manipulatable.

Where the catheter shaft comprises locking units, the shaft can further comprise an outer sheath to smooth out links in the catheter shaft in the region of the shaft having the locking units.

The catheter shaft can be multi-lumen and comprise multiple pull wires, each pull wire having its own separate access lumen within the catheter shaft. In addition, the device can have a fixed bend sheath over a portion of the catheter shaft to limit the movement of the shaft where the sheath is, and define a fixed angle of direction of the shaft at the fixed bend.

A tissue visualization unit adapted to visualizing accessed tissue can be positioned within the articulatable tip. A tissue manipulation unit adapted to manipulating accessed tissue can likewise be positioned within the articulatable tip. A device can have both such units, for optimally imaging and manipulating in the body during a procedure in real time.

The invention is also a system for intravascularly accessing difficult to access target tissue in a region of the body having continuous interfering blood flow. The system employs a device adapted to visualization and manipulation of the accessed target tissue as just described. The device for the system may have a catheter capable of flushing the target tissue surface at the distal tip so that visualization and manipulation at the surface can occur once the tip is in contact with the tissue surface, and both a unit for visualizing the tissue surface and manipulating tissue at the tissue surface positioned within the articulatable tip. Alternatively, the system can be just for visualization of the tissue surface, in which case it will only have the visualization mechanism.

The invention also contemplates a method of visualizing or manipulating difficult-to-access target tissue in a region of a body having continuous interfering blood flow. The method comprises introducing into a main artery in a patient a device such as just described having the steerable catheter component and the distal attached articulatable tip component. The controls for the catheter shaft include pull wires, locking units and variations in durometer of the shaft. The articulatable hood is expandable upon arrival of the device at a target region in a body, and the hood is capable of expansion to a greater diameter than the catheter shaft. The other elements and capabilities of the shaft and the hood apply to the device in its use in the method. In use, the device is navigated to a difficult-to-access region and target tissue surface, the catheter is steered using one or more controls on pull wires effecting multiple planar curvature of the catheter shaft as needed to more specifically access the target tissue. The catheter shaft might also be steered by virtue of the locking units on the shaft, for example the 4-way locking units provide an opportunity to turn and twist the shaft in several planes. The one-way locking units provide motion, but fix it in one plane. In addition to controlling the shaft, separate control is exerted on the tip to conform the tip to the target tissue surface, and clear a field at the target tissue surface for visualizing or manipulating the tissue at the surface. Flushing the region with fluid and conforming the tip to the surface of the target tissue can ensue.

Manipulating the tissue in the practice of the method can comprise a procedure selected from mitral valvuloplasty, left atrial appendage closure, arrhythmia ablation, transeptal access, and patent foramen ovale closure. Of particular interest is ablation of tissue around the pulmonary ostia, which is a way to treat atrial fibrillation. The endocardium can be visualized in the method.

Typically, the complex manipulations will target the heart tissue, and can be such tasks as pulmonary ostia ablation which treats atrial fibrillation. The device comprises a steerable catheter shaft having control for steering of the shaft in multiple planes. The catheter shaft will typically have a proximal region of locking units on the shaft capable of providing uni-directional movement of the catheter shaft in that region, and a distal region of locking units on the shaft capable of providing 4-way directional movement of the catheter shaft in that distal region. The catheter shaft is also connected to a distal articulatable tip expandable upon arrival of the device at the tissue surface, the tip capable of expansion to a greater diameter than the catheter shaft, the tip adapted to conform to a target tissue surface within the target region in the body upon articulation of the tip, and capable of flushing the target tissue surface so that visualization and manipulation at the surface can occur. In this device the manipulations comprising articulation of the articulatable tip and steering of the steerable catheter are separately controlled during a procedure. In order to address atrial fibrillation, at the left atrium in the heart, the tissue surface of that is the ostia of the pulmonary veins is accessed, and tissue surrounding these ostia is ablated by manipulating the articulatable tip of the catheter.

A procedure comprising forming lesions around a tissue surface comprising ostia of pulmonary veins in a left atrium is accomplished by introducing a device in a femoral artery and directing it to the heart, the device comprising the elements of the device just described. The articulatable tip of the device may be adapted to conform to one at a time to an ostium of the pulmonary vein of the left atrium, the tip will be capable of flushing the tissue surface of the ostium so that visualization and manipulation at the surface can occur. Manipulations comprising articulation of the articulatable tip and steering of the steerable catheter will be separately controlled during the atrial fibrillation treatment procedure. Such maneuvers as positioning the tip at a first ostium and purging charged saline at the tissue surface to form lesions around the ostium by steering the tip around the first ostium, and positioning the tip at a second ostium and purging charged saline at the tissue surface to form lesions around the ostium by steering the tip around the second ostium, can be conducted to accomplish a treatment directed to atrial fibrillation.

BRIEF DESCRIPTION OF THE DRAWINGS

FIG. 11D shows the perspective views of the same device illustrating articulating and torquing motions to steer the hood into different positions.

FIG. 13E shows the side view of the same device prior to placement against a tissue surface.

FIG. 13F shows the side view of the same device pressed against the tissue surface.

FIG. 13G shows the side view of the same device pressed against the tissue surface by reducing curvature of curves A and B.

FIG. 14C shows the perspective view of the same device with hood articulatable in multiple directions.

FIG. 14D shows the perspective view of the same device with hood articulatable in multiple directions.

FIG. 14E shows the perspective view of the same device with hood articulatable in multiple directions.

FIG. 15D shows the front view of the same device with steerable links aligned linearly.

FIG. 15E shows the side view of the same device with steerable links aligned into a double bend configuration.

FIG. 15F shows the side view of the same device showing steerable links aligned to make tight bend radius to retroflex the hood.

FIG. 17A shows the side view of a variation of the tissue visualization catheter with steerable ring links.

FIG. 17B shows the close up side view of ring links.

FIG. 20A shows the perspective view of a steerable tissue visualization catheter with slit tube as the steerable segment.

FIG. 20B shows the side view of the same device.

FIG. 20C shows the close up side view of the slit tube.

FIG. 23B shows the side view of the visualization catheter and introducer sheath with pre-bent curves aligned in the same direction and plane to steer the hood across a relatively wide angle.

FIG. 23C shows the side view of the same system with both pre-bend curves in the same plane but rotated in opposite directions relative to one another.

FIG. 23D illustrates a perspective view of the same system with both pre-bent curves in different planes relative to one another.

FIG. 25A shows a side view of a steerable hood of the tissue visualization catheter with multiple steerable leaflets.

FIG. 25B shows a side view of a steerable hood having multiple steering leaflets actuated to steer the hood into an angled configuration relative to a longitudinal axis of the deployment catheter FIG. 25C illustrates a side view of the hood angled relative to the deployment catheter positioned against a tissue surface.

DETAILED DESCRIPTION OF THE INVENTION

Various exemplary embodiments of the invention are described below. Reference is made to these examples in a non-limiting sense. They are provided to illustrate more broadly applicable aspects of the present invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. All such modifications are intended to be within the scope of the claims made herein.

The tissue-imaging and manipulation apparatus of the invention is able to provide real-time images in vivo of tissue regions within a body lumen such as a heart, which are filled with blood flowing dynamically through the region. The apparatus is also able to provide intravascular tools and instruments for performing various procedures upon the imaged tissue regions. Such an apparatus may be utilized for many procedures, e.g., facilitating transseptal access to the left atrium, cannulating the coronary sinus, diagnosis of valve regurgitation/stenosis, valvuloplasty, atrial appendage closure, arrhythmogenic focus ablation (such as for treating atrial fibrulation), among other procedures. Disclosure and information regarding tissue visualization catheters generally which can be applied to the invention are shown and described in further detail in commonly owned U.S. patent application Ser. No. 11/259,498 filed Oct. 25, 2005, and published as 2006/0184048, which is incorporated herein by reference in its entirety. The basic apparatus for visualizing and manipulating tissue upon intravascular access to the target region are depicted in FIGS. 1-10. The specific details of the invention that permit specific access to difficult-to-access regions such as regions in the heart are depicted in FIGS. 11 to 32. Specific embodiments depicting devices and methods for specific heart-based tissue manipulations such as forming lesions around the pulmonary ostia are shown in FIGS. 28 to 32.

Figure 1A:
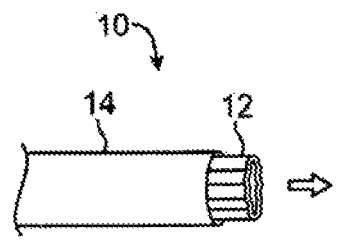
FIG. 1A shows a side view of one variation of a tissue imaging apparatus during deployment from a sheath or delivery catheter.
Figure 1B:
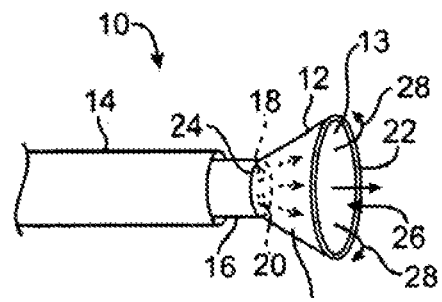
FIG. 1B shows the deployed tissue imaging apparatus of FIG. 1A having an optionally expandable hood or sheath attached to an imaging and/or diagnostic catheter.
Figure 1C:
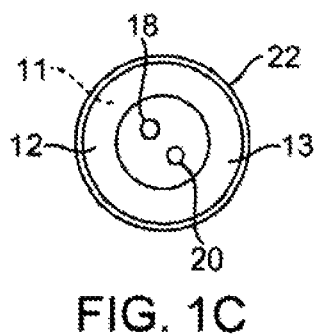
FIG. 1C shows an end view of a deployed imaging apparatus.

One variation of a tissue access and imaging apparatus is shown in the detail perspective views of FIGS. 1A to 1C. As shown in FIG. 1A, tissue imaging and manipulation assembly 10 may be delivered intravascularly through the patient's body in a low-profile configuration via a delivery catheter or sheath 14. In the case of treating tissue, such as the mitral valve located at the outflow tract of the left atrium of the heart, it is generally desirable to enter or access the left atrium while minimizing trauma to the patient. To non-operatively effect such access, one conventional approach involves puncturing the intra-atrial septum from the right atrial chamber to the left atrial chamber in a procedure commonly called a transseptal procedure or septostomy. For procedures such as percutaneous valve repair and replacement, transseptal access to the left atrial chamber of the heart may allow for larger devices to be introduced into the venous system than can generally be introduced percutaneously into the arterial system.

When the imaging and manipulation assembly 10 is ready to be utilized for imaging tissue, imaging hood 12 may be advanced relative to catheter 14 and deployed from a distal opening of catheter 14, as shown by the arrow. Upon deployment, imaging hood 12 may be unconstrained to expand or open into a deployed imaging configuration, as shown in FIG. 1B. Imaging hood 12 may be fabricated from a variety of pliable or conformable biocompatible material including but not limited to, e.g., polymeric, plastic, or woven materials. One example of a woven material is Kevlar® (E. I. du Pont de Nemours, Wilmington, DE), which is an aramid and which can be made into thin, e.g., less than 0.001 in., materials which maintain enough integrity for such applications described herein. Moreover, the imaging hood 12 may be fabricated from a translucent or opaque material and in a variety of different colors to optimize or attenuate any reflected lighting from surrounding fluids or structures, i.e., anatomical or mechanical structures or instruments. In either case, imaging hood 12 may be fabricated into a uniform structure or a scaffold-supported structure, in which case a scaffold made of a shape memory alloy, such as Nitinol, or a spring steel, or plastic, etc., may be fabricated and covered with the polymeric, plastic, or woven material. Hence, imaging hood 12 may comprise any of a wide variety of barriers or membrane structures, as may generally be used to localize displacement of blood or the like from a selected volume of a body lumen or heart chamber. In exemplary embodiments, a volume within an inner surface 13 of imaging hood 12 will be significantly less than a volume of the hood 12 between inner surface 13 and outer surface 11.

Imaging hood 12 may be attached at interface 24 to a deployment catheter 16 which may be translated independently of deployment catheter or sheath 14. Attachment of interface 24 may be accomplished through any number of conventional methods. Deployment catheter 16 may define a fluid delivery lumen 18 as well as an imaging lumen 20 within which an optical imaging fiber or assembly may be disposed for imaging tissue. When deployed, imaging hood 12 may expand into any number of shapes, e.g., cylindrical, conical as shown, semi-spherical, etc., provided that an open area or field 26 is defined by imaging hood 12. The open area 26 is the area within which the tissue region of interest may be imaged. Imaging hood 12 may also define an atraumatic contact lip or edge 22 for placement or abutment against the tissue region of interest. Moreover, the diameter of imaging hood 12 at its maximum fully deployed diameter, e.g., at contact lip or edge 22, is typically greater relative to a diameter of the deployment catheter 16 (although a diameter of contact lip or edge 22 may be made to have a smaller or equal diameter of deployment catheter 16). For instance, the contact edge diameter may range anywhere from 1 to 5 times (or even greater, as practicable) a diameter of deployment catheter 16. FIG. 1C shows an end view of the imaging hood 12 in its deployed configuration. Also shown are the contact lip or edge 22 and fluid delivery lumen 18 and imaging lumen 20.

Figure 1D:
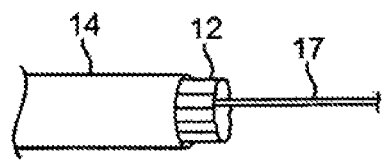
FIGS. 1D to 1F show the apparatus of FIGS. 1A to 1C with an additional lumen, e.g., for passage of a guidewire therethrough.
Figure 1E:
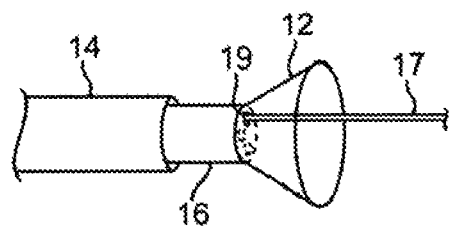
Figure 1F:
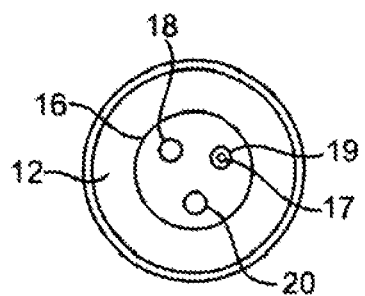

The imaging and manipulation assembly 10 may additionally define a guidewire lumen therethrough, e.g., a concentric or eccentric lumen, as shown in the side and end views, respectively, of FIGS. 1D to 1F. The deployment catheter 16 may define guidewire lumen 19 for facilitating the passage of the system over or along a guidewire 17, which may be advanced intravascularly within a body lumen. The deployment catheter 16 may then be advanced over the guidewire 17, as generally known in the art.

In operation, after imaging hood 12 has been deployed, as in FIG. 1B, and desirably positioned against the tissue region to be imaged along contact edge 22, the displacing fluid may be pumped at positive pressure through fluid delivery lumen 18 until the fluid fills open area 26 completely and displaces any fluid 28 from within open area 26. The displacing fluid flow may be laminarized to improve its clearing effect and to help prevent blood from re-entering the imaging hood 12. Alternatively, fluid flow may be started before the deployment takes place. The displacing fluid, also described herein as imaging fluid, may comprise any biocompatible fluid, e.g., saline, water, plasma, etc., which is sufficiently transparent to allow for relatively undistorted visualization through the fluid. Alternatively or additionally, any number of therapeutic drugs may be suspended within the fluid or may comprise the fluid itself which is pumped into open area 26 and which is subsequently passed into and through the heart and the patient body.

Figure 2A:
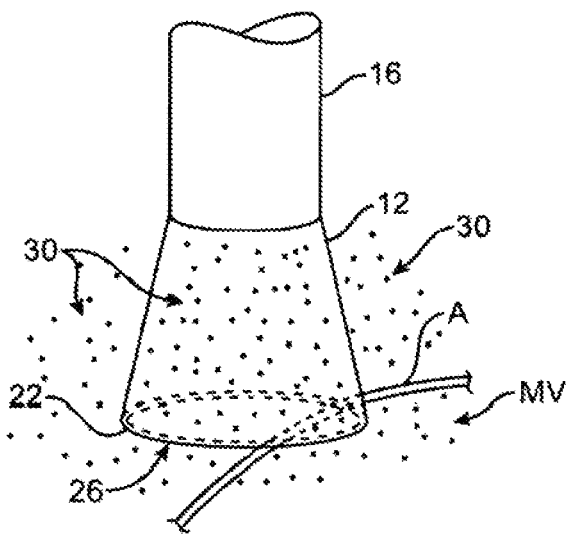
FIGS. 2A and 2B show one example of a deployed tissue imager positioned against or adjacent to the tissue to be imaged and a flow of fluid, such as saline, displacing blood from within the expandable hood.
Figure 2B:
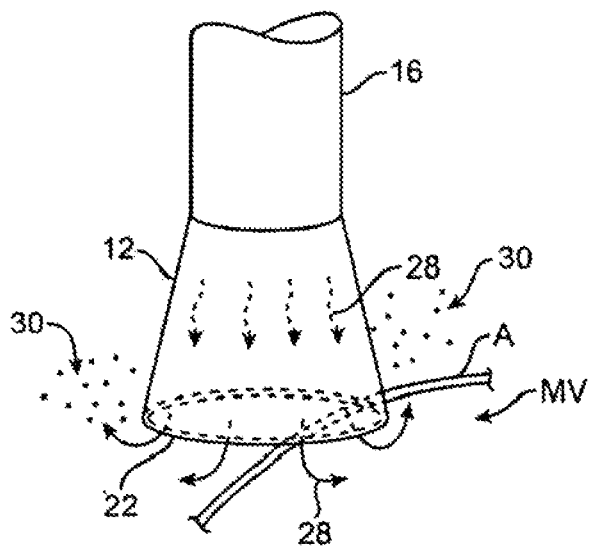

As seen in the example of FIGS. 2A and 2B, deployment catheter 16 may be manipulated to position deployed imaging hood 12 against or near the underlying tissue region of interest to be imaged, in this example a portion of annulus A of mitral valve MV within the left atrial chamber. As the surrounding blood 30 flows around imaging hood 12 and within open area 26 defined within imaging hood 12, as seen in FIG. 2A, the underlying annulus A is obstructed by the opaque blood 30 and is difficult to view through the imaging lumen 20. The translucent fluid 28, such as saline, may then be pumped through fluid delivery lumen 18, intermittently or continuously, until the blood 30 is at least partially, and preferably completely, displaced from within open area 26 by fluid 28, as shown in FIG. 2B.

Although contact edge 22 need not directly contact the underlying tissue, it is at least preferably brought into close proximity to the tissue such that the flow of clear fluid 28 from open area 26 may be maintained to inhibit significant backflow of blood 30 back into open area 26. Contact edge 22 may also be made of a soft elastomeric material such as certain soft grades of silicone or polyurethane, as typically known, to help contact edge 22 conform to an uneven or rough underlying anatomical tissue surface. Once the blood 30 has been displaced from imaging hood 12, an image may then be viewed of the underlying tissue through the clear fluid 30. This image may then be recorded or available for real-time viewing for performing a therapeutic procedure. The positive flow of fluid 28 may be maintained continuously to provide for clear viewing of the underlying tissue. Alternatively, the fluid 28 may be pumped temporarily or sporadically only until a clear view of the tissue is available to be imaged and recorded, at which point the fluid flow 28 may cease and blood 30 may be allowed to seep or flow back into imaging hood 12. This process may be repeated a number of times at the same tissue region or at multiple tissue regions.

In desirably positioning the assembly at various regions within the patient body, a number of articulation and manipulation controls may be utilized. For example, as shown in the articulatable imaging assembly 40 in FIG. 3A, one or more push-pull wires 42 may be routed through deployment catheter 16 for steering the distal end portion of the device in various directions 46 to desirably position the imaging hood 12 adjacent to a region of tissue to be visualized. Depending upon the positioning and the number of push-pull wires 42 utilized, deployment catheter 16 and imaging hood 12 may be articulated into any number of configurations 44. The push-pull wire or wires 42 may be articulated via their proximal ends from outside the patient body manually utilizing one or more controls. Alternatively, deployment catheter 16 may be articulated by computer control, as further described below.

Figure 3A:
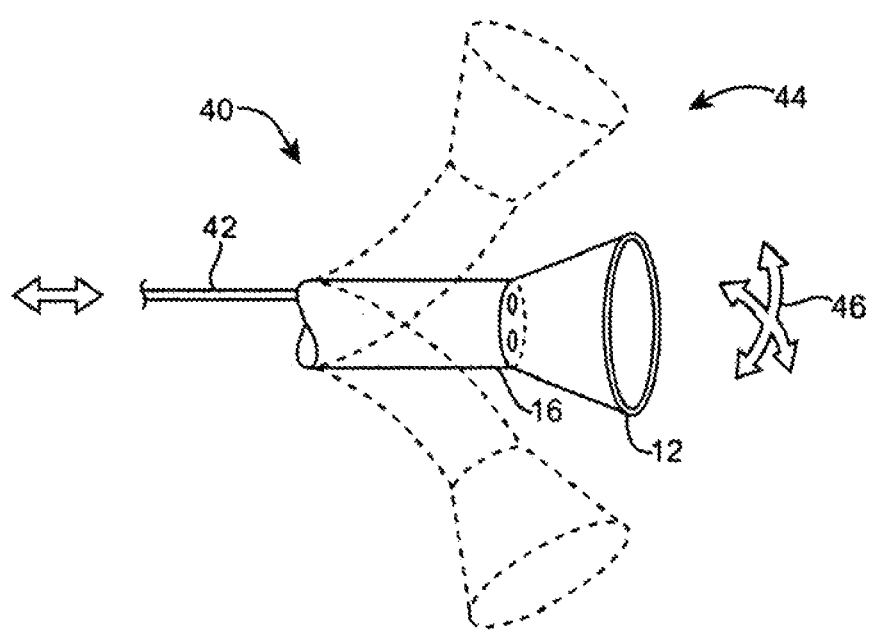
FIG. 3A shows an articulatable imaging assembly which may be manipulated via push-pull wires or by computer control.
Figure 3B:
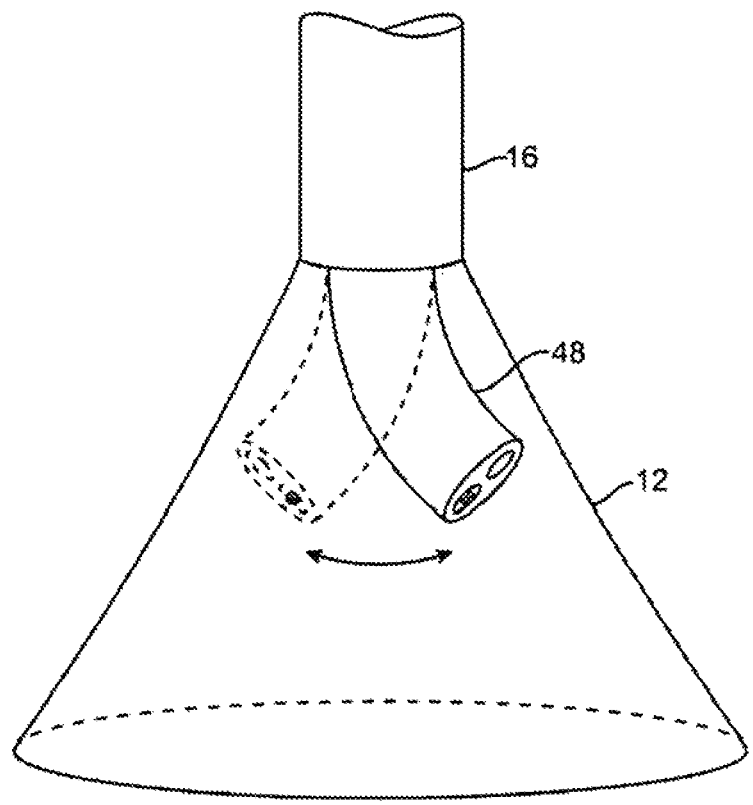
FIGS. 3B and 3C show steerable instruments, respectively, where an articulatable delivery catheter may be steered within the imaging hood or a distal portion of the deployment catheter itself may be steered.

Additionally or alternatively, an articulatable delivery catheter 48, which may be articulated via one or more push-pull wires and having an imaging lumen and one or more working lumens, may be delivered through the deployment catheter 16 and into imaging hood 12. With a distal portion of articulatable delivery catheter 48 within imaging hood 12, the clear displacing fluid may be pumped through delivery catheter 48 or deployment catheter 16 to clear the field within imaging hood 12. As shown in FIG. 3B, the articulatable delivery catheter 48 may be articulated within the imaging hood to obtain a better image of tissue adjacent to the imaging hood 12. Moreover, articulatable delivery catheter 48 may be articulated to direct an instrument or tool passed through the catheter 48, as described in detail below, to specific areas of tissue imaged through imaging hood 12 without having to reposition deployment catheter 16 and re-clear the imaging field within hood 12.

Figure 3C:
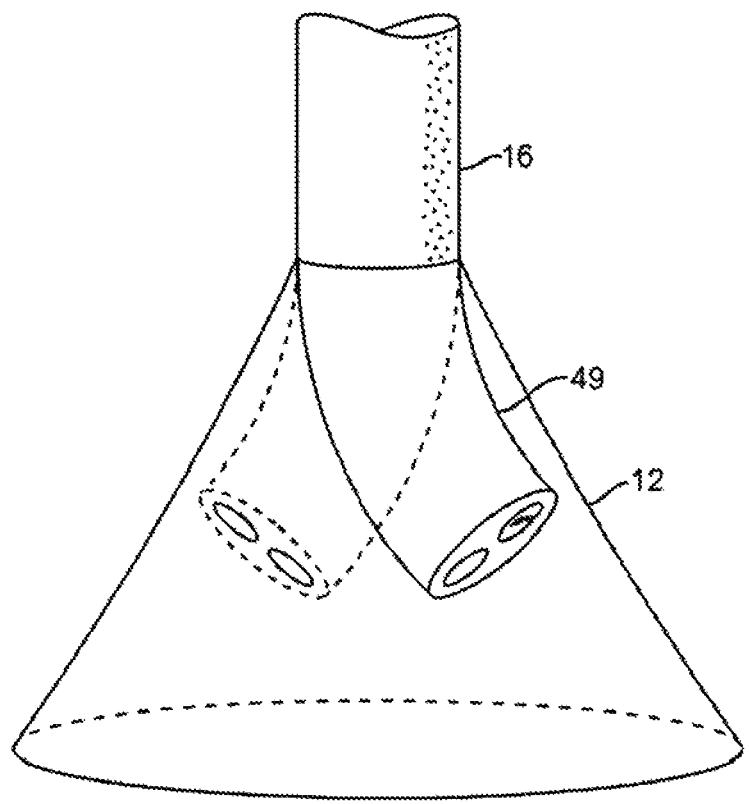

Alternatively, rather than passing an articulatable delivery catheter 48 through the deployment catheter 16, a distal portion of the deployment catheter 16 itself may comprise a distal end 49 which is articulatable within imaging hood 12, as shown in FIG. 3C. Directed imaging, instrument delivery, etc., may be accomplished directly through one or more lumens within deployment catheter 16 to specific regions of the underlying tissue imaged within imaging hood 12.

Figure 4A:
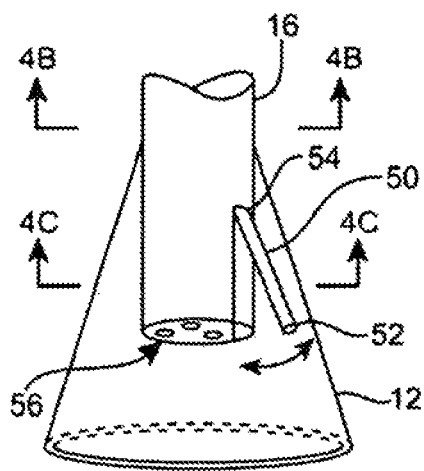
FIGS. 4A to 4C show side and cross-sectional end views, respectively, of another variation having an off-axis imaging capability.

Visualization within the imaging hood 12 may be accomplished through an imaging lumen 20 defined through deployment catheter 16, as described above. In such a configuration, visualization is available in a straight-line manner, i.e., images are generated from the field distally along a longitudinal axis defined by the deployment catheter 16. Alternatively or additionally, an articulatable imaging assembly having a pivotable support member 50 may be connected to, mounted to, or otherwise passed through deployment catheter 16 to provide for visualization off-axis relative to the longitudinal axis defined by deployment catheter 16, as shown in FIG. 4A. Support member 50 may have an imaging element 52, e.g., a CCD or CMOS imager or optical fiber, attached at its distal end with its proximal end connected to deployment catheter 16 via a pivoting connection 54.

Figure 4B:
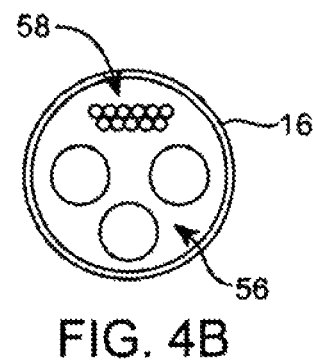
Figure 4C:
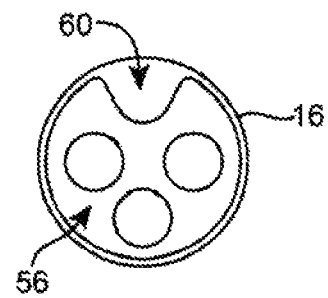

If one or more optical fibers are utilized for imaging, the optical fibers 58 may be passed through deployment catheter 16, as shown in the cross-section of FIG. 4B, and routed through the support member 50. The use of optical fibers 58 may provide for increased diameter sizes of the one or several lumens 56 through deployment catheter 16 for the passage of diagnostic and/or therapeutic tools therethrough. Alternatively, electronic chips, such as a charge coupled device (CCD) or a CMOS imager, which are typically known, may be utilized in place of the optical fibers 58, in which case the electronic imager may be positioned in the distal portion of the deployment catheter 16 with electric wires being routed proximally through the deployment catheter 16. Alternatively, the electronic imagers may be wirelessly coupled to a receiver for the wireless transmission of images. Additional optical fibers or light emitting diodes (LEDs) can be used to provide lighting for the image or operative theater, as described below in further detail. Support member 50 may be pivoted via connection 54 such that the member 50 can be positioned in a low-profile configuration within channel or groove 60 defined in a distal portion of catheter 16, as shown in the cross-section of FIG. 4C. During intravascular delivery of deployment catheter 16 through the patient body, support member 50 can be positioned within channel or groove 60 with imaging hood 12 also in its low-profile configuration. During visualization, imaging hood 12 may be expanded into its deployed configuration and support member 50 may be deployed into its off-axis configuration for imaging the tissue adjacent to hood 12, as in FIG. 4A. Other configurations for support member 50 for off-axis visualization may be utilized, as desired.

Figure 4D:
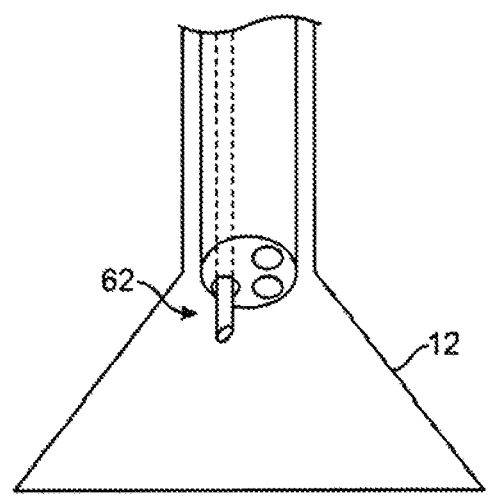
FIGS. 4D and 4E show examples of various visualization imagers which may be utilized within or along the imaging hood.
Figure 4E:
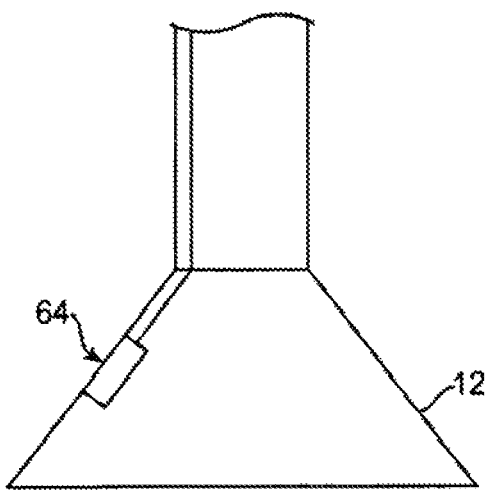

FIG. 4D shows a partial cross-sectional view of an example where one or more optical fiber bundles 62 may be positioned within the catheter and within imaging hood 12 to provide direct in-line imaging of the open area within hood 12. FIG. 4E shows another example where an imaging element 64 (e.g., CCD or CMOS electronic imager) may be placed along an interior surface of imaging hood 12 to provide imaging of the open area such that the imaging element 64 is off-axis relative to a longitudinal axis of the hood 12. The off-axis position of element 64 may provide for direct visualization and uninhibited access by instruments from the catheter to the underlying tissue during treatment.

Figure 5:
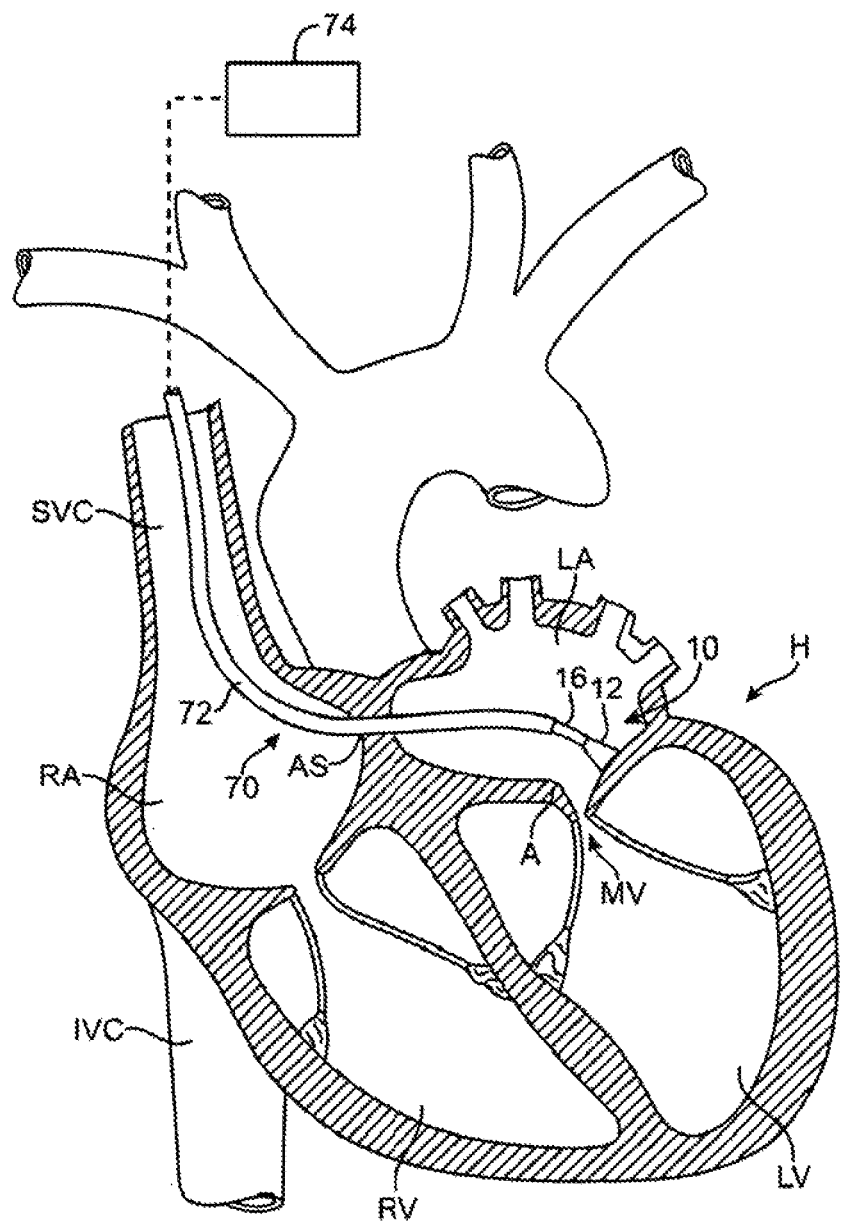
FIG. 5 shows an illustrative view of an example of a tissue imager advanced intravascularly within a heart for imaging tissue regions within an atrial chamber.

FIG. 5 shows an illustrative cross-sectional view of a heart H having tissue regions of interest being viewed via an imaging assembly 10. In this example, delivery catheter assembly 70 may be introduced percutaneously into the patient's vasculature and advanced through the superior vena cava SVC and into the right atrium RA. The delivery catheter or sheath 72 may be articulated through the atrial septum AS and into the left atrium LA for viewing or treating the tissue, e.g., the annulus A, surrounding the mitral valve MV. As shown, deployment catheter 16 and imaging hood 12 may be advanced out of delivery catheter 72 and brought into contact or in proximity to the tissue region of interest. In other examples, delivery catheter assembly 70 may be advanced through the inferior vena cava IVC, if so desired. Moreover, other regions of the heart H, e.g., the right ventricle RV or left ventricle LV, may also be accessed and imaged or treated by imaging assembly 10.

In accessing regions of the heart H or other parts of the body, the delivery catheter or sheath 14 may comprise a conventional intra-vascular catheter or an endoluminal delivery device. Alternatively, robotically-controlled delivery catheters may also be optionally utilized with the imaging assembly described herein, in which case a computer-controller 74 may be used to control the articulation and positioning of the delivery catheter 14. An example of a robotically-controlled delivery catheter which may be utilized is described in further detail in US Pat. Pub. 2002/0087169 A1 to Brock et al. entitled "Flexible Instrument", which is incorporated herein by reference in its entirety. Other robotically-controlled delivery catheters manufactured by Hansen Medical, Inc. (Mountain View, CA) may also be utilized with the delivery catheter 14.

Figure 6A:
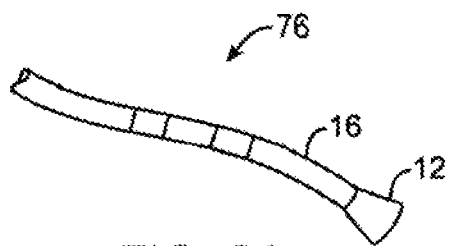
FIGS. 6A to 6C illustrate deployment catheters having one or more optional inflatable balloons or anchors for stabilizing the device during a procedure.
Figure 6B:
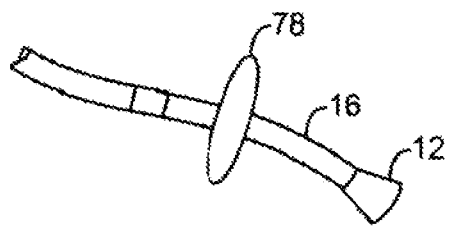
Figure 6C:
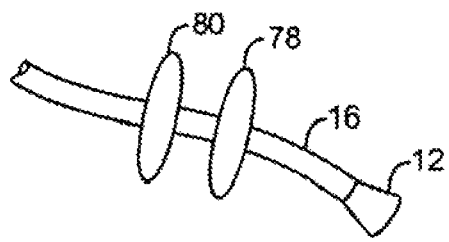

To facilitate stabilization of the deployment catheter 16 during a procedure, one or more inflatable balloons or anchors 76 may be positioned along the length of catheter 16, as shown in FIG. 6A. For example, when utilizing a transseptal approach across the atrial septum AS into the left atrium LA, the inflatable balloons 76 may be inflated from a low-profile into their expanded configuration to temporarily anchor or stabilize the catheter 16 position relative to the heart H. FIG. 6B shows a first balloon 78 inflated while FIG. 6C also shows a second balloon 80 inflated proximal to the first balloon 78. In such a configuration, the septal wall AS may be wedged or sandwiched between the balloons 78, 80 to temporarily stabilize the catheter 16 and imaging hood 12. A single balloon 78 or both balloons 78, 80 may be used. Other alternatives may utilize expandable mesh members, malecots, or any other temporary expandable structure. After a procedure has been accomplished, the balloon assembly 76 may be deflated or re-configured into a low-profile for removal of the deployment catheter 16.

Figure 7A:
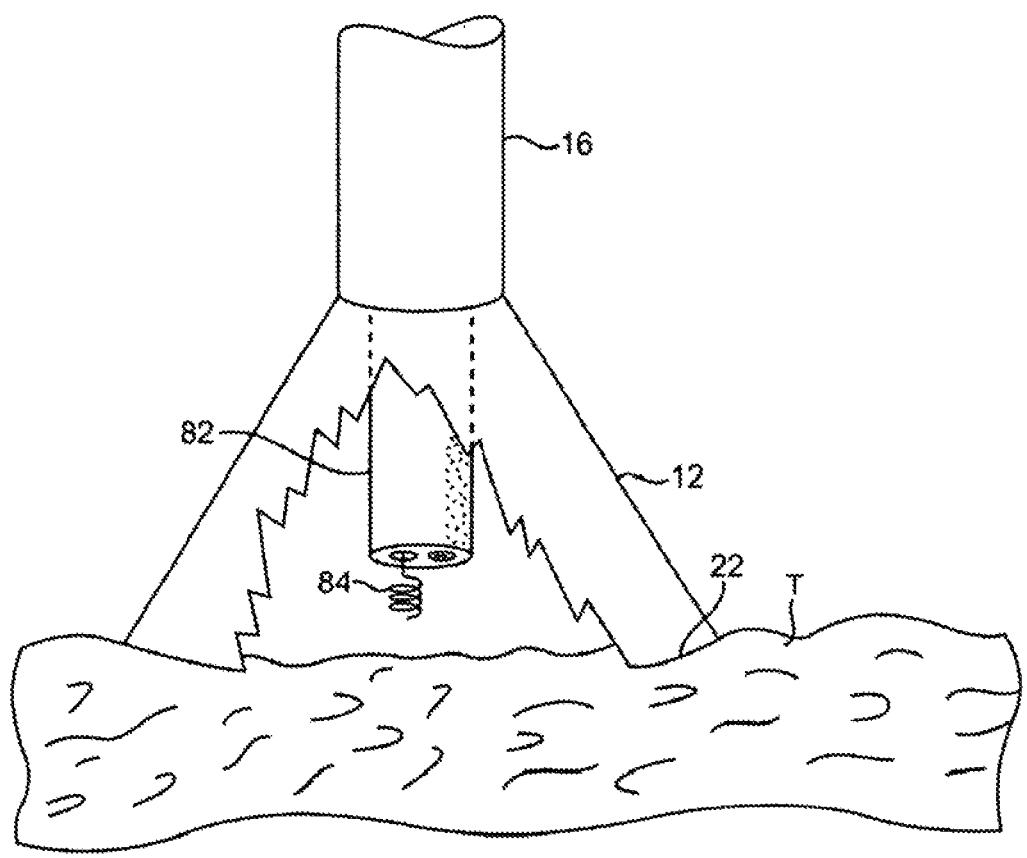
FIGS. 7A and 7B illustrate a variation of an anchoring mechanism such as a helical tissue piercing device for temporarily stabilizing the imaging hood relative to a tissue surface.
Figure 7B:
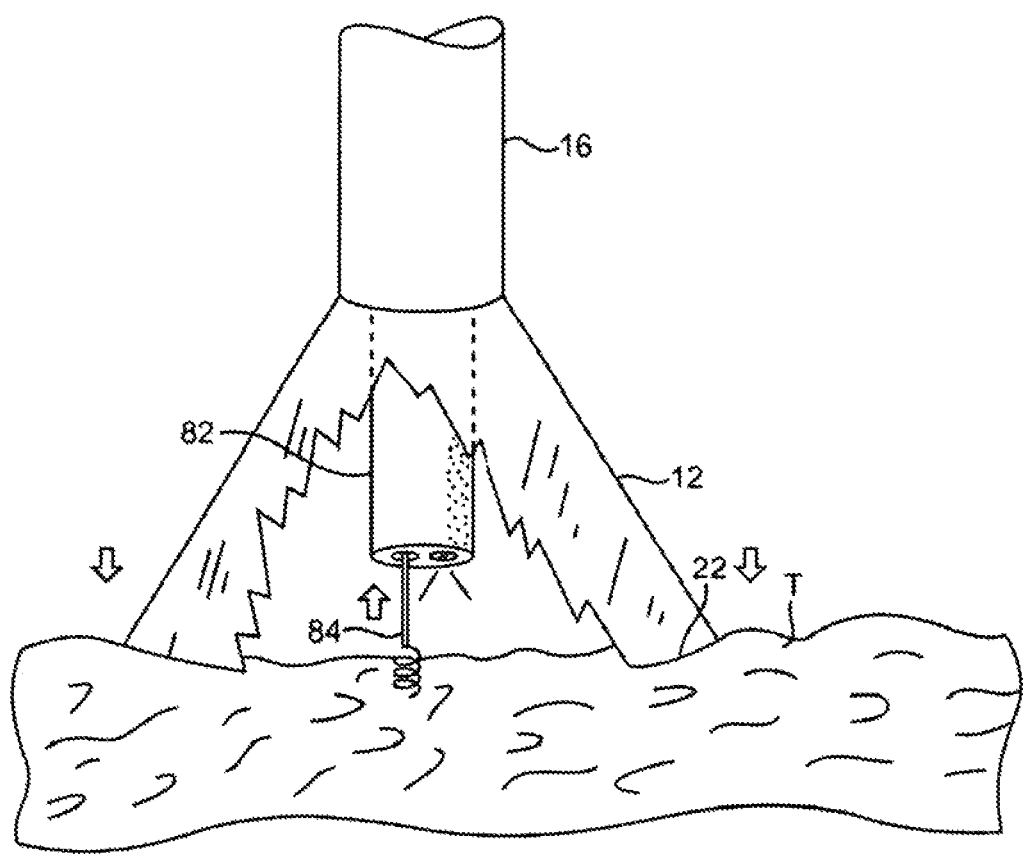

To further stabilize a position of the imaging hood 12 relative to a tissue surface to be imaged, various anchoring mechanisms may be optionally employed for temporarily holding the imaging hood 12 against the tissue. Such anchoring mechanisms may be particularly useful for imaging tissue which is subject to movement, e.g., when imaging tissue within the chambers of a beating heart. A tool delivery catheter 82 having at least one instrument lumen and an optional visualization lumen may be delivered through deployment catheter 16 and into an expanded imaging hood 12. As the imaging hood 12 is brought into contact against a tissue surface T to be examined, anchoring mechanisms such as a helical tissue piercing device 84 may be passed through the tool delivery catheter 82, as shown in FIG. 7A, and into imaging hood 12.

The helical tissue engaging device 84 may be torqued from its proximal end outside the patient body to temporarily anchor itself into the underlying tissue surface T. Once embedded within the tissue T, the helical tissue engaging device 84 may be pulled proximally relative to deployment catheter 16 while the deployment catheter 16 and imaging hood 12 are pushed distally, as indicated by the arrows in FIG. 7B, to gently force the contact edge or lip 22 of imaging hood against the tissue T. The positioning of the tissue engaging device 84 may be locked temporarily relative to the deployment catheter 16 to ensure secure positioning of the imaging hood 12 during a diagnostic or therapeutic procedure within the imaging hood 12. After a procedure, tissue engaging device 84 may be disengaged from the tissue by torquing its proximal end in the opposite direction to remove the anchor form the tissue T and the deployment catheter 16 may be repositioned to another region of tissue where the anchoring process may be repeated or removed from the patient body. The tissue engaging device 84 may also be constructed from other known tissue engaging devices such as vacuum-assisted engagement or grasper-assisted engagement tools, among others.

Although a helical anchor 84 is shown, this is intended to be illustrative and other types of temporary anchors may be utilized, e.g., hooked or barbed anchors, graspers, etc. Moreover, the tool delivery catheter 82 may be omitted entirely and the anchoring device may be delivered directly through a lumen defined through the deployment catheter 16.

Figure 7C:
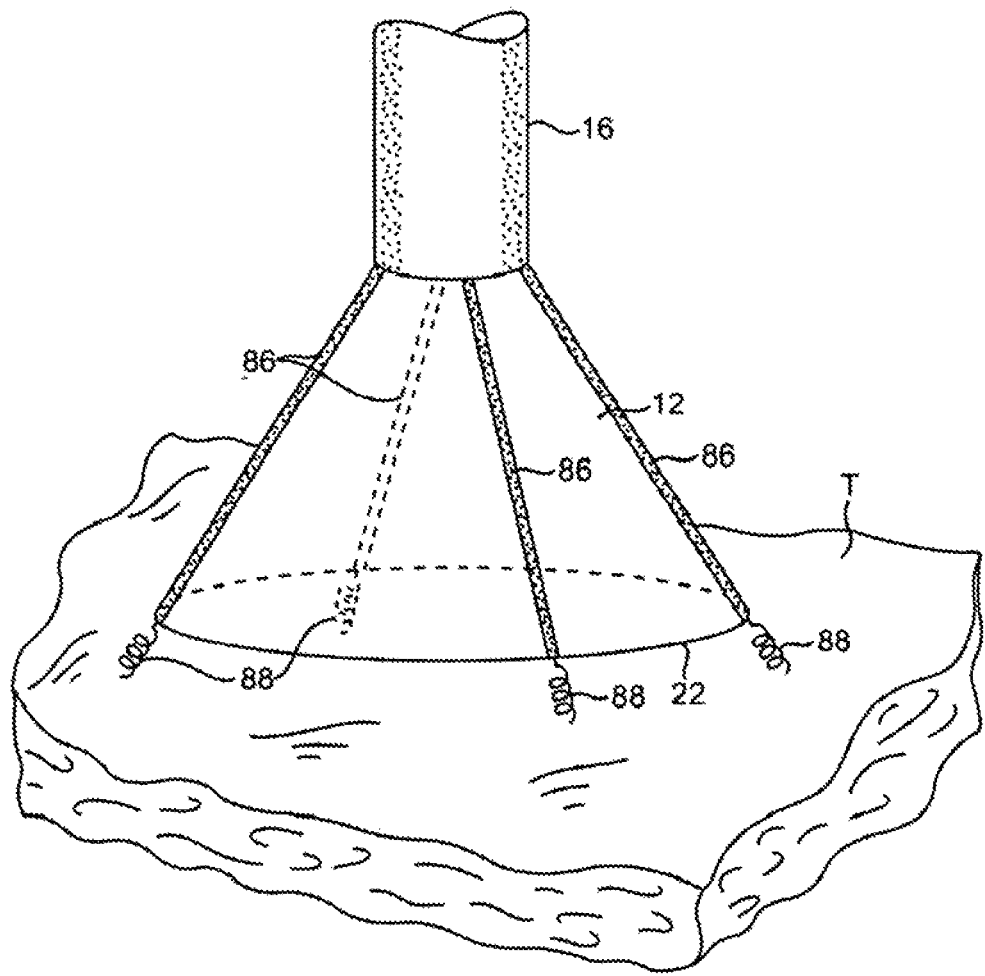
FIG. 7C shows another variation for anchoring the imaging hood having one or more tubular support members integrated with the imaging hood; each support members may define a lumen therethrough for advancing a helical tissue anchor within.

In another variation where the tool delivery catheter 82 may be omitted entirely to temporarily anchor imaging hood 12, FIG. 7C shows an imaging hood 12 having one or more tubular support members 86, e.g., four support members 86 as shown, integrated with the imaging hood 12. The tubular support members 86 may define lumens therethrough each having helical tissue engaging devices 88 positioned within. When an expanded imaging hood 12 is to be temporarily anchored to the tissue, the helical tissue engaging devices 88 may be urged distally to extend from imaging hood 12 and each may be torqued from its proximal end to engage the underlying tissue T. Each of the helical tissue engaging devices 88 may be advanced through the length of deployment catheter 16 or they may be positioned within tubular support members 86 during the delivery and deployment of imaging hood 12. Once the procedure within imaging hood 12 is finished, each of the tissue engaging devices 88 may be disengaged from the tissue and the imaging hood 12 may be repositioned to another region of tissue or removed from the patient body.

Figure 8A:
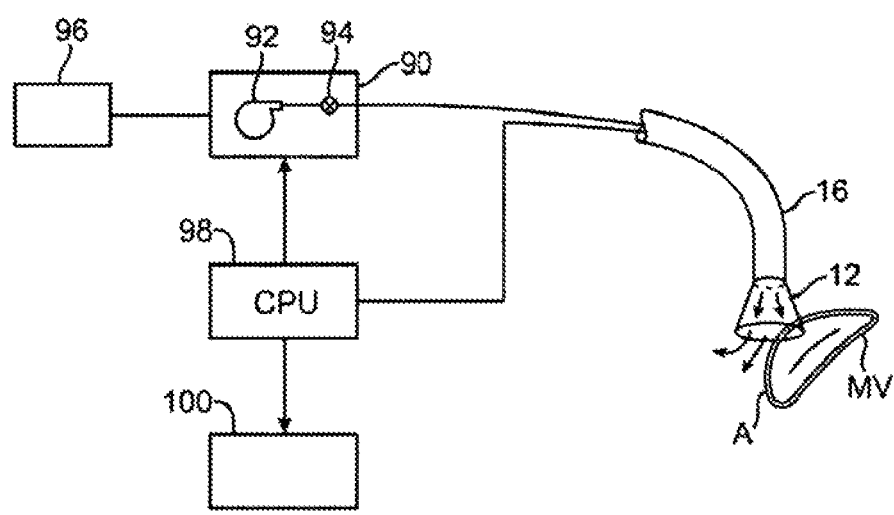
FIG. 8A shows an illustrative example of one variation of how a tissue imager may be utilized with an imaging device.

An illustrative example is shown in FIG. 8A of a tissue imaging assembly connected to a fluid delivery system 90 and to an optional processor 98 and image recorder and/or viewer 100. The fluid delivery system 90 may generally comprise a pump 92 and an optional valve 94 for controlling the flow rate of the fluid into the system. A fluid reservoir 96, fluidly connected to pump 92, may hold the fluid to be pumped through imaging hood 12. An optional central processing unit or processor 98 may be in electrical communication with fluid delivery system 90 for controlling flow parameters such as the flow rate and/or velocity of the pumped fluid. The processor 98 may also be in electrical communication with an image recorder and/or viewer 100 for directly viewing the images of tissue received from within imaging hood 12. Imager recorder and/or viewer 100 may also be used not only to record the image but also the location of the viewed tissue region, if so desired.

Optionally, processor 98 may also be utilized to coordinate the fluid flow and the image capture. For instance, processor 98 may be programmed to provide for fluid flow from reservoir 96 until the tissue area has been displaced of blood to obtain a clear image. Once the image has been determined to be sufficiently clear, either visually by a practitioner or by computer, an image of the tissue may be captured automatically by recorder 100 and pump 92 may be automatically stopped or slowed by processor 98 to cease the fluid flow into the patient. Other variations for fluid delivery and image capture are, of course, possible and the aforementioned configuration is intended only to be illustrative and not limiting.

Figure 8B:
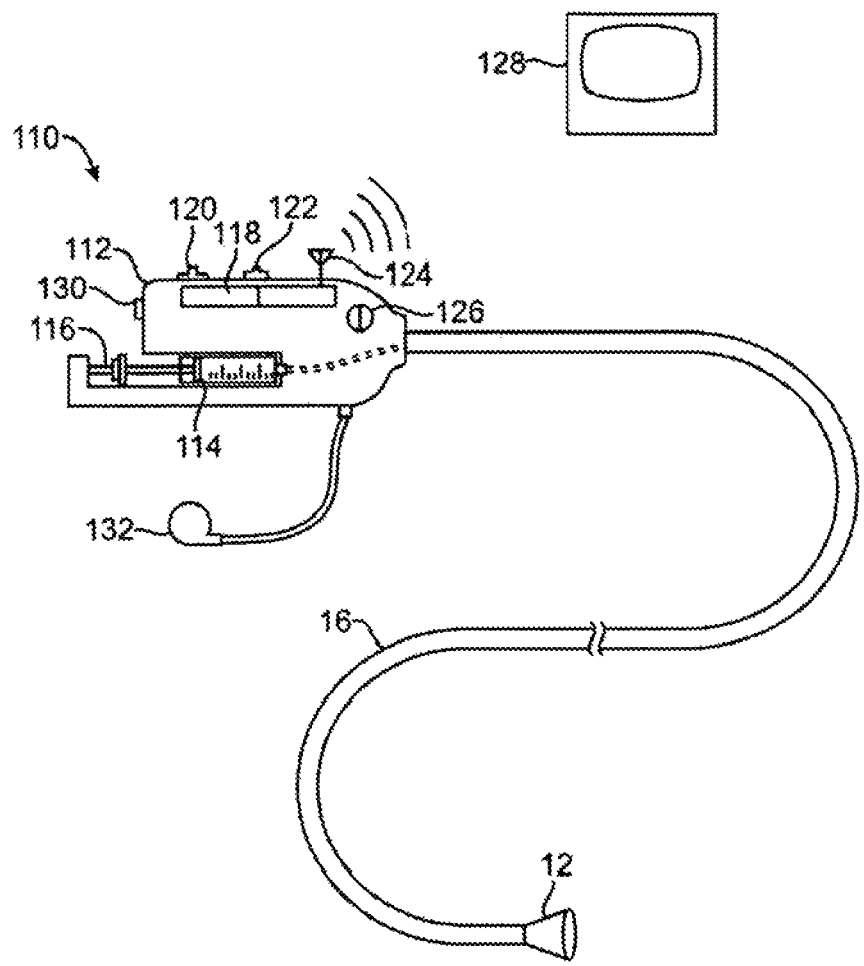
FIG. 8B shows a further illustration of a hand-held variation of the fluid delivery and tissue manipulation system.

FIG. 8B shows a further illustration of a hand-held variation of the fluid delivery and tissue manipulation system HO. In this variation, system 110 may have a housing or handle assembly 112 which can be held or manipulated by the physician from outside the patient body. The fluid reservoir 114, shown in this variation as a syringe, can be fluidly coupled to the handle assembly 112 and actuated via a pumping mechanism 116, e.g., lead screw. Fluid reservoir 114 may be a simple reservoir separated from the handle assembly 112 and fluidly coupled to handle assembly 112 via one or more tubes. The fluid flow rate and other mechanisms may be metered by the electronic controller 118.

Deployment of imaging hood 12 may be actuated by a hood deployment switch 120 located on the handle assembly 112 while dispensation of the fluid from reservoir 114 may be actuated by a fluid deployment switch 122, which can be electrically coupled to the controller 118. Controller 118 may also be electrically coupled to a wired or wireless antenna 124 optionally integrated with the handle assembly 112, as shown in the figure. The wireless antenna 124 can be used to wirelessly transmit images captured from the imaging hood 12 to a receiver, e.g., via Bluetooth® wireless technology (Bluetooth SIG, Inc., Bellevue, WA), RF, etc., for viewing on a monitor 128 or for recording for later viewing.

Articulation control of the deployment catheter 16, or a delivery catheter or sheath 14 through which the deployment catheter 16 may be delivered, may be accomplished by computer control, as described above, in which case an additional controller may be utilized with handle assembly 112. In the case of manual articulation, handle assembly 112 may incorporate one or more articulation controls 126 for manual manipulation of the position of deployment catheter 16. Handle assembly 112 may also define one or more instrument ports 130 through which a number of intravascular tools may be passed for tissue manipulation and treatment within imaging hood 12, as described further below. Furthermore, in certain procedures, fluid or debris may be sucked into imaging hood 12 for evacuation from the patient body by optionally fluidly coupling a suction pump 132 to handle assembly 112 or directly to deployment catheter 16.

Figure 9A:
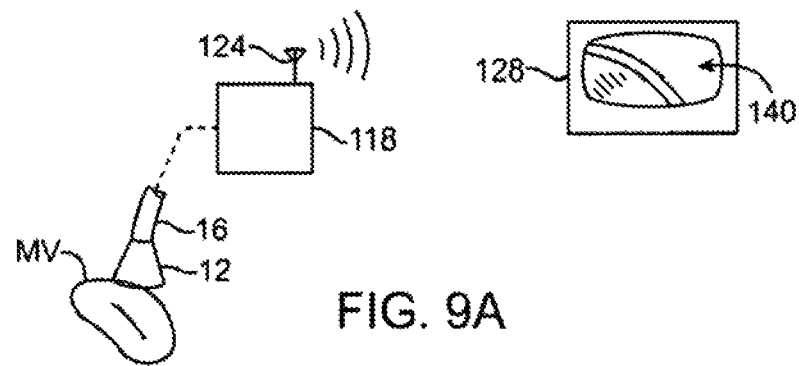
FIGS. 9A to 9C illustrate an example of capturing several images of the tissue at multiple regions.
Figure 9B:
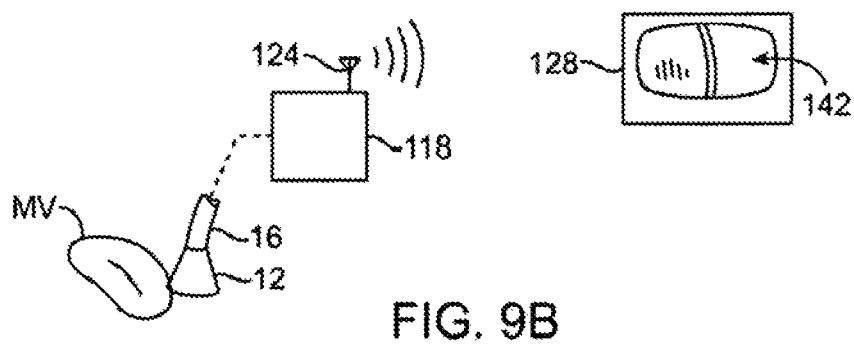
Figure 9C:
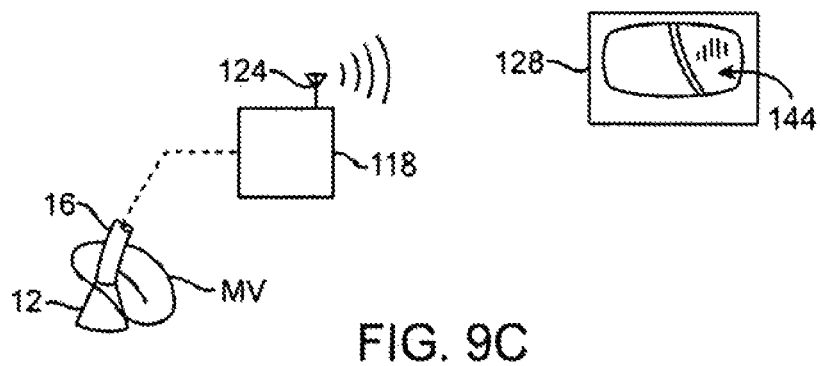

As described above, fluid may be pumped continuously into imaging hood 12 to provide for clear viewing of the underlying tissue. Alternatively, fluid may be pumped temporarily or sporadically only until a clear view of the tissue is available to be imaged and recorded, at which point the fluid flow may cease and the blood may be allowed to seep or flow back into imaging hood 12. FIGS. 9A to 9C illustrate an example of capturing several images of the tissue at multiple regions. Deployment catheter 16 may be desirably positioned and imaging hood 12 deployed and brought into position against a region of tissue to be imaged, in this example the tissue surrounding a mitral valve MV within the left atrium of a patient's heart. The imaging hood 12 may be optionally anchored to the tissue, as described above, and then cleared by pumping the imaging fluid into the hood 12. Once sufficiently clear, the tissue may be visualized and the image captured by control electronics 118. The first captured image 140 may be stored and/or transmitted wirelessly 124 to a monitor 128 for viewing by the physician, as shown in FIG. 9A.

The deployment catheter 16 may be then repositioned to an adjacent portion of mitral valve MV, as shown in FIG. 9B, where the process may be repeated to capture a second image 142 for viewing and/or recording. The deployment catheter 16 may again be repositioned to another region of tissue, as shown in FIG. 9C, where a third image 144 may be captured for viewing and/or recording. This procedure may be repeated as many times as necessary for capturing a comprehensive image of the tissue surrounding mitral valve MV, or any other tissue region. When the deployment catheter 16 and imaging hood 12 is repositioned from tissue region to tissue region, the pump may be stopped during positioning and blood or surrounding fluid may be allowed to enter within imaging hood 12 until the tissue is to be imaged, where the imaging hood 12 may be cleared, as above.

As mentioned above, when the imaging hood 12 is cleared by pumping the imaging fluid within for clearing the blood or other bodily fluid, the fluid may be pumped continuously to maintain the imaging fluid within the hood 12 at a positive pressure or it may be pumped under computer control for slowing or stopping the fluid flow into the hood 12 upon detection of various parameters or until a clear image of the underlying tissue is obtained. The control electronics 118 may also be programmed to coordinate the fluid flow into the imaging hood 12 with various physical parameters to maintain a clear image within imaging hood 12.

Figure 10A:
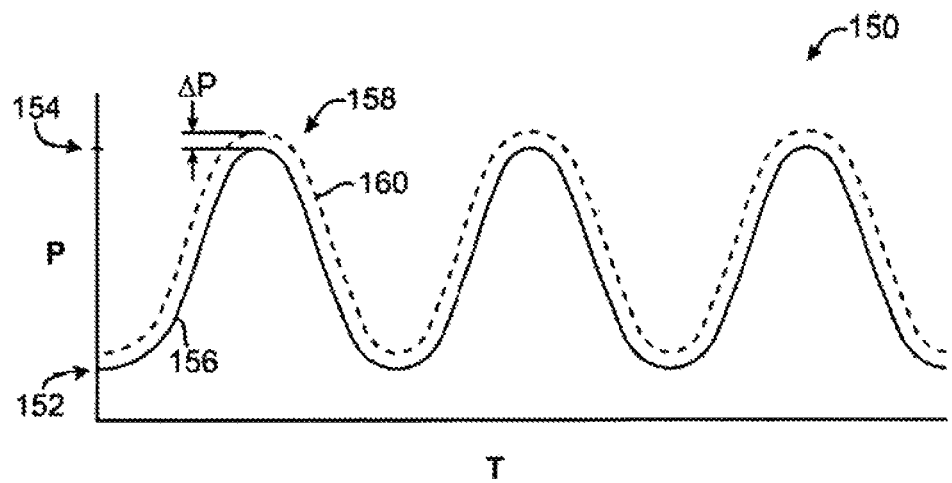
FIGS. 10A and 10B show charts illustrating how fluid pressure within the imaging hood may be coordinated with the surrounding blood pressure; the fluid pressure in the imaging hood may be coordinated with the blood pressure or it may be regulated based upon pressure feedback from the blood.

One example is shown in FIG. 10A which shows a chart 150 illustrating how fluid pressure within the imaging hood 12 may be coordinated with the surrounding blood pressure. Chart 150 shows the cyclical blood pressure 156 alternating between diastolic pressure 152 and systolic pressure 154 over time T due to the beating motion of the patient heart. The fluid pressure of the imaging fluid, indicated by plot 160, within imaging hood 12 may be automatically timed to correspond to the blood pressure changes 160 such that an increased pressure is maintained within imaging hood 12 which is consistently above the blood pressure 156 by a slight increase $\Delta P$, as illustrated by the pressure difference at the peak systolic pressure 158. This pressure difference, $\Delta P$, may be maintained within imaging hood 12 over the pressure variance of the surrounding blood pressure to maintain a positive imaging fluid pressure within imaging hood 12 to maintain a clear view of the underlying tissue. One benefit of maintaining a constant $\Delta P$ is a constant flow and maintenance of a clear field.

Figure 10B:
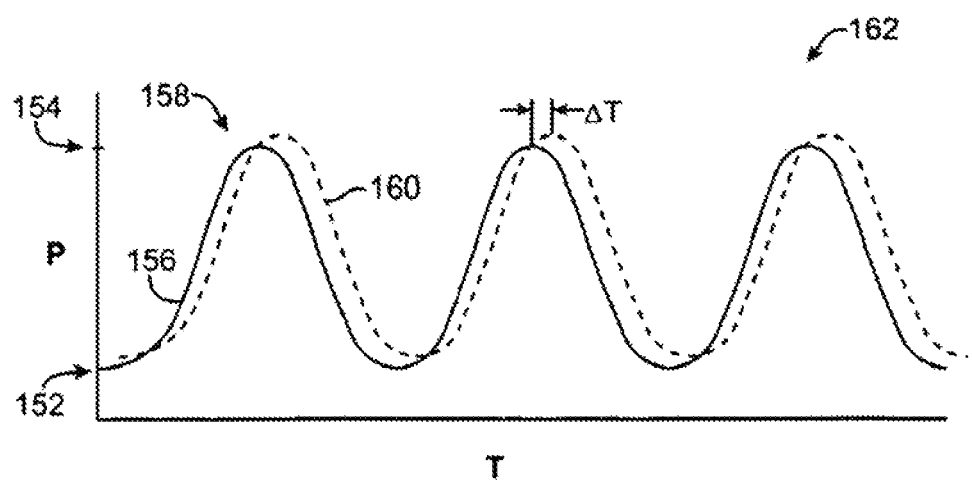

FIG. 10B shows a chart 162 illustrating another variation for maintaining a clear view of the underlying tissue where one or more sensors within the imaging hood 12, as described in further detail below, may be configured to sense pressure changes within the imaging hood 12 and to correspondingly increase the imaging fluid pressure within imaging hood 12. This may result in a time delay, $\Delta T$, as illustrated by the shifted fluid pressure 160 relative to the cycling blood pressure 156, although the time delays $\Delta T$ may be negligible in maintaining the clear image of the underlying tissue. Predictive software algorithms can also be used to substantially eliminate this time delay by predicting when the next pressure wave peak will arrive and by increasing the pressure ahead of the pressure wave's arrival by an amount of time equal to the aforementioned time delay to essentially cancel the time delay out.

The variations in fluid pressure within imaging hood 12 may be accomplished in part due to the nature of imaging hood 12. An inflatable balloon, which is conventionally utilized for imaging tissue, may be affected by the surrounding blood pressure changes. On the other hand, an imaging hood 12 retains a constant volume therewithin and is structurally unaffected by the surrounding blood pressure changes, thus allowing for pressure increases therewithin. The material that hood 12 is made from may also contribute to the manner in which the pressure is modulated within this hood 12. A stiffer hood material, such as high durometer polyurethane or Nylon, may facilitate the maintaining of an open hood when deployed. On the other hand, a relatively lower durometer or softer material, such as a low durometer PVC or polyurethane, may collapse from the surrounding fluid pressure and may not adequately maintain a deployed or expanded hood.

In further controlling the flow of the purging fluid within the hood 12, various measures may be taken in configuring the assembly to allow for the infusion and controlled retention of the clearing fluid into the hood. By controlling the infusion and retention of the clearing fluid, the introduction of the clearing fluid into the patient body may be limited and the clarity of the imaging of the underlying tissue through the fluid within the hood 12 may be maintained for relatively longer periods of time by inhibiting, delaying, or preventing the infusion of surrounding blood into the viewing field.

In utilizing the hood 12 and various instruments through the hood for tissue treatment, hood 12 may be articulated in a variety of configurations to facilitate the access to regions within the heart. For instance, access to the left atrium of a patient's heart for performing treatments such as tissue ablation for atrial fibrillation may require hood 12 to be retroflexed in various configurations to enable sufficient access. Thus, the ability to control the steering or articulation of hood 12 within the patient's heart may facilitate tissue visualization and treatment.

Figure 11A:
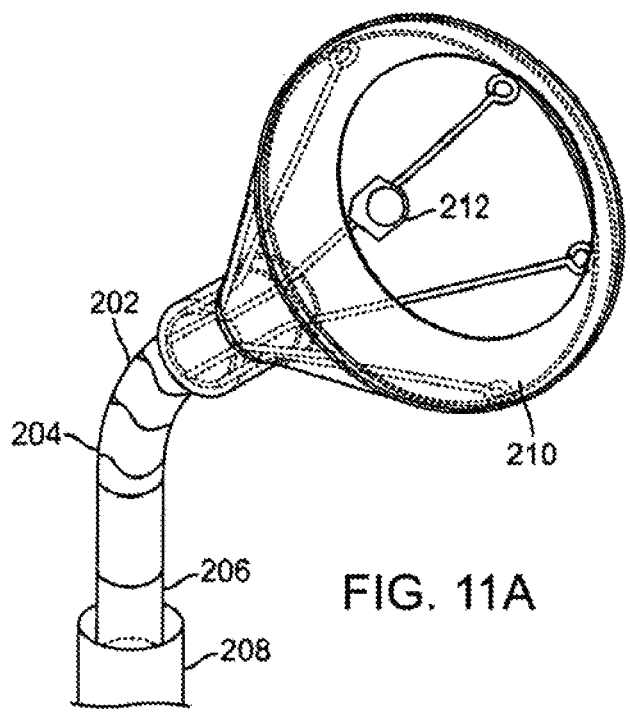
FIG. 11A shows a perspective view of a variation of the tissue visualization catheter with a steerable distal portion.

FIG. 11A shows a variation of the tissue visualization catheter with an example of steering features. As shown in FIG. 11A, one variation of the visualization catheter may comprise a tubular member such as an extrusion 206 (which may define a multi-lumen extrusion) and a steerable segment 202 distal to extrusion 206 with hood 210 coupled to and extending distally from the steerable segment 202. An imaging element 212 is also found in hood 210 where the imaging element can be a CMOS or CCD camera with light source, as described above. The imaging element 212 can also be a high resolution optical fiber scope (with light source) positioned in one of the channels of the multi-lumen extrusion 206. The visualization catheter may be further translated along a single lumen catheter sheath 208 that allows the visualization catheter to retract into or be deployed from the catheter sheath 208. The steerable segment 202 of the catheter may be also coated with a thin liner 204 to ensure the surface of the steerable segment remains smooth and atraumatic to surrounding tissues.

Further details of such a visualization catheter and methods of use are shown and described in U.S. Pat. Pub. 2006/0184048 A1, which is incorporated herein by reference in its entirety.

Figure 11B:
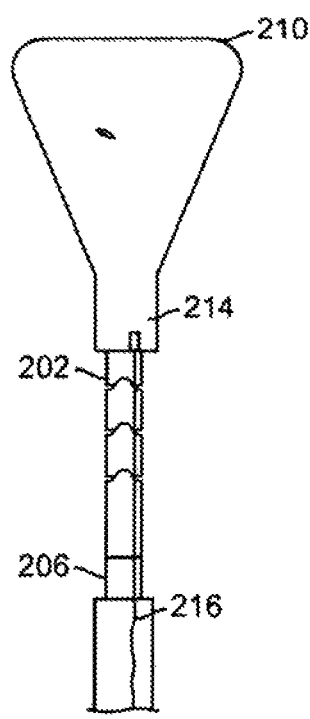
FIG. 11B shows the side view of the same device controlled by a single pull wire.
Figure 11C:
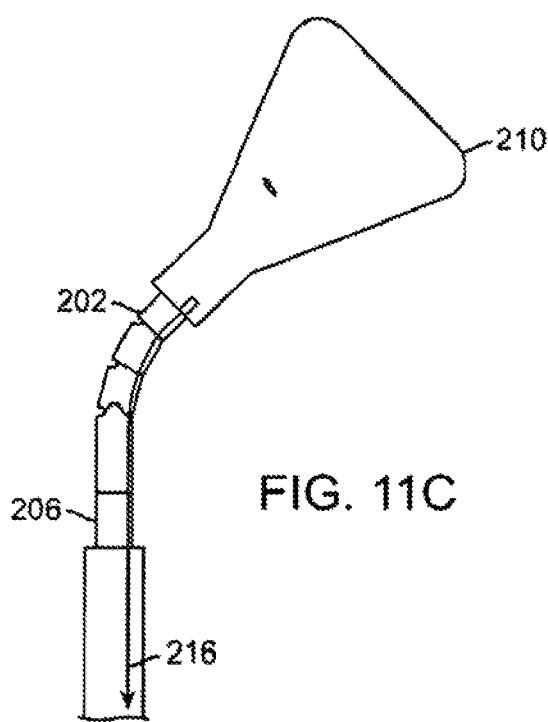
FIG. 11C shows the side view of the same device with the pull wire tensioned to steer the steerable segment into a curved configuration.

FIG. 11B and FIG. 11C illustrates an example of the visualization catheter being steered by a pull wire mechanism. A pull wire 216 passing through extrusion 206 and steerable segment 202 may be terminated at distal section 214 of steerable segment 202. The proximal end of pull wire 216 may be routed into a handle at the proximal end of extrusion 206. As shown in FIG. 11C, the steerable segment 202 is steered into a curved configuration when the pull wire 216 is tensioned from its proximal end. The interaction between the tensioning and the bending of steerable segment 202 of the catheter enables the hood 210 to articulate across a range of angles. The pull wire 216 can be made from stainless steel, nitinol, elgiloy, tungsten, etc.

Shown in FIG. 11D, by combining torquing of the visualization catheter about the longitudinal axis of the extrusion, hood 210 may be rotated in various directions 218 and 220 to access more areas with the steering segment 202.

Figures 12A, 12B:
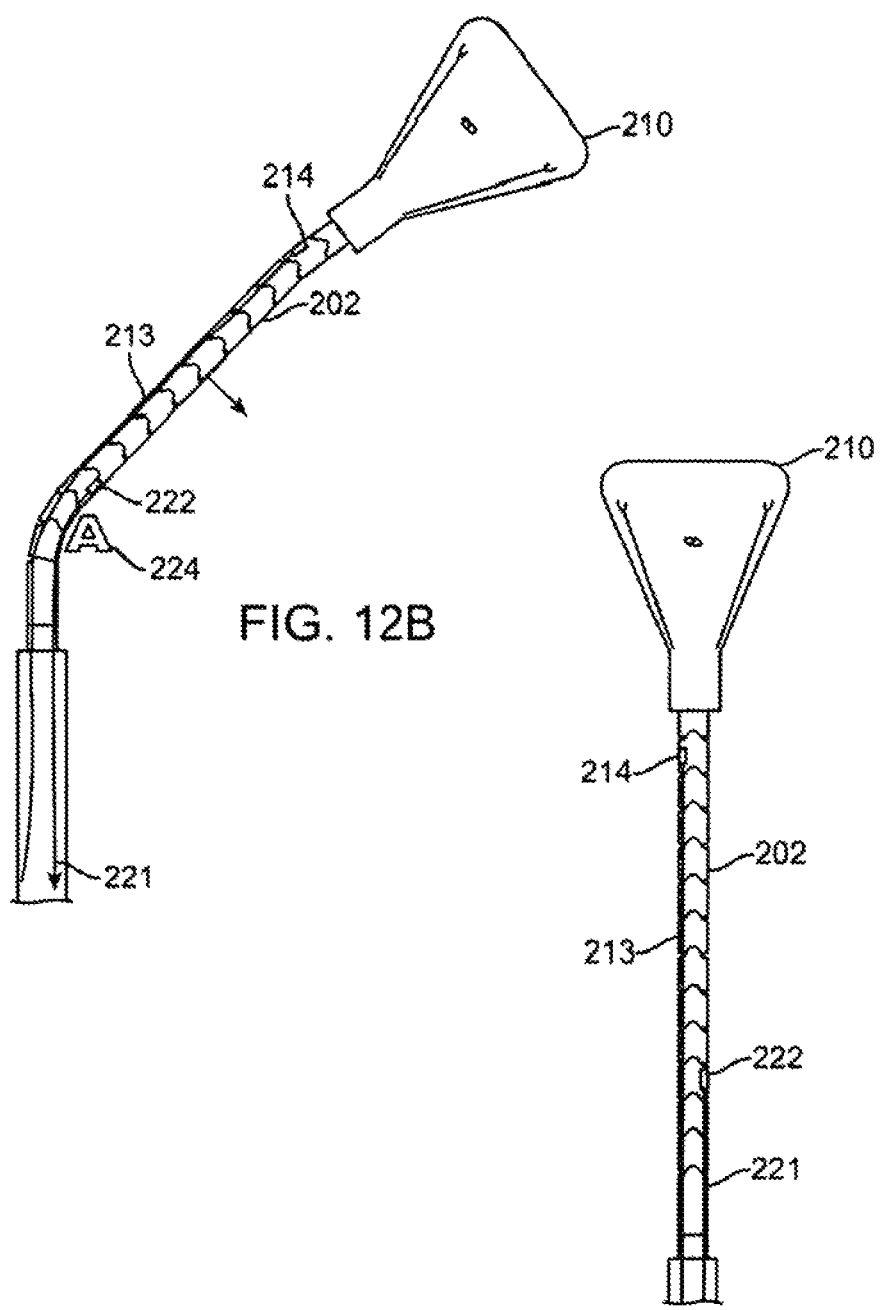
FIG. 12A shows the side view of another variation of the steerable tissue visualization catheter with two pull wires.
FIG. 12B shows the side view of the same device with the right proximal pull wire tensioned.

FIG. 12A shows a similar embodiment with a double pull wire mechanism to steer the tissue visualization catheter into a double-bend configuration. As shown, a first pull wire 213 may be terminated at a first location 214 along the steerable segment 202 proximal to hood 210 while a second pull wire 221 may be terminated at a second location 222 along steerable segment 202 proximal to the first location 214. The first and second locations 214, 222 may both be located along segment 202 so long as they are staggered with respect to one another. Moreover, they may terminate along opposite angles of segment 202 to provide opposing bending moments, as described further below. When second pull wire 221 is tensioned, as shown FIG. 12B, hood 210 and segment 202 may be curved in a first direction with respect to a longitudinal axis of the sheath. First pull wire 213 may also be tensioned (before, after, or simultaneously with second pull wire 221) such that steerable segment 202 is articulated into a double-bend configuration, as shown in FIG. 12C, where a first curve 224 (defined as Curve A) is curved in an opposite direction from second curve 226 (defined as Curve B). Although hood 210 is illustrated in a perpendicular angle relative to the sheath, the degree of tensioning of pull wires 213, 221 may be varied to result in a variable angle which hood 210 may be configured.

Figure 12D:
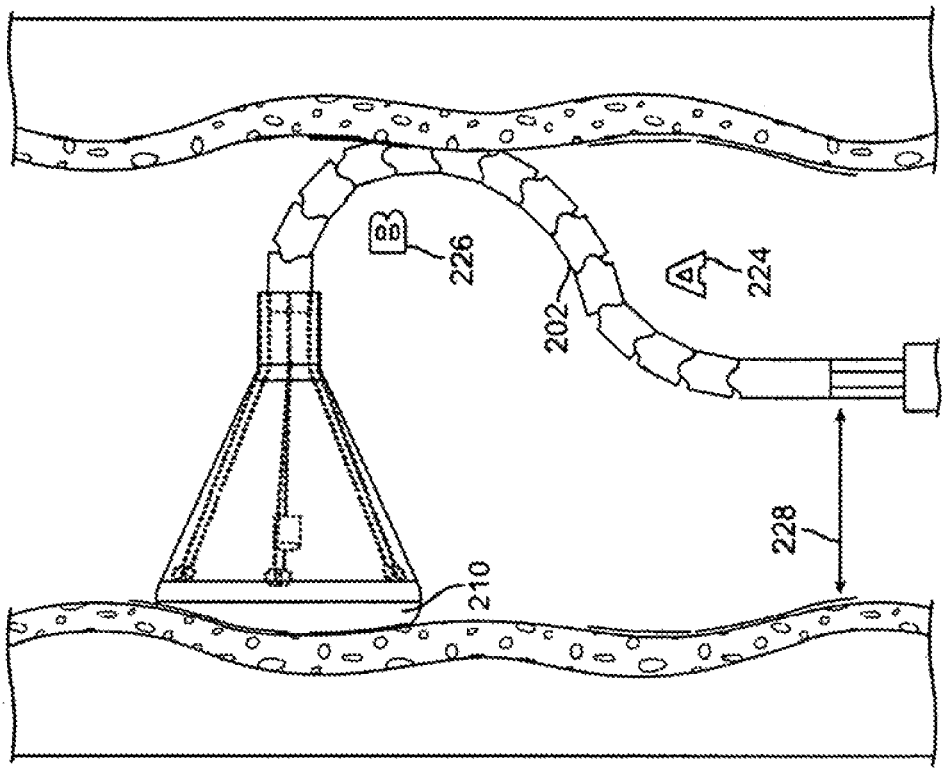
FIG. 12D shows the side view of the same device positioned against tissue at an angle, e.g., perpendicularly, within a tight lumen or space.
Figure 12C:
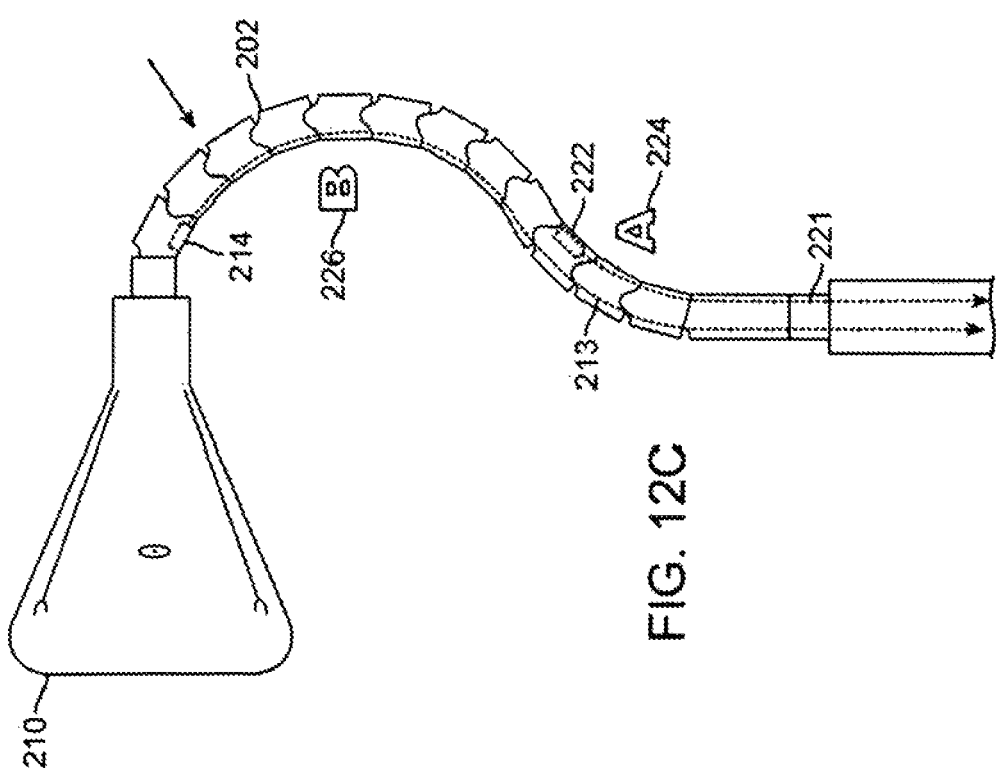
FIG. 12C shows the side view of the same device with the left distal pull wire tensioned to create a double curve section along the steerable segment of the catheter.

FIG. 12D illustrates the articulated deployment catheter of FIG. 12C positioned within a body lumen where hood 210 is accessing a target tissue along a relatively narrow region. To access the target tissue, first curve 224 and second curve 226 may be actuated to position hood 210 in a perpendicular configuration relative to the sheath. The proximal portion of the deployment catheter and the sheath may be maintained a distance 228 from a surface of the tissue to be visualized and/or treated while the dual-curved configuration also allows segment 202 to maintain a gentle bend radius throughout even if a relatively tight perpendicular bend is attained.

Figure 13A:
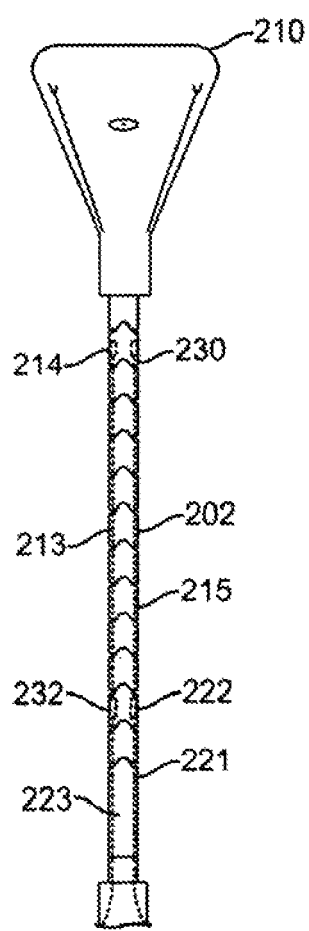
FIG. 13A shows the side view of a variation of the steerable tissue visualization catheter with 4 pull wires.

FIG. 13A shows another variation of the steerable tissue visualization catheter with 2 pairs of pull wires terminated distally and proximally along steerable segment 202 of the catheter. First pull wire 213 and second pull wire 221 may be positioned and terminated as above, and third pull wire 215 may extend distally along segment 202 to terminate at third location 230 proximal to hood 210 and adjacent to first location 214 along an opposing side of segment 202 relative to first location 214. Fourth pull wire 223 may extend along segment 202 and terminate at fourth location 232 which is adjacent to second location 222 along an opposing side of segment 202.

Figure 13B:
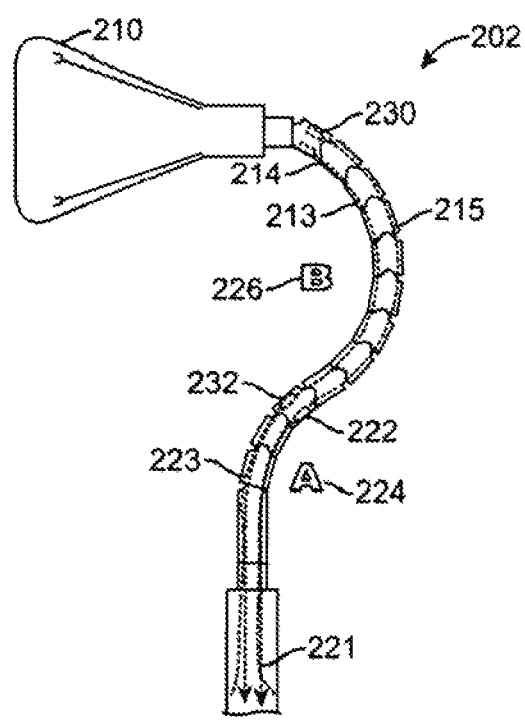
FIG. 13B shows the side view of the same device configured into a double bend defined by curve A and curve B.
Figure 13D:
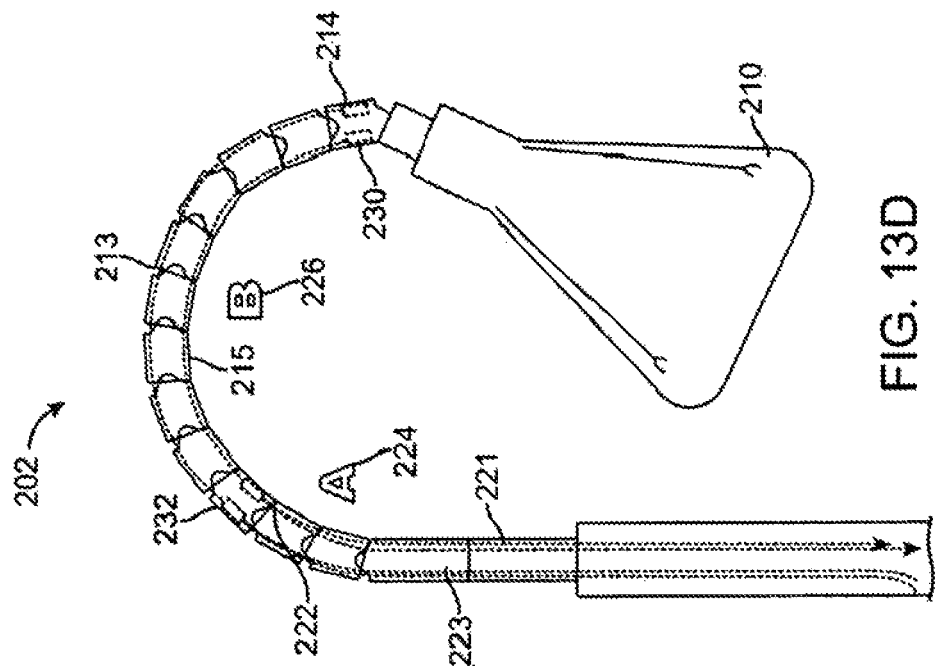
FIG. 13D shows the side view of the same device doing a retroflex bend when both curve A and curve B are curved along the same side.
Figure 13C:
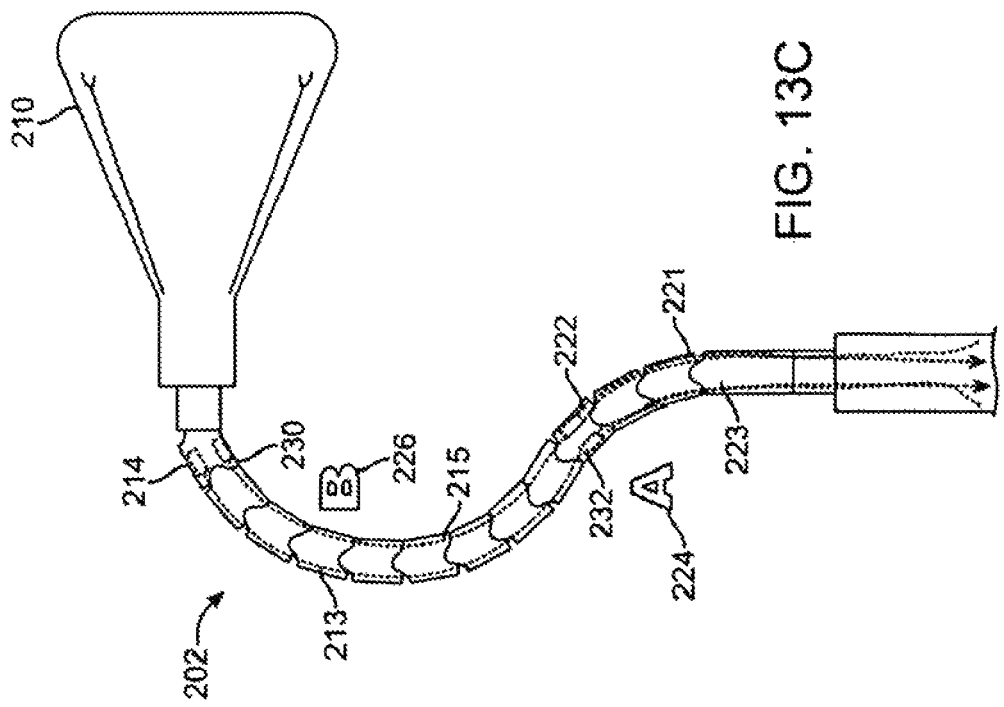
FIG. 13C shows the side view of the same device configured into a double bend defined by curve A and curve B in a direction opposite to that shown in FIG. 13B.

First pull wire 213 and second pull wire 221 may be tensioned to articulate segment 202 and hood 210 in a configuration where first curve 224 and second curve 226 are aligned in opposing directions, as above and as shown in FIG. 13B. Third and fourth pull wires 215 and 223 may remain slack during this articulation. However, rather than torquing segment 202 and hood 210 around to reposition hood 210 along an opposite side, first and second pull wires 213 and 221 may be released and third and fourth pull wires 215 and 223 may be tensioned to articulate hood 210 in an opposing direction, as illustrated in FIG. 13C. Alternatively, in actuating pull wires located along a common side of segment 202, e.g., third pull wire 215 and second pull wire 221 as shown in FIG. 13D, segment 202 may be articulated to fully retroflex hood 210 proximally relative to a longitudinal axis of the deployment catheter. Although four separate pull wires are illustrated, fewer than or greater than four pull wires may be utilized and positioned along segment 202 depending upon the desired degree of articulation.

The pullwire mechanism can also interact to produce push steering motions as shown in FIGS. 13E and 13F where hood 210 may be placed against the tissue surface to be visualized and/or treated and the pull wires may be tensioned in a manner to push or urge hood 210 into direct intimate contact against the tissue surface. This can be achieved, for instance, by tensioning the appropriate pull wires to articulate hood 210 in a perpendicular angle, as described above and as shown in the side view of FIG. 13E. With hood 210 initially positioned along the tissue surface to be visualized and/or treated, pull wires 213, 221 may be tensioned and locked in place, as shown in FIG. 13G. The pushing motion of hood 210 can be defined as the reduction of first curve 224 while the steerable segment 202 remains rigid in a double bend configuration.

Figures 14A, 14B:
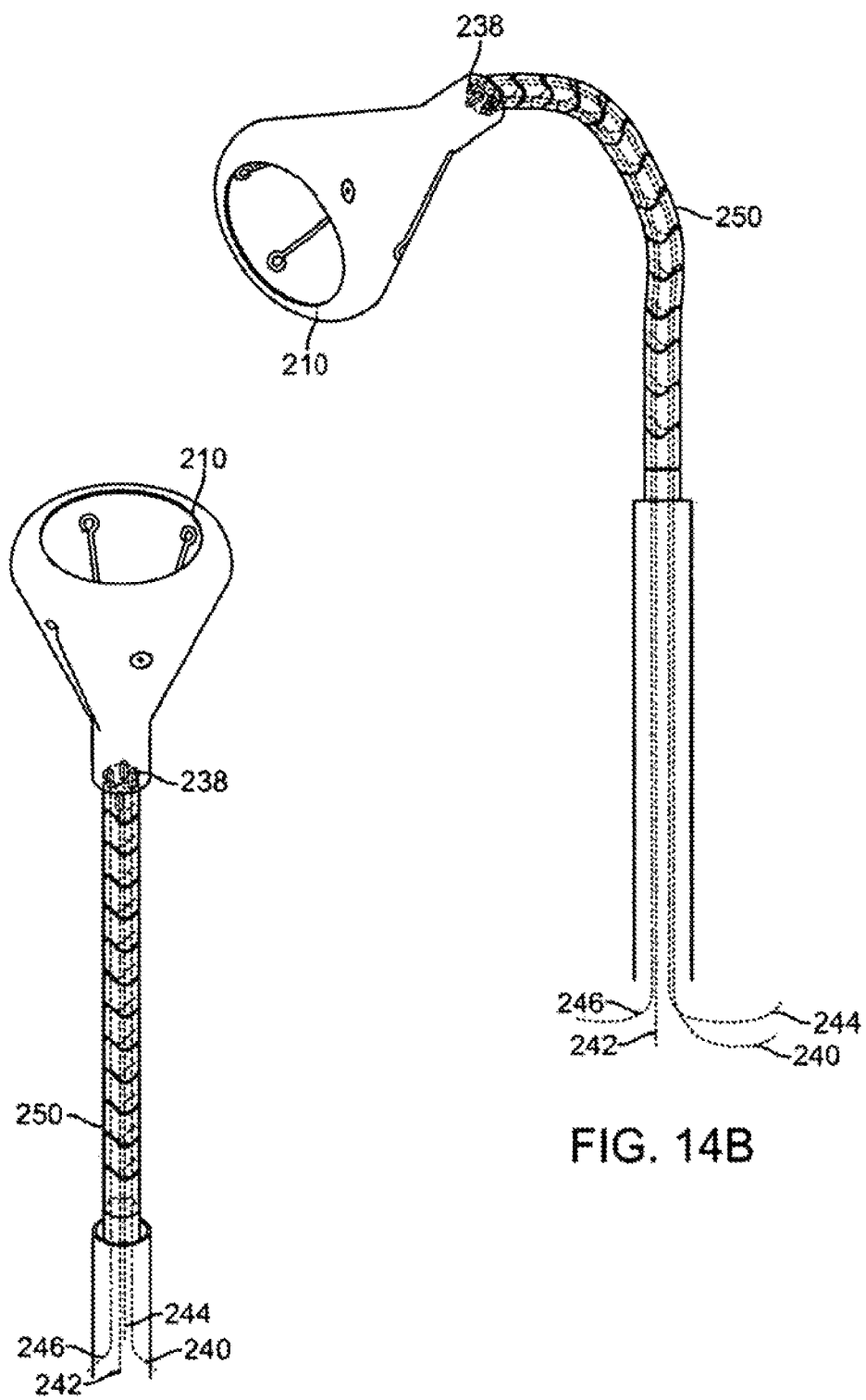
FIG. 14A shows the perspective view of a variation of the tissue visualization catheter with multiple pull wires to articulate hood in multiple directions without the need to torque the catheter.
FIG. 14B shows the perspective view of the same device with hood articulatable in multiple directions.

FIGS. 14A to 14E illustrate another variation of a pull wire mechanism where multiple pull wires, four in this instance, are attached at a distal location 238 of steerable segment 250 proximal to hood 210. The pull wires may be positioned around a segment 250 uniformly spaced apart from one another. Thus, first pull wire 240, second pull wire 242, third pull wire 244, and fourth pull wire 246 may be aligned parallel to another and terminate at a common location 238 such that tensioning each of the pull wires allows for segment 250 and hood 210 to be articulated accordingly. With each pull wire relaxed, as shown in FIG. 14A, hood 210 may extend distally while tensioning second and or fourth pull wires 242 and 246 may articulate hood 210 to curve appropriately, as shown in FIG. 14B. Likewise, tensioning first and/or third pull wires 240 and 244 may articulate hood 210 in a second direction, as shown in FIG. 14C and tensioning of second and/or third pull wires 242 and 244 or tensioning of first and/or fourth pull wires 240 and 246 may articulate hood 210 accordingly, as shown in FIGS. 14D and 14E. Various combinations of tensioning various pull wires may accordingly effect any number of configurations for hood 210.

Figure 15C:
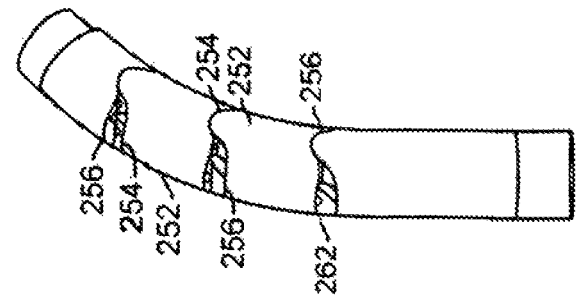
FIG. 15C shows the perspective view of a plurality of links connected in series together.
Figure 15B:
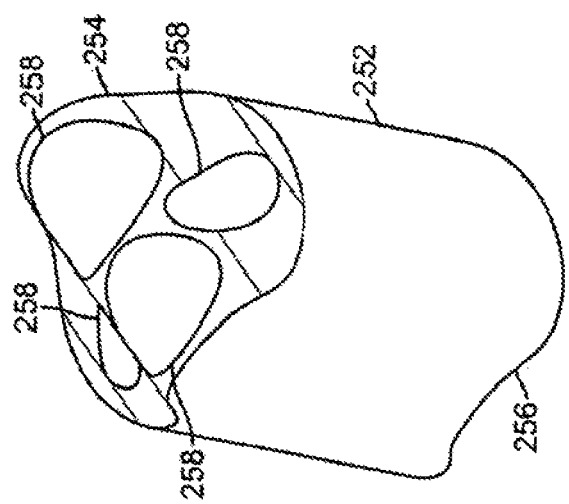
FIG. 15B shows the perspective view of a contoured link, e.g., bump link.
Figure 15A:
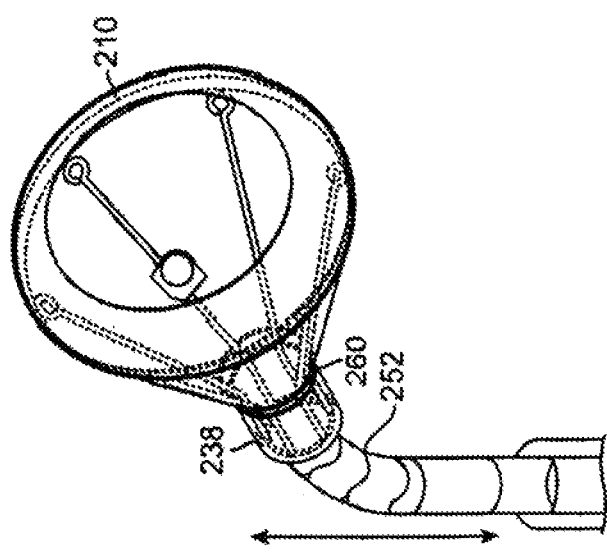
FIG. 15A shows the perspective view of a variation of the tissue visualization catheter with serially aligned multiple links which are steerable.

Turning now to the articulatable segments, various types of links may be utilized to affect a corresponding articulation. For example, FIG. 15A shows a perspective view of a variation of the tissue visualization catheter where the steerable segment may utilize serially aligned multiple links which collectively facilitate hood articulation. This particular variation illustrates the use of contoured links 252, e.g., "bump" links as shown in the perspective view of FIG. 15B, which define a distal curved surface 254, e.g., convex in shaped, and a proximal curved surface 256, e.g., concave in shape, such that when serially aligned with a similar link, the curved convex distal surface 254 of one link mates correspondingly with the curved concave proximal surface 256 of the adjacent link and allows the relative pivoting or rocking between the adjacent links along a defined plane, as shown in the detail side view of FIG. 15C.

Each of the links 252 may define one or more channels 258 therethrough such that when a plurality of links 252 are aligned and mated to one another, each individual channel 258 forms a continuous lumen through the segment. A lining 262, such as an elastic heat shrink polymer, may be coated upon the link segments to ensure a smooth surface along the links. Moreover, the links can be made from materials such as stainless steel, PEEK, hard plastics, etc., and manufactured through machining, molding, metal injection molding, etc.

FIGS. 15D to 15F illustrate side views of the serially aligned link 252 in a straightened configuration, as shown in FIG. 15D, as well as articulated in a compound curve, as shown in FIG. 15E, or a single curve, as shown in FIG. 15F, where each link is illustrated as pivoting or rocking with respect to an adjacent link. Additionally, once the terminal extent of the relative pivoting or angling between adjacent links is reached, the extent of the curvature is reached as well, as shown in the figures.

Figure 16A:
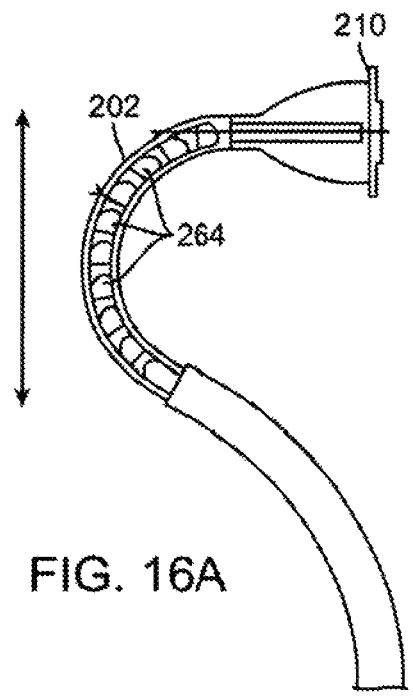
FIG. 16A shows the side view of a variation of the tissue visualization catheter with steerable pinned links.
Figure 16B:
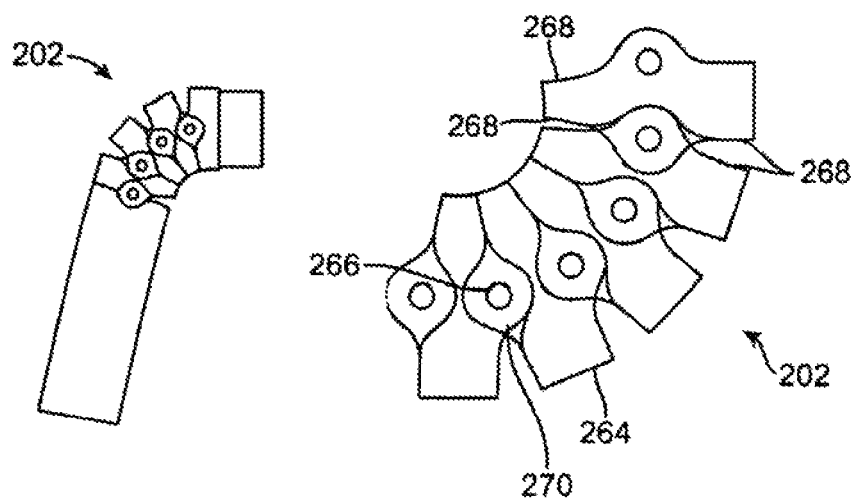
FIG. 16B shows the close up side view of pinned links.

FIG. 16A shows another variation of links which may be utilized for facilitating the articulation of segment 202. In this example, rather than utilizing contoured "bump" links, pinned links 264 may be utilized. FIG. 16B illustrates detail side views of pinned links 264, each of which may form a proximal and distal recessed surface with an intersecting interface 270 extending axially from both sides of an individual link 264. This interface 270 may extend and overlap with an adjacent link such that the overlapping interfaces may be aligned and pivotably connected to one another via a pin 266. Rather sliding along curved interface surfaces, pinned links 264 may pivot about the axis of the pins 266 to collectively form a segment 202 which is constrained to articulate in a single preset plane. Similar to contoured links, pinned links 264 may define one or more continuous lumens.

Moreover, pinned links 264 may be steerable via any of the pullwire mechanisms described above.

Additionally, pin linked steerable segments 264 may provide better control in the movement of the links as compared to other contoured links as pin links are constrained to pivot about a secured point instead of sliding along curve intersections. In addition, with pins 266 securing each adjacent link 264, compound curves created by the steerable segment 202 may be relatively more rigid which in turn may provide a more secure platform for force transmission when utilizing instruments positioned therethrough. Moreover, pinned links 264 may also be utilized for constructing steerable introducer sheaths.

FIG. 17A shows yet another variation of the steerable segment 202 comprised of ring links 272. As shown in the detail perspective views of FIG. 17B, circular ring links 272 may be comprised of a tubular member defining an opening therethrough. A distal edge 274 of link 272 may be chamfered such that this chamfered edge 274 is slidingly received in the proximal opening of an adjacent link. Because adjacent links 272 may slide freely with respect to one another, various angles and configurations may be formed. Circular ring links 272 may form complex rigid bends when pull wires are simultaneously tensioned. Other configurations that are not depicted are also possible with any of the link various combined in alternate configurations. The ring link embodiment can also be utilized as part of the introducer sheath to produce steerable sheaths. Similar to contoured links and pinned links, ring links can be made from materials such as, but not limited to, stainless steel, PEEK, hard plastics, etc. Moreover, rings links can be manufactured through machining, molding, metal injection molding, etc.

In addition, simultaneously tensioning all pull wires threaded along ring links 272 will compress each ring tightly towards each another to form a rigid segment. The rigid segment formed by the tensioned ring links may therefore "memorize" the current path taken by the catheter or sheath 276 and hold the catheter or sheath along this set trajectory to provide for effective force transmission for tools deployed through the catheter.

Figure 18:
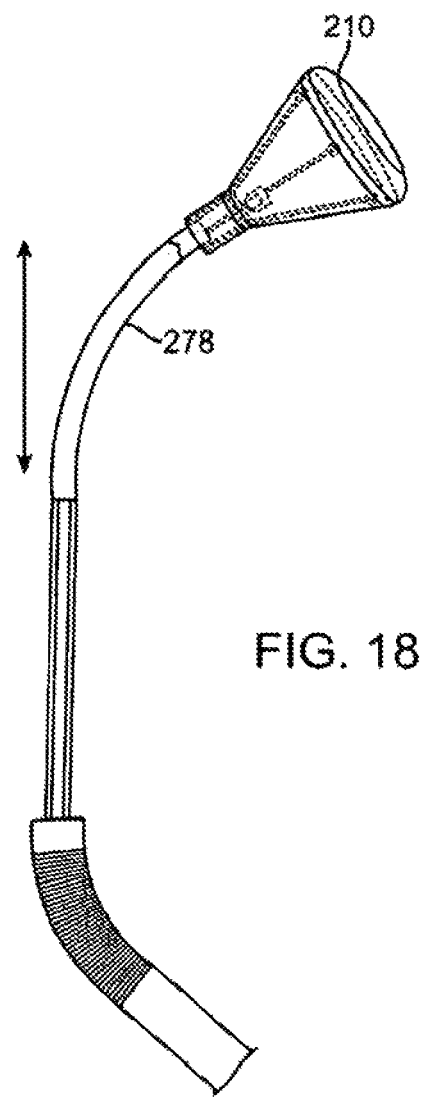
FIG. 18 shows the side view of a variation of the tissue visualization catheter with the steerable section made from a laser-cut shaft.

FIG. 18 shows a side view of another variation of a steerable segment 278 made from a cut tube, e.g., a laser-cut tube, having one or more pull wires therethrough. The laser cut tube 278 can be made from materials as described above and cut such that structural spines are formed along the outer bend radius of the steerable segment 278 to provide a more stable curved platform. A combination of different positions of such structural spines may yield steerable segments having a combination of different bend directions and/or bend radius.

Figures 19A, 19B:
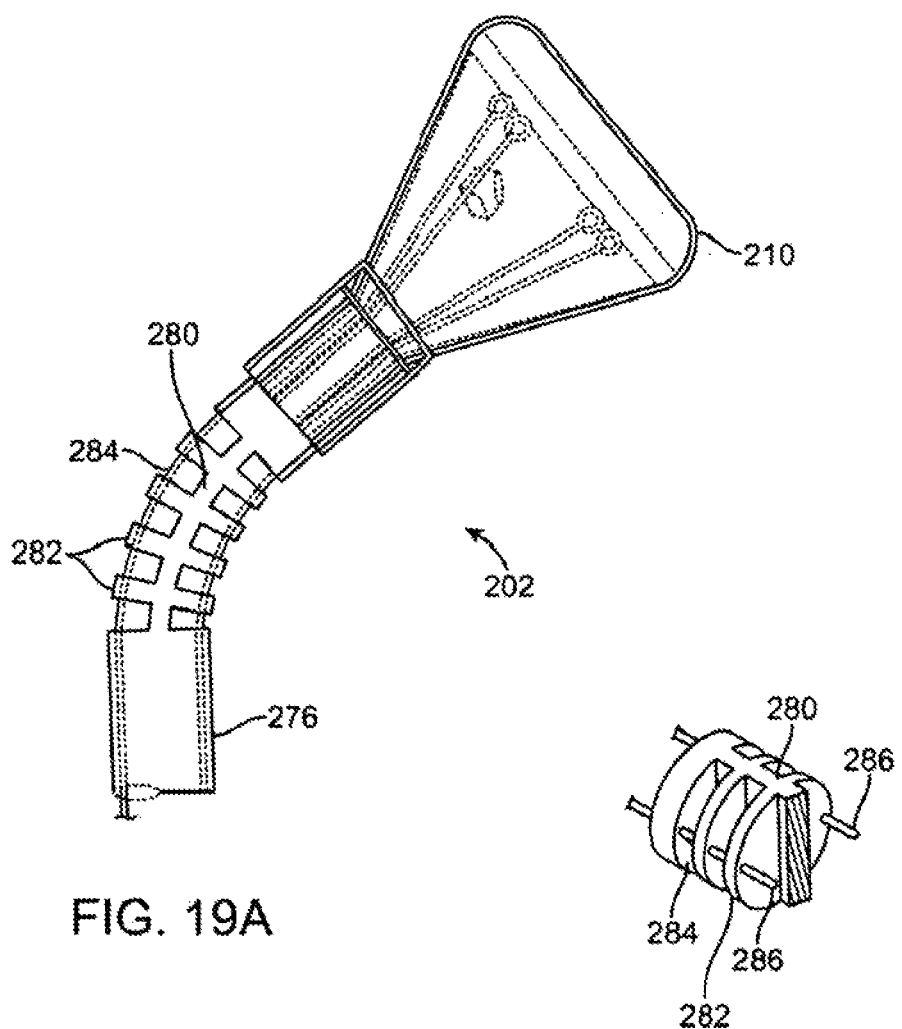
FIG. 19A shows the top view of a steerable tissue visualization catheter with steerable segment made up of a ribbed spine, e.g., "fish bone" shaped.
FIG. 19B illustrates a detail perspective view of a portion of the steerable segment with one or more pull wires extending therethrough.

FIG. 19 shows a side and perspective view of another steerable segment 202 that comprises a ribbed spine, e.g., a "fish bone" configuration. A continuous spine 280 may provide overall cohesive structural strength to the segment with ribbed extensions 282 extending perpendicularly from the spine 280 with gaps 284 formed at regular intervals between the extensions 282 to provide for flexibility of the segment. One or more pull wires 286 may extend through the segment through the ribbed extensions 282, as illustrated in the perspective detail view of FIG. 19B. Moreover, the ribbed extensions 282 can be arranged at different angles about the central longitudinal axis of the deployment catheter to yield steering along different predefined directions.

In yet another variation, the steerable segment 202 may comprise an extrusion having a plurality of slits or cuts 288 made along one or both sides of the segment 202 such that the slits 288 facilitate the bending of segment 202, as shown in the perspective and side views of FIGS. 20A and 20B. The resulting segment 202 results in the slits or cuts 288 formed along the inner radius of a desired direction of bend. Hence, when pull wires are tensioned through segment 202, the steerable segment 202 may bend in the direction of the slit patterns when the pullwires are pulled. FIG. 20C illustrates a detail side view of slits 288 showing the removed portion of material along segment 202. Aside from slits or cuts, grooves, channels, or any other mechanism for the uniform removal of material along segment 202 may be utilized. In another variation, pull tubes will small outer diameter then thin wall thickness can be used in place of pullwires. In this variation, the pull tubes that steers the steerable segment can double up as a narrow work channel lumen for works such as guidewires or fiberscopes.

Figure 21B:
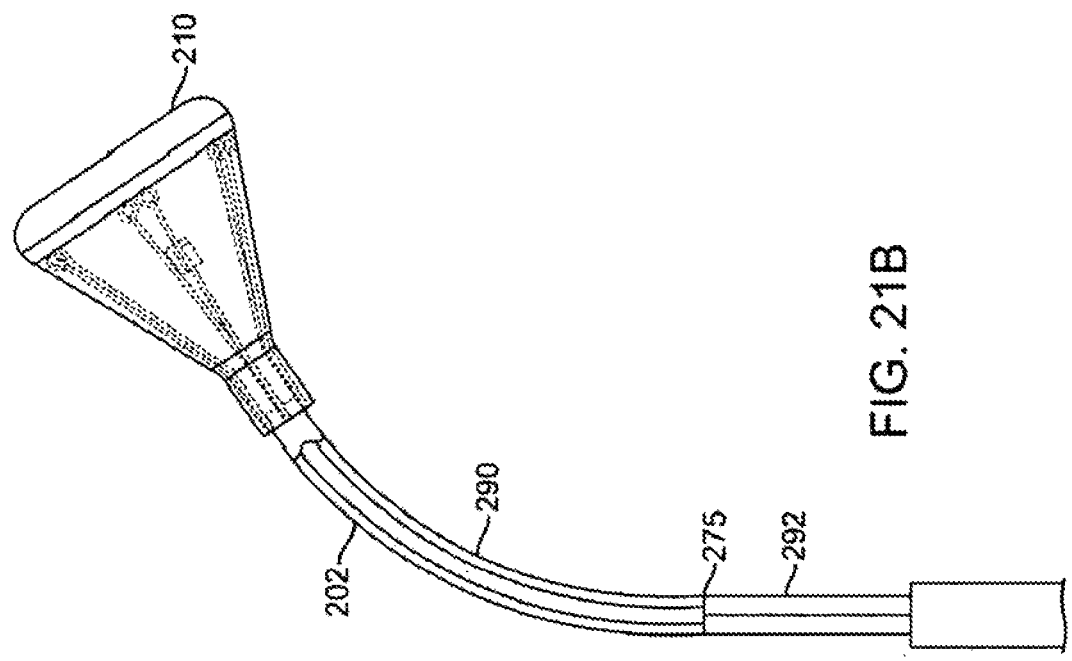
FIG. 21B shows the side view of the same device where the steerable segment is of a relatively flexible material.
Figure 21A:
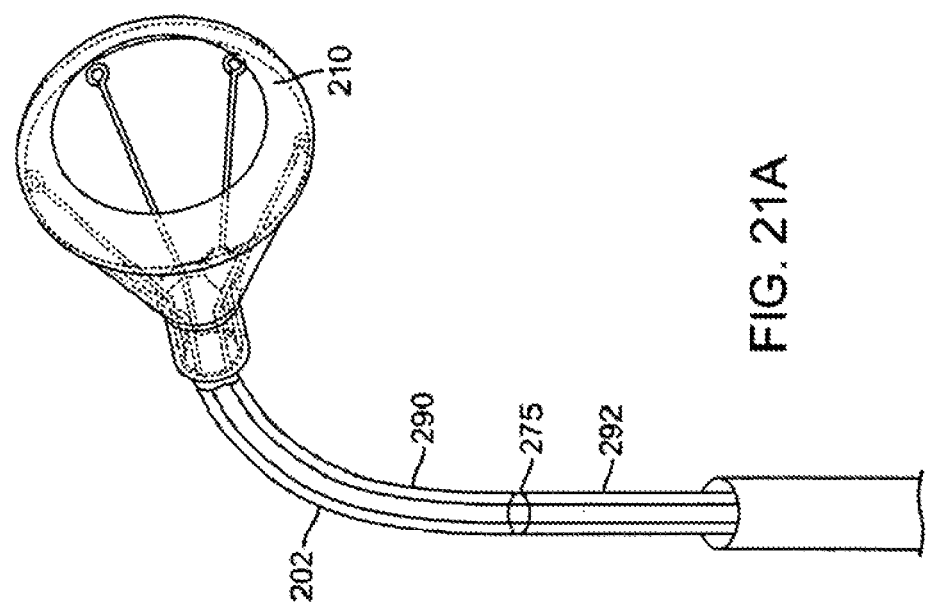
FIG. 21A shows a perspective view of a variation of a steerable tissue visualization catheter with the steerable segment made from extrusion of differing durometer.

FIGS. 21A and 21B show perspective and side views of another variation utilizing an extrusion comprised of two or more sections having different durometer values and/or material utilized as a steerable section. The example illustrates a variation having two sections, a first section 290 having a first durometer and a second section 292 having a second durometer which has a relatively higher durometer value than first section 290. This variation may accordingly produce a flexible segment that when articulated utilizing any of the mechanisms described herein has a relatively stiffer second section 292 and a relatively more flexible first section 290. The segment 202 may be extruded into a continuous segment or individual segments may be extruded separately and joined together at a joint 275. Moreover, the segment may be extruded such that the durometer value gradually declines the farther distal along the segment. Alternatively, the second section 292 may be configured to have a lower durometer value than the first section 290.

Aside from articulatable segments along the deployment catheter for positioning the hood relative to the tissue, other variations may articulate the hood assembly by utilizing a combination of the introducer sheath 294 and deployment catheter 276. As previously mentioned, a portion of the sheath itself, e.g., a distal portion, may also incorporate an articulatable section 298 which may be either pre-bent or actively steered depending upon the desired results. Thus, compound curve articulation can be made through active steering of both sheath and deployment catheter and/or passive steering of both or either sheath and deployment catheter.

Figure 22A:
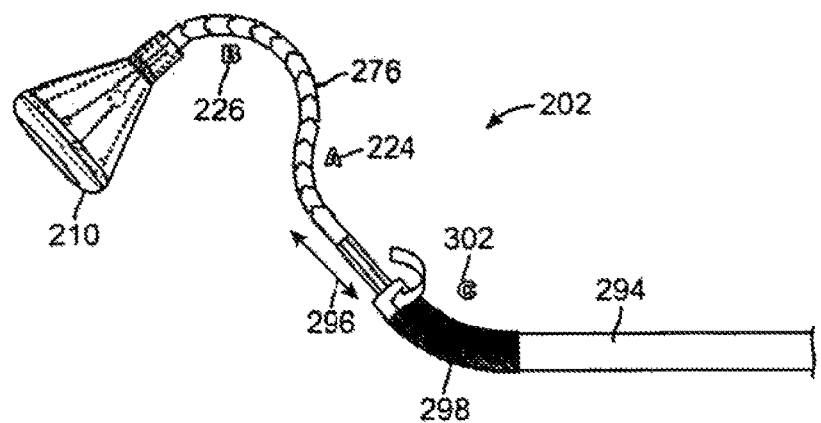
FIG. 22A shows the side view of a variation of the tissue visualization catheter with a double bend steerable segment telescoping from a pre-bent introducer sheath.
Figure 22B:
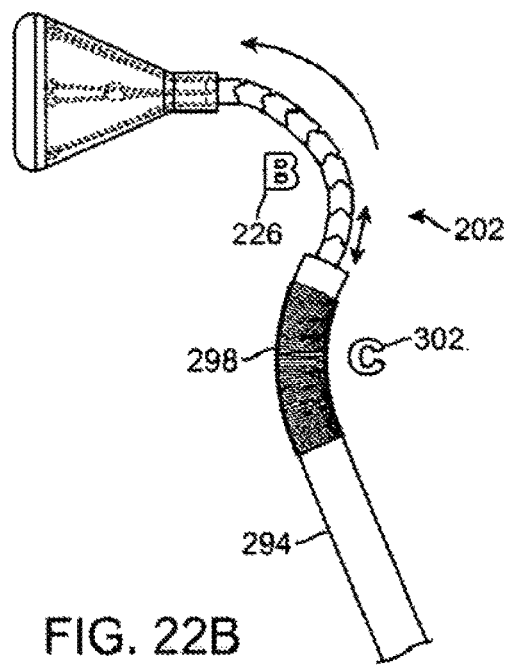
FIG. 22B shows the double bend steering by combining a passive pre-bent sheath with an actively articulated single bend steering catheter.

FIG. 22A shows a side view of a visualization assembly 210 having the actively articulated double-bend steering described above along with a sheath 294 having an articulatable distal segment 298. In this example, distal segment 298 is illustrated as being pre-bent such that when the distal segment 298 is unconstrained, segment 298 relaxes into a pre-bent configuration as shown. Thus when deployed, hood 210 may be articulated into position relative to the tissue surface via at least three curvable or curved sections, e.g., first curve 224 (Curve A), second curve 226 (Curve B), and third curve 302 defined by the distal segment 298 of sheath 294 (Curve C). By varying the tension and/or articulation between each of the curves, hood 210 may be positioned in a variety of configurations and angles. Additionally, the deployment catheter may be translated and/or rotated, as shown by directional indication 296 about a longitudinal axis of the catheter relative to sheath 294 to further provide additional degrees-of-freedom.

Figure 22C:
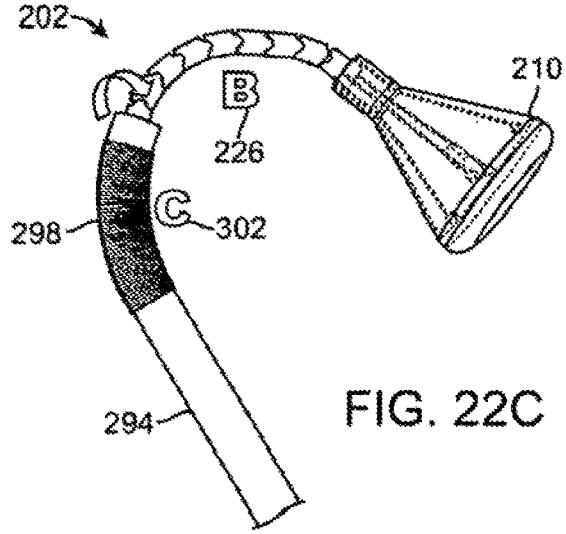
FIG. 22C shows the retroflex steering by combining a passive pre-bent sheath with an actively articulated single bend steering catheter.

Rather than utilizing the double-bend system, a single curve along the segment 202 may be utilized with the sheath 294. As illustrated in the side view of FIG. 22B, a single curve, e.g., second curve 226 may be articulated when advanced distally of distal segment 298 of sheath 294 such that the second curve 226 is articulated in a direction opposition to the curvature of distal segment 298. Alternatively, second curve 226 may be articulated to curve in the same direction as the curvature of third curve 302 such that hood 210 is retroflexed proximally relative to sheath 294, as illustrated in FIG. 22C.

Figure 22D:
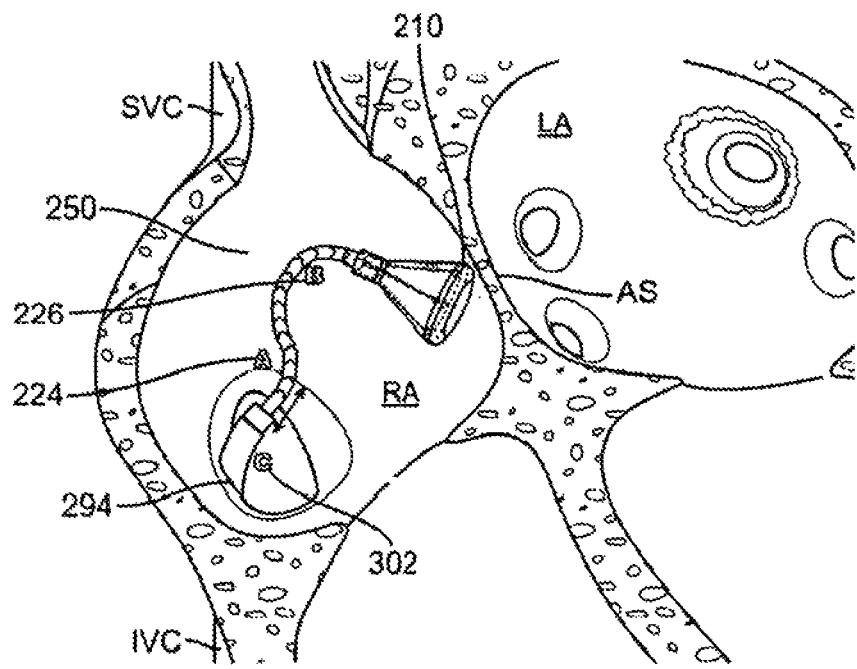
FIG. 22D illustrates the ability to steer the hood to contact tissue walls at tight angles through the interaction of the pre-bent sheath in combination with double bend steering on the catheter.
Figure 22E:
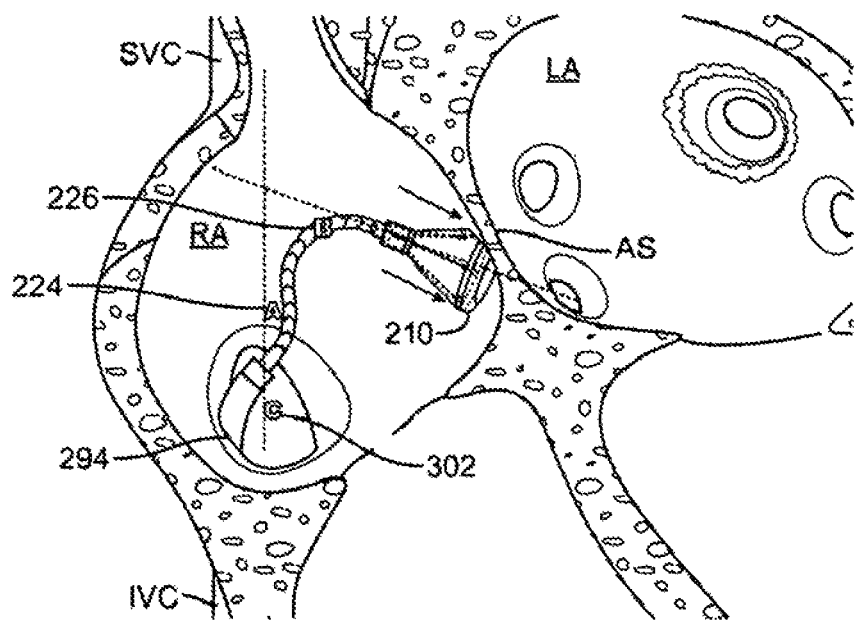
FIG. 22E shows the ability to steer and push tissue through tight angles through the interaction of the pre-bent sheath in combination with double bend steering on the catheter.
Figure 22F:
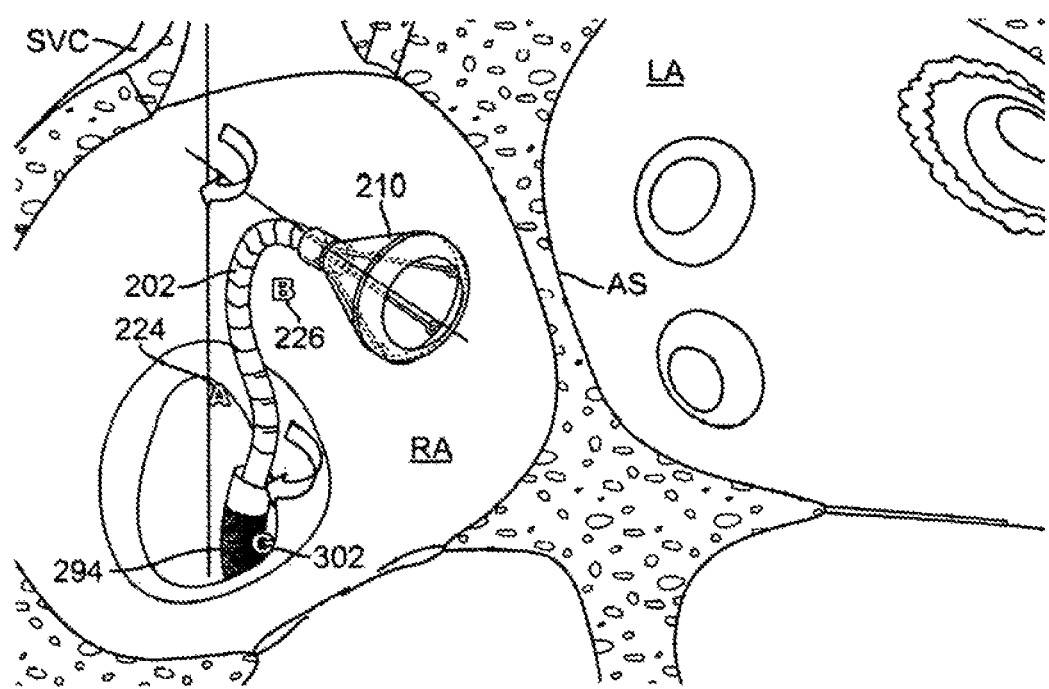
FIG. 22F shows the ability to rotate and position a curved deployment catheter in a different plane with respect to the curved sheath.

By utilizing one or all curves available through the combination of the deployment catheter with the sheath, the assembly may be used to access any region within a body lumen. For instance, FIG. 22D illustrates a partial cross-sectional view of hood assembly 210 advanced intravascularly through the inferior vena cava IVC and into the right atrium RA of a patient's heart. Segment 202 may be initially directed by third curve 302 of sheath 294 towards a region of tissue to be examined and/or treated. By rotating sheath 294 relative to the right atrium RA, an initial trajectory of hood 210 as well as articulatable segment 202 may be effectively directed. As hood 210 is deployed, first 224, second 226, and third curves 294 may be configured desirably to direct hood 210 towards a tissue region such as the atrial septum AS, e.g., for potentially accessing the left atrium LA of the heart, as shown in FIG. 22E. As further illustrated in FIG. 22F, hood 210 and segment 202 may be rotated relative to sheath 294 to redirect or reposition hood 210 on another region of tissue.

Figure 23A:
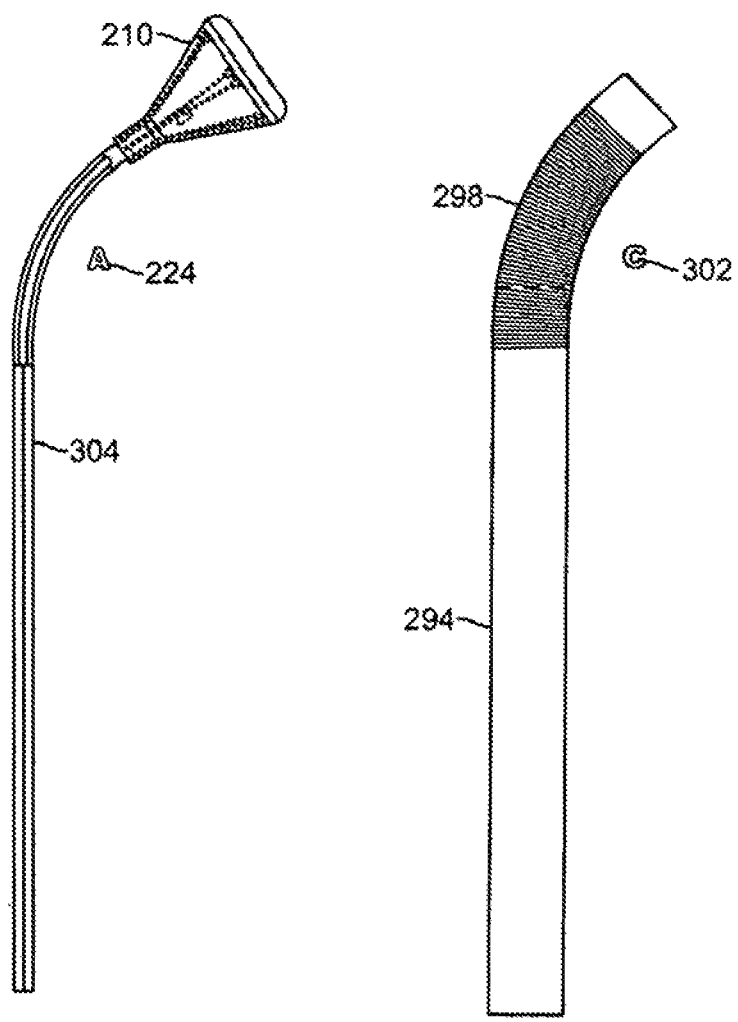
FIG. 23A shows a side view of a pre-bent tissue visualization catheter with a pre-bent introducer sheath.

FIG. 23A shows another variation of the steering system utilizing a steerable or pre-bent sheath 294 in combination with a pre-bent catheter 304 which may be straightened when constrained for intravascular delivery but free to reconfigure into a pre-bent shape with a first curve 224 when unconstrained. As shown in FIG. 23B, catheter 304 may be advanced through sheath 294 until hood 210 is deployed and catheter curve 224 is unconstrained by sheath 294. The example of FIG. 23B shows how first curve 224 of deployment catheter 304 may be aligned with third curve 302 of distal segment 298 within the same plane and same direction to retroflex hood 210 relative to sheath 294. Alternatively, catheter 304 may be torqued or initially advanced from sheath 294 such that first curve 224 is aligned in an opposite direction from third curve 302, as shown in FIG. 23C. Additionally, deployment catheter 304 may be torqued or initially advanced from sheath 294 such that first curve 224 is aligned in a non-planar configuration, e.g., perpendicularly, relative to third curve 302, as shown in FIG. 23D. Although specific directions and angles may be shown, these are intended to be illustrative and any various combinations of angles and configurations may be performed by the assembly.

Figure 24A:
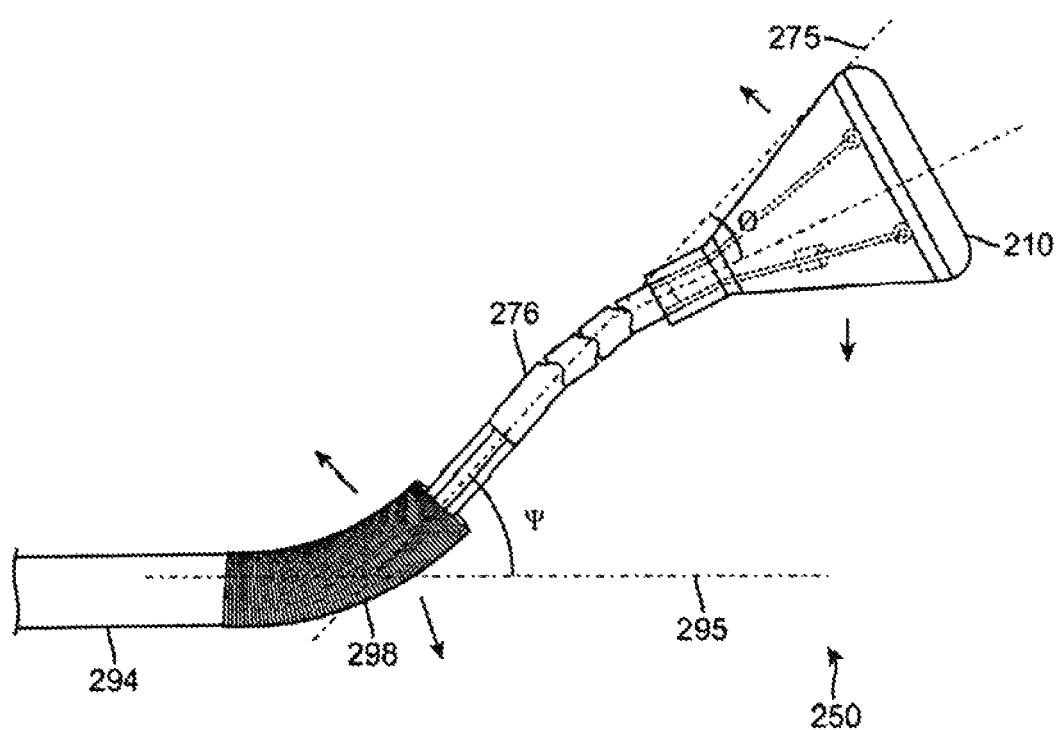
FIG. 24A shows a side view of a steerable tissue visualization catheter with an active steerable sheath.
Figure 24B:
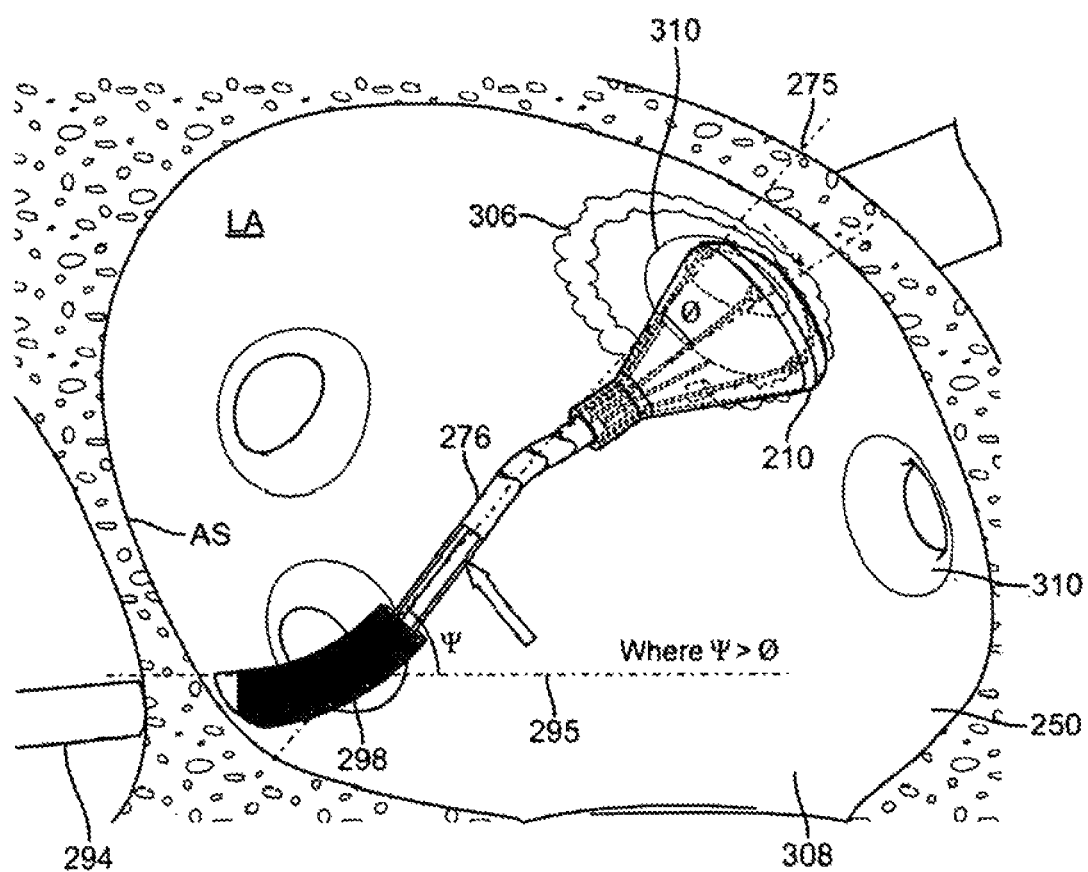
FIG. 24B shows a perspective view of the same system in the left atrium with the sheath providing an initial curvature which defines a trajectory through which the deployment catheter may be advanced towards the target tissue; the deployment catheter itself may then be finely steered to direct the hood against the target tissue to be treated.

FIG. 24A shows a side view of yet another variation utilizing a sheath 294 having a steerable or pre-bent segment 298 in combination with a deployment catheter 276 having an actively steered segment which may articulate hood 210 at an angle Φ relative to a longitudinal axis 275 of the deployment catheter 276. In this configuration, segment 298 of sheath 294 may provide the initial trajectory, as indicated by angle Ψ relative to a longitudinal axis 295 of sheath 294. In use, after sheath 294 and segment 298 has been advanced into an initial position, e.g., transseptally through the atrial septum AS and within the left atrium LA of a patient's heart as shown in FIG. 24B, the general trajectory angle Ψ may be defined by segment 298 of sheath 294 such that deployment catheter 276, once advanced distally of sheath 294, is directed generally towards the targeted tissue region such as the pulmonary vein ostia 310. With hood 210 deployed and positioned generally over the targeted tissue region, the steerable segment of deployment catheter 276 may be articulated, e.g., at an angle Φ, to further direct hood 210 upon the targeted tissue. The combination of general steering (or course steering) of sheath 294 with the articulation (or fine steering) of deployment catheter 276 may be utilized to effectively articulate hood 210 upon any desired region of tissue. Moreover, navigation may be effective when angle Ψ>Φ, although this is not necessary to effectively articulate hood 210.

Aside from steering in the deployment catheter and/or sheath, various alternatives may also incorporate steerable hood features either independently or in various combinations with any of the catheter and/or sheath articulation mechanisms described herein. An example is illustrated in the perspective views of FIGS. 25A and 25B which show a steerable hood 210 having one or more steerable members or leaflets 312, which may also function to provide structural support to the deployed hood 210. Each member or leaflet 312 may be integrated with the hood 210 material or overlaid atop and otherwise attached to hood 210. Member or leaflet 312 are illustrated as closed looped members which extend distally over hood 210, but other atraumatic configurations may be employed. A proximal end of one or more leaflets 312 may extend proximally through deployment catheter 276 such that a user may manipulate the leaflets 312 by pulling and/or pushing the leaflet 312 proximal end to effect a corresponding result along hood 210. As illustrated in FIG. 25B, upon pulling a proximal end of one leaflet 312, hood 210 may be slanted to an angle Φ, which may be defined as the angle between an axis 311 transverse to deployment catheter 276 and an axis 313 transverse to hood 210. By pulling/pushing one or more leaflet struts simultaneously, the hood 210 can be steered and slanted along different planes. Such leaflet struts 312 can be made from various materials, e.g., nitinol, stainless steel, tungsten, elgiloy, etc.

FIG. 25C shows a side view of steerable hood 210 directed against a tissue surface 316 for visualization and/or treatment. As described above, sheath 294 may be steered to provide a general trajectory and an angle Ψ to direct the deployment catheter 276 generally towards the target tissue surface 316. Once deployed hood 210 has been brought into proximity, the leaflet struts 312 may be actuated to slant or tilt hood 210 at an angle Φ such that the distal end of hood 210 may be placed directly in apposition against the tissue surface 316 to facilitate sealing, visualization, and tissue treatment.

Figure 26A:
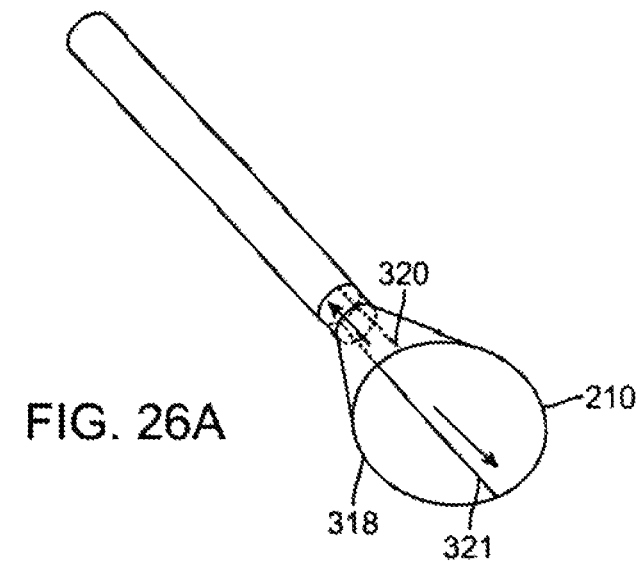
FIG. 26A shows a perspective view of the tissue visualization catheter with steerable hood.
Figure 26B:
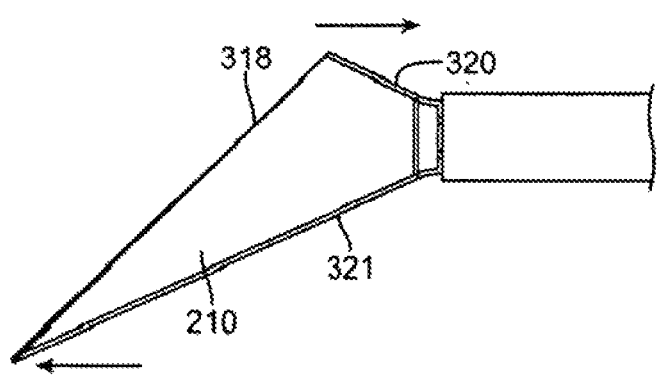
FIG. 26B shows a side view of the same device.

FIGS. 26A and 26B show perspective and side views, respectively, of another variation of a steerable hood 210 which utilizes a pair of struts 320, 321 which may be positioned along the walls of hood 210 and are connected to a circumferential member 318 providing support to the distal circumferential edge of hood 210. Similarly to the leaflet struts above, the steering struts 320, 321 may be pulled and/or pushed alternately to slant hood 210 at a desired angle.

Figure 27A:
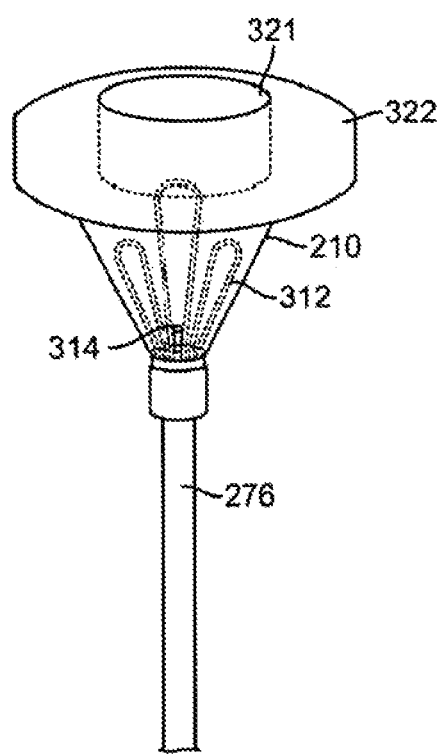
FIG. 27A shows a perspective view of a tissue visualization catheter with conforming lip at a distal end of the hood.

In yet another embodiment, articulation of hood 210 may be affected passively by having a conformable lip 322 positioned to extend distally about a circumference of hood 210, as shown in the perspective view of FIG. 27A. The conformable lip 322 can be made from an inflatable balloon shaped into a donut or toroidal shape defining a passage 321 therethrough and attached to the distal end of hood 210. The balloon can be (but is not limited to) materials such as polyurethane, silicone, rubber latex, PET (polyethylene terephthalate), etc. The conformable lip 322 can also be made from an extrusion of soft conformable materials such as polyether/polyester sponges or polystyrene (Styrofoam) and may also be transparent.

Figure 27B:
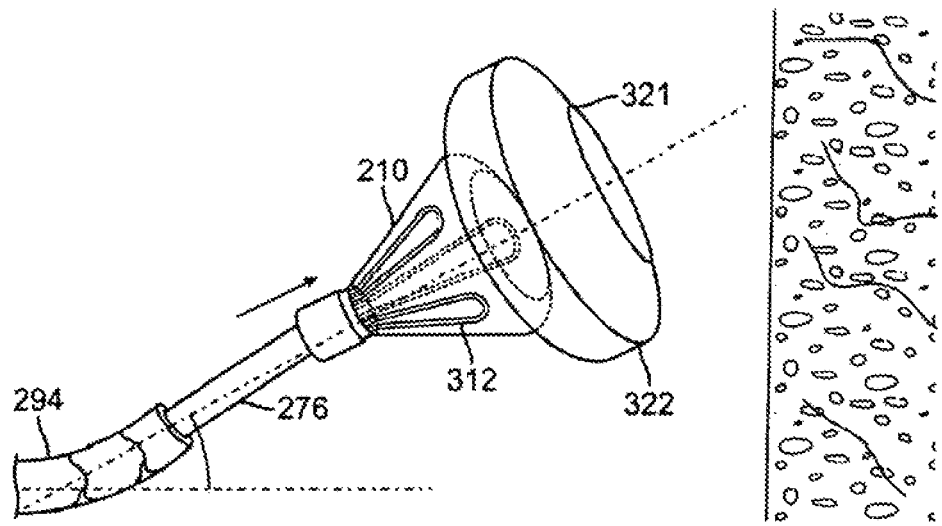
FIG. 27B shows a side view of the same device advanced towards a tissue surface at an angle defined by the steerable introducer sheath.
Figure 27C:
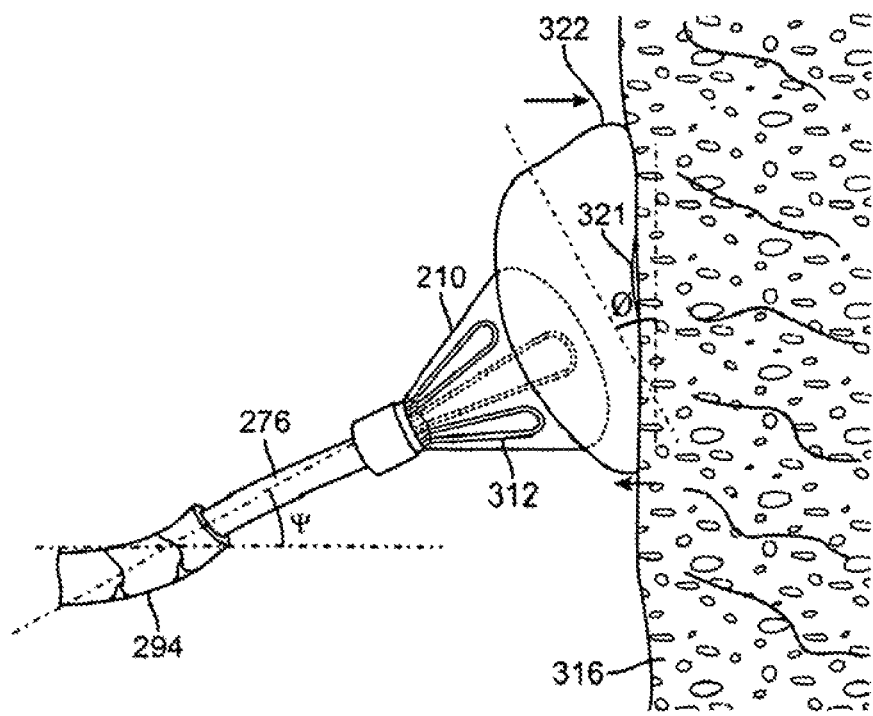
FIG. 27C illustrates the hood pressed against the targeted tissue with the lip conforming against the anatomy of the tissue.

In use, as hood 210 is advanced towards the targeted tissue region, as shown in FIG. 27B, conformable lip 322 may be inflated or otherwise expanded. As the hood 210 is pressed (possibly at an angle) against target tissue, as indicated in FIG. 27C, conformable lip 322 may deform against the anatomy of the tissue surface to facilitate sealing and visualization.

Figure 28:
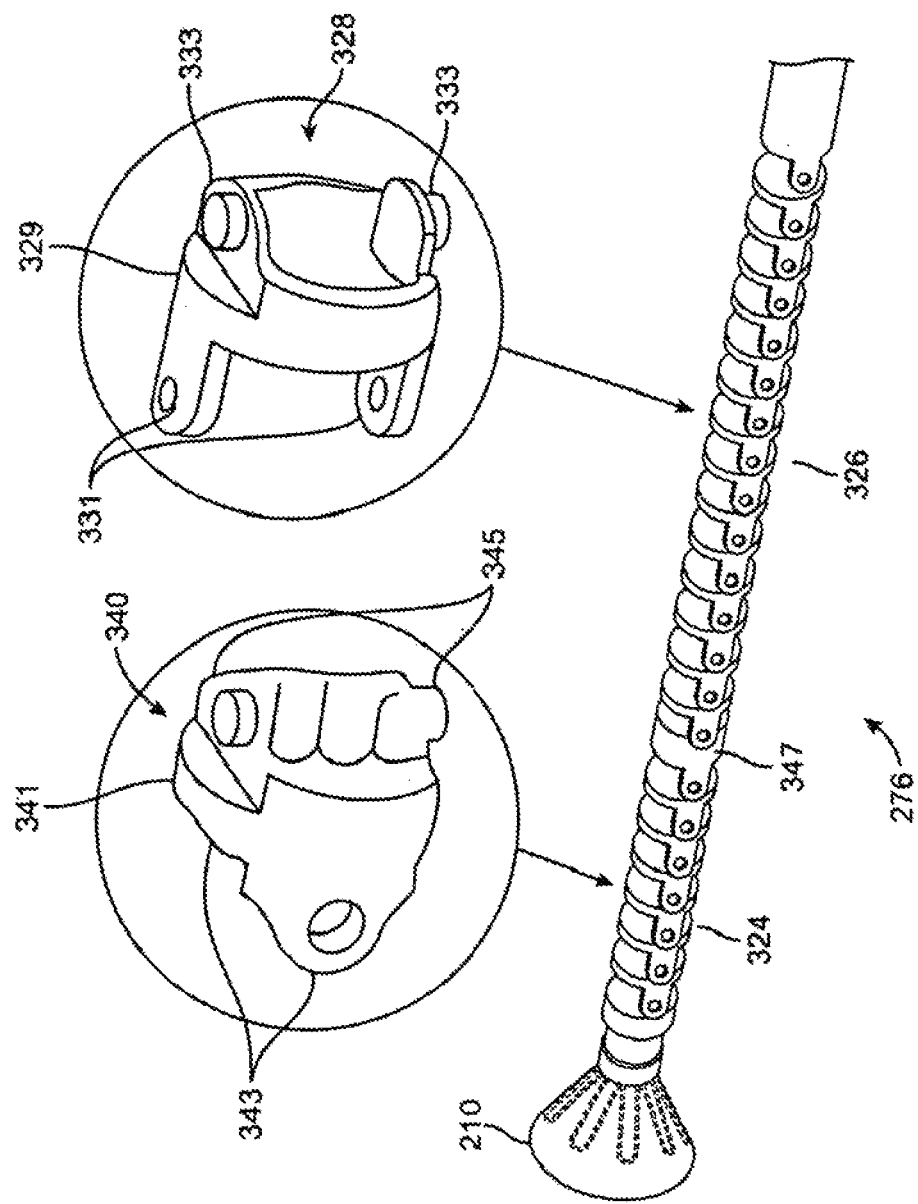
FIG. 28 shows a perspective assembly view of the steerable section of a catheter having a distal section with connected links configured to allow for multi-directional articulation, e.g., four-way articulation, and a proximal section with connected links configured to allow for articulation within a single plane, e.g., one-way articulation.

Turning now to the perspective assembly view of FIG. 28, another variation of an articulatable deployment catheter 276 is shown which comprises a distal steerable section 324 and a proximal steerable section 326 located proximally of the distal steerable section 324. An intervening link 347 may couple the sections 324, 326 to one another and provide a terminal link to which one or more pull wires may be attached in controlling one or both sections. The distal steerable section 324 may utilize individual links 340 which allow for the section 324 to be articulated in a variety of different directions and angles, e.g., four-way steering, to enable omni-direction articulation. The individual links 340 may accordingly utilize a body member 341 having a pair of yoke members 343 positioned opposite to one another and extending distally from the body member 341 and each defining an opening. A pair of pins 345 may each extend radially in opposing directions from body member 341 and in a perpendicular plane relative to a plane defined by the yoke members 343.

Figure 29A:
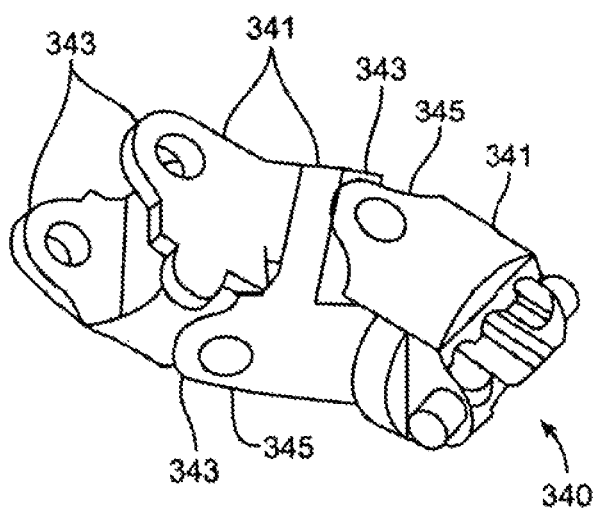
FIG. 29A illustrates a perspective detail view of the multi-directional articulation of the distal section of the steerable segment.
Figure 29B:
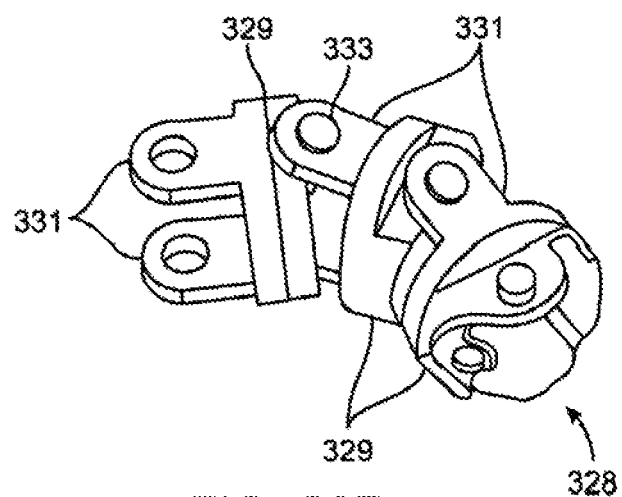
FIG. 29B illustrates a perspective detail view of articulation within a single plane of a proximal section of the steerable segment.

Turning to the perspective assembly view of FIG. 29A, the pins 345 of each link 340 may be pivotably received by the yoke members 343 of an adjacent link 340 such that the pins 345 and yoke members 343 are joined in an alternating manner. This alternating connection allows for the serially aligned links 340 to be articulated omni-directionally.

The links 328 of the proximal steering section 326 may be seen in detail in the perspective view of FIG. 28. These links 328 may also comprise a pair of yoke members 331 positioned opposite to one another and extending distally from bodey member 329. However, the pins 333 may extend radially in opposing directions while remaining in the same plane as that defined by yoke members 331. When joined together in series, as illustrated in the perspective detail view of FIG. 29B, each pin 333 of each link 328 may be pivotably received by the yoke members 331 of an adjacent link 328. Yet when joined, the composite proximal steering section 326 may be constrained to bend planarly within a single plane relative to the rest of the deployment catheter.

The combined distal steerable section 324 and a proximal steerable section 326 results in a proximal steering section which can be articulated in a single plane to retroflex the entire distal assembly and a distal steering section which can then be articulated any number of directions, e.g., four-way steering, to access anatomical structures within the heart or any other lumen. The assembly may thus be used, e.g., to create circumferential lesions around the ostia of the pulmonary veins in the left atrium while the underlying tissue remains under direct visualization through the hood.

Figure 30A:
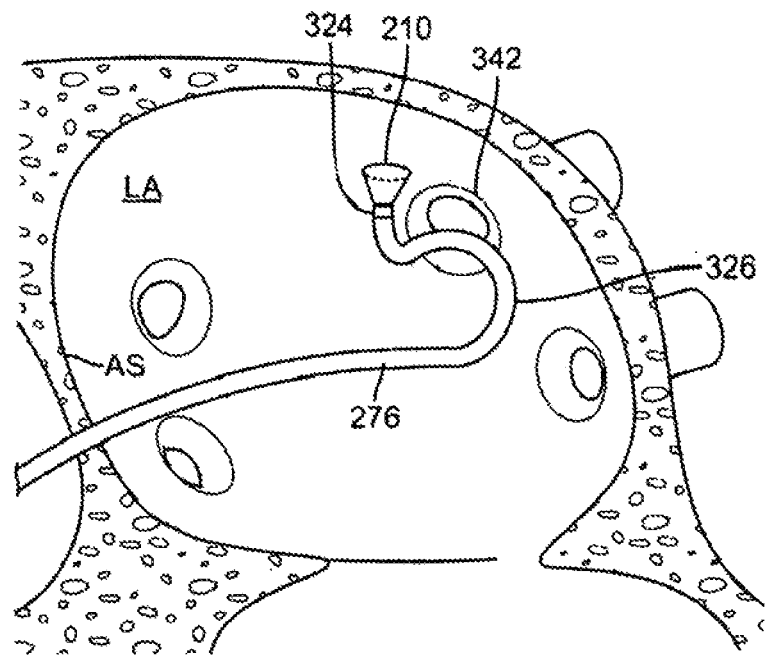
FIG. 30A to 30C illustrates a device positioned within the left atrium with the proximal steering section articulated within a single plane to retroflex the distal end and the distal steering section articulated to circumscribe the ostium of the left superior pulmonary vein for ablation treatment.
Figure 30B:
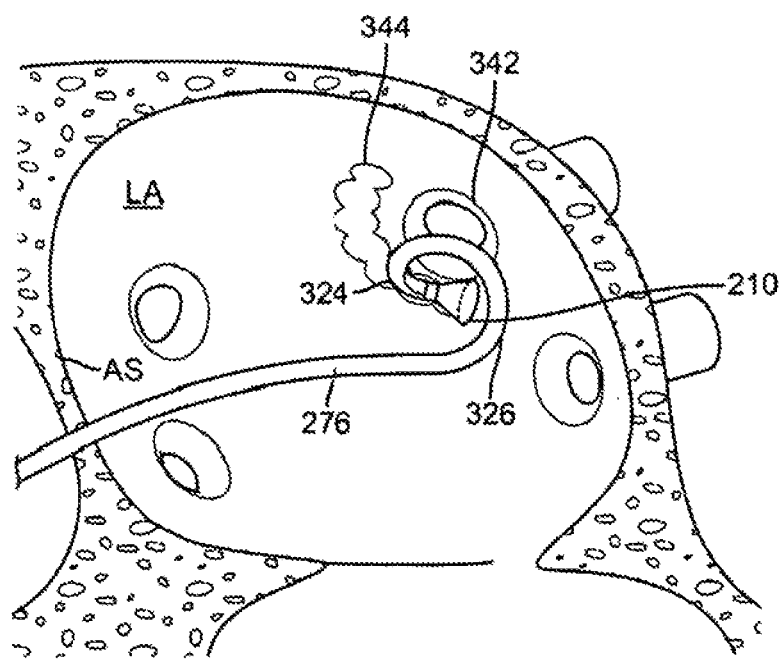
Figure 30C:
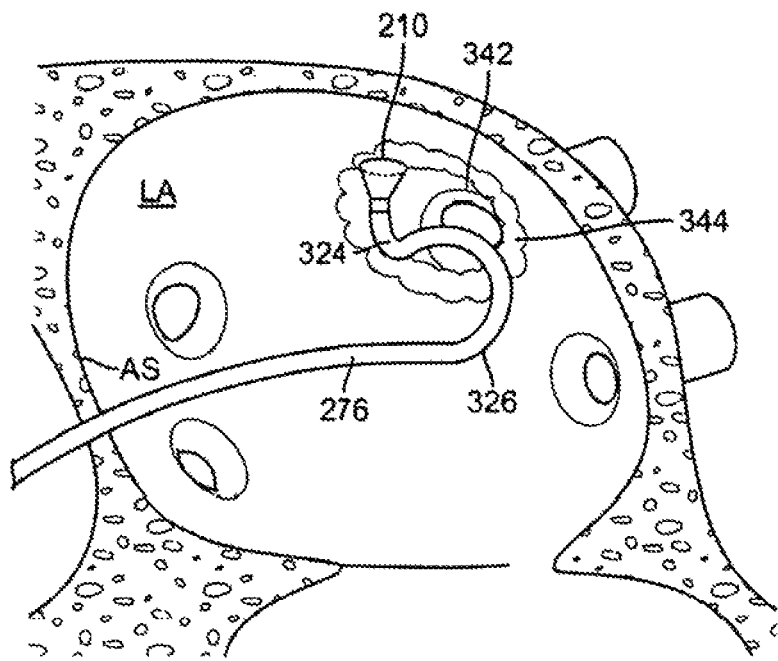

The operator may manipulate catheter 276 to position hood 210 on or around the ostia of the pulmonary veins in the left atrium LA. Once the accurate positioning of catheter 276 has been verified by real-time images captured through the imaging hood 210, as described above, ablation through any number of instruments may be accomplished. As illustrated in the partial cross-sectional view of FIG. 30A, deployment catheter 276 is shown advanced transseptally across the atrial septum AS and into the left atrium LA. To access the ostia of the pulmonary veins, such as the left superior pulmonary vein ostium 342, proximal steering section 326 may be articulated to first retroflex the distal assembly to bring hood 210 into proximity with ostium 342. Distal steering section 324 may then be articulated to bring hood 210 into contact against the tissue surface. Once the appropriate location has been determined visually, as described above, the underlying tissue may be ablated 344. As the entire circumference of ostium 342 is desirably ablated to adequately treat conditions such as atrial fibrillation, distal steering section 324 may be articulated to move hood 210 about the entire ostium 342 while ablating the tissue due to the omni-directional steering capability of steering section 324 while the curvature of proximal steering section 326 may be maintained, as shown in FIGS. 30B and 30C.

Figure 30D:
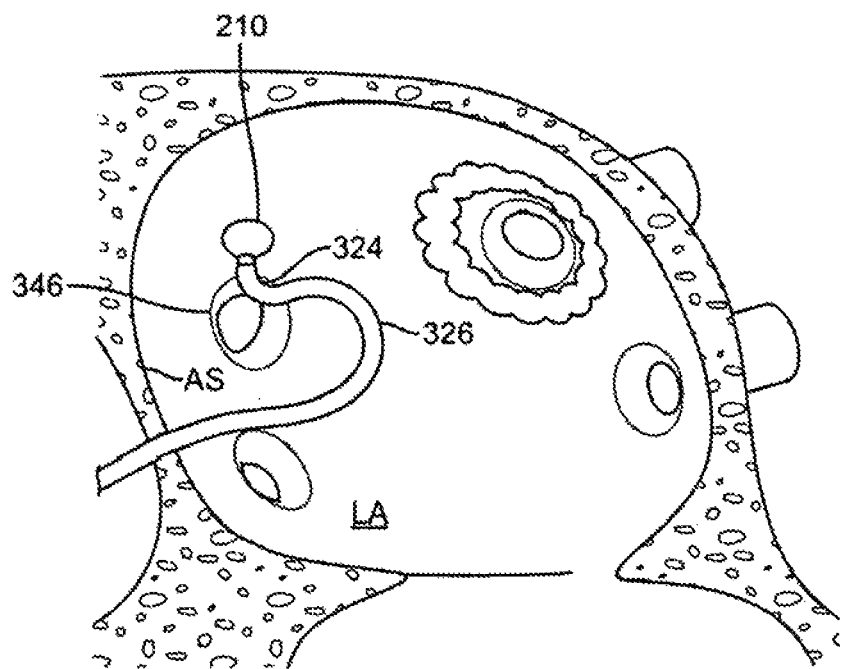
FIGS. 30D to 30F illustrates a device repositioned within the left atrium to allow the distal steering section to circumscribe the ostium of the right superior pulmonary vein for ablation treatment.
Figure 30E:
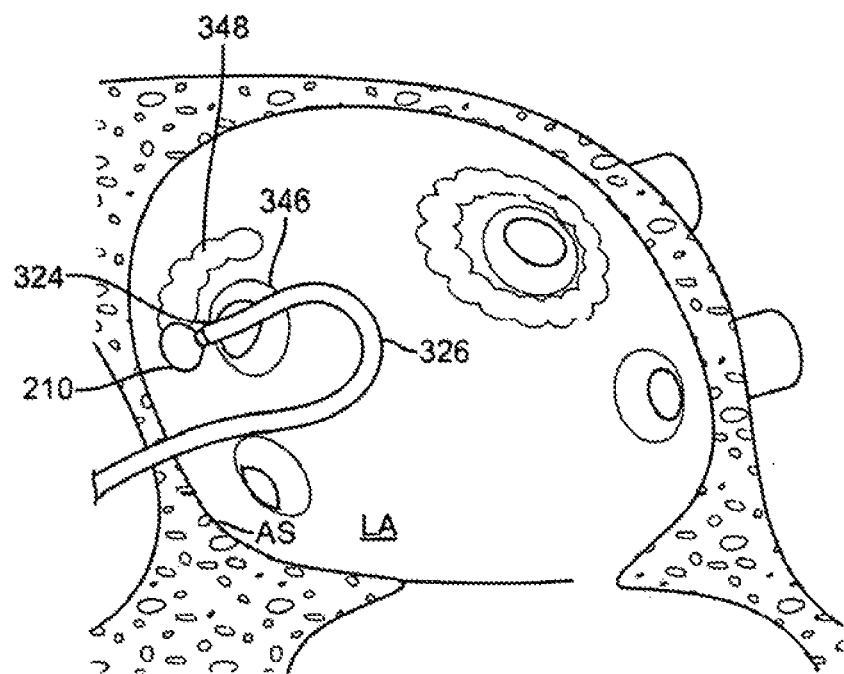
Figure 30F:
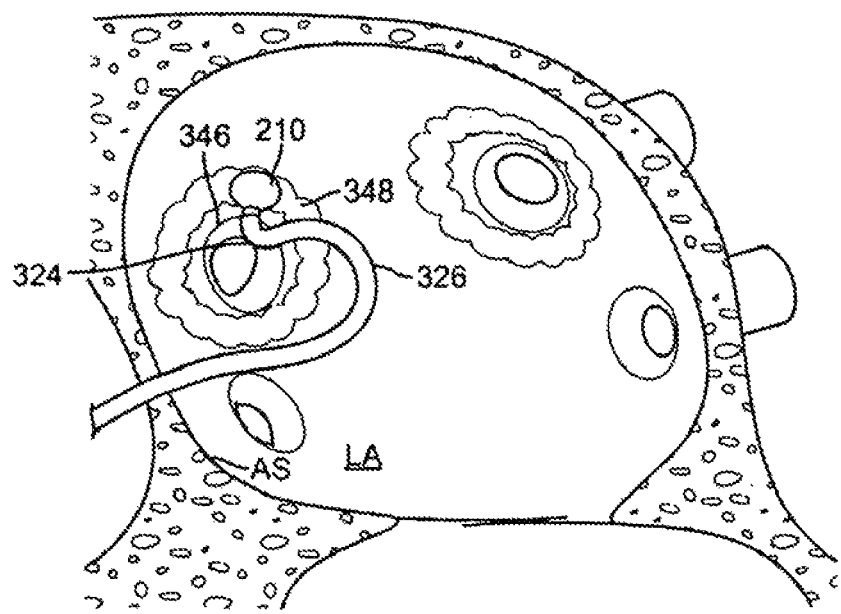

Once the ablation about a first ostium is completed, deployment catheter 276 may be repositioned by manipulating the catheter and/or adjusting the articulation of proximal steering section 326, as illustrated in FIG. 30D. Once hood 210 has been repositioned, e.g., proximate to the left superior pulmonary vein ostium 346, the process may be repeated and the underlying tissue may be ablated 348 about the ostium 346 while utilizing the steering capabilities of both steering sections 324, 326, as shown in the FIGS. 30E and 30F.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A medical manipulation assembly comprising:
   a sheath steerable in response to rotational movement of a sheath steering mechanism;
   a catheter extendable through the sheath, the catheter including:
      an elongated portion comprising a plurality of links steerable in response to rotational movement of a catheter steering mechanism, wherein the sheath and elongated portion of the catheter are independently steerable and the catheter is aligned with and slidable relative to a longitudinal axis of the sheath, and wherein the steerable elongated portion includes:
         a first channel sized to receive a visualization instrument therethrough, the first channel including a forward-facing distal opening; and
         a second channel sized to receive a tool therethrough, the second channel including a forward-facing distal opening, wherein the forward-facing distal opening of the first channel and the forward-facing distal opening of the second channel lie in a same plane; and
      a distal end effector including an outer diameter at least as large as an outer diameter of the plurality of links, the distal end effector including a tapered outer profile extending to a distal tip of the distal end effector, the second channel extending through at least a proximal portion of the distal end effector, the distal end effector at a distal end of the catheter and sized to pass through the sheath, the distal end effector configured to directly engage tissue;
   a distal end effector steering mechanism comprising at least one steerable member, the at least one steerable member coupled to the distal end effector and configured to bend the distal end effector independently of the sheath, wherein when the distal end effector is bent relative to the sheath, an axis transverse to the distal end effector is angled with respect to an axis transverse to the sheath; and
   a set of control wires, wherein at least one of the sheath or the elongated portion of the catheter includes a plurality of lumens with at least two of the plurality of lumens each sized for passage of one of the control wires of the set of control wires.

2. The medical manipulation assembly of claim 1 further comprising the visualization instrument, wherein the visualization instrument is extendable distally beyond the sheath and the catheter.

3. The medical manipulation assembly of claim 2 wherein the visualization instrument includes a camera.

4. The medical manipulation assembly of claim 2 wherein the visualization instrument includes an optical fiber.

5. The medical manipulation assembly of claim 1 wherein at least one of the sheath or the catheter is steerable by computer control.

6. The medical manipulation assembly of claim 1 wherein at least one of the sheath or the catheter is formed from an extrusion that includes the plurality of lumens.

7. The medical manipulation assembly of claim 1 wherein at least one of the plurality of lumens is configured for passage of a helically shaped member.

8. The medical manipulation assembly of claim 1 wherein a distal end of the sheath is deflectable to form a distal curve in a first direction, and wherein a distal end of the catheter is deflectable to form a distal curve in a second direction, different from the first direction, and an intermediate curve in the first direction, the intermediate curve extending proximally of the distal curve of the catheter.

9. The medical manipulation assembly of claim 1 wherein the distal end effector is articulatable.

10. The medical manipulation assembly of claim 1 wherein the distal end effector includes a hood.

11. The medical manipulation assembly of claim 1 wherein the distal end effector surrounds an open area distal of a distal opening of the second channel.

12. The medical manipulation assembly of claim 1 wherein the distal end effector is formed from a translucent material.

13. The medical manipulation assembly of claim 1 wherein the distal end effector is formed from plastic.

14. The medical manipulation assembly of claim 1 wherein a proximal end of the at least one steerable member extends to a proximal end of the catheter.

15. The medical manipulation assembly of claim 14 wherein manipulation of the proximal end of the at least one steerable member is configured to bend the distal end effector.

16. The medical manipulation assembly of claim 1 wherein the at least one steerable member is coupled to an outer surface of the distal end effector.

* * * * *

UNITED STATES PATENT AND TRADEMARK OFFICE
CERTIFICATE OF CORRECTION

| | | |
|---|---|---|
| PATENT NO. | : 12,193,638 B2 | Page 1 of 1 |
| APPLICATION NO. | : 14/843475 | |
| DATED | : January 14, 2025 | |
| INVENTOR(S) | : Chris A. Rothe et al. | |

It is certified that error appears in the above-identified patent and that said Letters Patent is hereby corrected as shown below:

In the Specification

Column 16, Line 48, change "HO" to -- 110 --

Signed and Sealed this
Twenty-fifth Day of March, 2025

Coke Morgan Stewart
*Acting Director of the United States Patent and Trademark Office*